US011135146B2

(12) United States Patent
Bellini et al.

(10) Patent No.: US 11,135,146 B2
(45) Date of Patent: Oct. 5, 2021

(54) PEROXIDE-LESS BIOPHOTONIC COMPOSITIONS AND METHODS

(71) Applicant: KLOX TECHNOLOGIES LIMITED, Dublin (IE)

(72) Inventors: Francesco Bellini, Calgary (CA); David Ohayon, Dollard-des-Ormeaux (CA); Remigio Piergallini, San Benedetto del Tronto (IT); Nikolaos Loupis, Athens (GR); William Curtis, Montreal (CA)

(73) Assignee: KLOX TECHNOLOGIES LIMITED, Dublin (IE)

(*) Notice: Subject to any disclaimer, the term of this patent is extended or adjusted under 35 U.S.C. 154(b) by 0 days.

(21) Appl. No.: 16/066,487

(22) PCT Filed: Dec. 28, 2016

(86) PCT No.: PCT/CA2016/051544
§ 371 (c)(1),
(2) Date: Jun. 27, 2018

(87) PCT Pub. No.: WO2017/113013
PCT Pub. Date: Jul. 6, 2017

(65) Prior Publication Data
US 2019/0021973 A1 Jan. 24, 2019

Related U.S. Application Data

(60) Provisional application No. 62/271,593, filed on Dec. 28, 2015.

(51) Int. Cl.
| A61K 47/00 | (2006.01) |
| A61K 36/07 | (2006.01) |
| A61K 36/074 | (2006.01) |
| A61K 36/068 | (2006.01) |
| A61K 9/06 | (2006.01) |
| A61P 17/00 | (2006.01) |
| A61N 5/06 | (2006.01) |
| C09K 11/06 | (2006.01) |
| A61K 8/49 | (2006.01) |
| A61Q 19/08 | (2006.01) |
| A61K 47/10 | (2017.01) |
| A61K 33/00 | (2006.01) |

(Continued)

(52) U.S. Cl.
CPC .............. *A61K 8/498* (2013.01); *A61K 8/14* (2013.01); *A61K 8/19* (2013.01); *A61K 8/345* (2013.01); *A61K 8/8147* (2013.01); *A61K 9/0014* (2013.01); *A61K 9/06* (2013.01); *A61K 31/35* (2013.01); *A61K 31/4166* (2013.01); *A61K 31/7008* (2013.01); *A61K 31/728* (2013.01); *A61K 33/00* (2013.01); *A61K 41/0057* (2013.01); *A61K 47/02* (2013.01); *A61K 47/10* (2013.01); *A61K 47/32* (2013.01); *A61N 5/062* (2013.01); *A61P 1/02* (2018.01); *A61P 17/02* (2018.01); *A61P 17/10* (2018.01); *A61P 29/00* (2018.01); *A61Q 19/008* (2013.01); *A61Q 19/08* (2013.01); *C09K 11/06* (2013.01); *A61K 2800/30* (2013.01); *A61K 2800/434* (2013.01); *A61K 2800/5922* (2013.01); *A61K 2800/81* (2013.01); *C09K 2211/1007* (2013.01); *C09K 2211/1088* (2013.01)

(58) Field of Classification Search
CPC ...... A61K 47/00; A61K 36/07; A61K 36/074; A61K 36/068; A61P 17/00; A61N 5/06; A09K 11/06
See application file for complete search history.

(56) References Cited

U.S. PATENT DOCUMENTS

| 3,141,321 A | 7/1964 | Rinaldi |
| 3,328,307 A | 6/1967 | Schmitz |

(Continued)

FOREIGN PATENT DOCUMENTS

| CN | 103396699 B | 11/2014 |
| DE | 1172802 B | 6/1964 |

(Continued)

OTHER PUBLICATIONS

Durrani et al., "Studies on Drugs Release Kinetics From Carbopol® 934P Tablets", Pharmaceutical Res. Supp. 8: S-135, 1991—abstract only.
Brock et al. "Use of in Vitro and in Vivo Data in the Design, Development, and Quality Control of Sustained-Release Decongestant Dosage Forms", Pharmacotherapy, 1994, vol. 14, pp. 430-437.
"Topical and Transdermal Durg Products", Dissolution Technologies, Nov. 2010, 14 pages.
Bate et al., "Helpful drug in treatment of tuberculosis of urinary bladder", American Journal of Surgery, Paul Hoeber, New York, NY, US, vol. 36, No. 2, May 1937, pp. 500-504, XP026427806.

(Continued)

*Primary Examiner* — Zohreh A Fay
(74) *Attorney, Agent, or Firm* — BCF LLP

(57) ABSTRACT

The present disclosure provides biophotonic topical compositions, kits and their uses. In some aspects, the biophotonic topical compositions of the present disclosure comprise a first chromophore, a salt selected from one or more bicarbonate or carbonate salts or a combination of the foregoing salts, and one or more gelling agents. In some aspects, the biophotonic topical compositions of the present disclosure comprise a first chromophore, one or more polyols, and one or more gelling agents. The biophotonic compositions of the present disclosure do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. The biophotonic compositions are useful for promoting wound healing and skin rejuvenation, as well as treating acne and various skin disorders.

20 Claims, 33 Drawing Sheets

(51) Int. Cl.

| | |
|---|---|
| *A61K 9/00* | (2006.01) |
| *A61K 41/00* | (2020.01) |
| *A61K 47/02* | (2006.01) |
| *A61K 47/32* | (2006.01) |
| *A61K 8/34* | (2006.01) |
| *A61K 8/81* | (2006.01) |
| *A61K 8/19* | (2006.01) |
| *A61Q 19/00* | (2006.01) |
| *A61K 8/14* | (2006.01) |
| *A61K 31/728* | (2006.01) |
| *A61K 31/4166* | (2006.01) |
| *A61K 31/7008* | (2006.01) |
| *A61P 17/10* | (2006.01) |
| *A61P 1/02* | (2006.01) |
| *A61P 17/02* | (2006.01) |
| *A61P 29/00* | (2006.01) |
| *A61K 31/35* | (2006.01) |

(56) References Cited

U.S. PATENT DOCUMENTS

| | | |
|---|---|---|
| 4,402,959 A | 9/1983 | Dybas et al. |
| 4,430,381 A | 2/1984 | Harvey et al. |
| 4,533,435 A | 8/1985 | Intili |
| 4,625,026 A | 11/1986 | Kim |
| 4,736,467 A | 4/1988 | Schwarze et al. |
| 4,855,139 A | 8/1989 | Srinivasan |
| 5,069,907 A | 12/1991 | Mixon et al. |
| 5,091,102 A | 2/1992 | Sheridan |
| 5,529,769 A | 6/1996 | Cho et al. |
| 5,639,464 A | 6/1997 | Terry et al. |
| 5,853,883 A | 12/1998 | Nohr et al. |
| 5,854,147 A | 12/1998 | Nohr et al. |
| 5,894,042 A | 4/1999 | Ferralli |
| 5,919,554 A | 7/1999 | Watterson, III et al. |
| 6,203,805 B1 | 3/2001 | Collins et al. |
| 7,598,291 B2 | 10/2009 | Nimni et al. |
| 7,722,904 B2 | 5/2010 | Schneider et al. |
| 2004/0009227 A1 | 1/2004 | Yao |
| 2004/0120990 A1* | 6/2004 | Cushman ............. A61K 9/0014 424/443 |
| 2006/0247313 A1 | 11/2006 | Murakami et al. |
| 2008/0108681 A1 | 5/2008 | Scimeca et al. |
| 2009/0069217 A1 | 3/2009 | Kato et al. |
| 2009/0220450 A1 | 9/2009 | Green et al. |
| 2009/0325885 A1 | 12/2009 | Miyata et al. |
| 2011/0081530 A1 | 4/2011 | Robinson et al. |
| 2011/0086060 A1 | 4/2011 | Bidamant et al. |
| 2011/0130459 A1 | 6/2011 | Spencer |

FOREIGN PATENT DOCUMENTS

| | | |
|---|---|---|
| WO | 2013126707 A1 | 8/2013 |
| WO | 2013155620 A1 | 10/2013 |
| WO | 2015000058 A1 | 1/2015 |

OTHER PUBLICATIONS

Henderson et al., "How does photodynamic therapy works?", Photochemistry and Photobiology, 1992, 55(1), 145-157.

Ochsner, "Photophysical and Photobiological processes in the photodynamic therapy of tumours", Journal of Photochemistry and Photobiology B: Biology, 1997, 39, 1-18.

Sharman et al., "Photodynamic therapeutics: Basic principles and clinical applications", Drug Discovery Today, 4(11), 507-517.

Sharman et al., "Role of activated oxygen species in photodynamic therapy", Methods en Enzymology, 2000, 319, 376-400.

Krumova et al., "How Lipid Unsaturation, Peroxyl Radical Partitioning, and Chromanol Lipophilic Tail Affect the Antioxidant Activity of a-Tocopherol: Direct Visualization via High-Throughput Fluorescence Studies Conducted with Fluorogenic a-Tocopherol Analogues", Journal of the American Chemistry Society, 2012, 134, 10102-10113.

* cited by examiner

PEROXIDE-LESS BIOPHOTONIC COMPOSITIONS AND METHODS

RELATED APPLICATIONS

This application claims priority to and benefit from U.S. Provisional Patent Application No. 62/271,593, filed Dec. 28, 2015, the disclosure of which is incorporated herein by reference in its entirety.

BACKGROUND OF THE DISCLOSURE

Phototherapy has recently been recognized as having a wide range of applications in both the medical, cosmetic and dental fields for use in surgeries, therapies and examinations. For example, phototherapy has been developed to treat cancers and tumors with lessened invasiveness. Phototherapy has also been used to disinfect target sites as an antimicrobial treatment. Phototherapy has also been found to promote wound healing.

Photodynamic therapy is a type of phototherapy which involves a step of systemic administration or uptake of a photosensitive agent into the diseased or injured tissue, which step is followed by site-specific application of activating light (photodynamic therapy). Such regimens, however, are often associated with undesired side-effects, including irritation due to the presence of peroxides in the compositions used in therapy. Therefore, it is an object of the present disclosure to provide new and improved compositions and methods useful in phototherapy.

SUMMARY OF THE DISCLOSURE

The present disclosure provides biophotonic compositions and methods useful in phototherapy. In some aspects, the biophotonic compositions of the present disclosure comprise one or more chromophores; one or more salts selected from bicarbonate salts, carbonate salts or a combination of the foregoing salts; and one or more gelling agents, but do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some aspects, the biophotonic compositions of the present disclosure comprise one or more chromophores; one or more salts selected from bicarbonate salts, carbonate salts or a combination of the foregoing salts; one or more polyols; and one or more gelling agents, but do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some aspects, the biophotonic compositions of the present disclosure comprise a first chromophore, one or more polyols, and one or more gelling agents, but do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. Such biophotonic compositions are useful for decreasing undesired side effects associated with oxidants, e.g., peroxides, in phototherapy.

In some aspects, there is provided a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments, there is provided a biophotonic composition comprising a first chromophore; one or more gelling agents; and one or more bicarbonate salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the one or more bicarbonate salts are selected from ammonium bicarbonate, caesium bicarbonate, potassium bicarbonate, sodium bicarbonate, choline bicarbonate, aminoguanidine bicarbonate, or tetraethylammonium bicarbonate. In some embodiments, the bicarbonate salt is sodium bicarbonate. In some embodiments, the bicarbonate salt is potassium bicarbonate.

In some embodiments, there is provided a biophotonic composition comprising a first chromophore; one or more gelling agents; and sodium bicarbonate, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments, there is provided a biophotonic composition comprising a first chromophore; one or more gelling agents; and one or more carbonate salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the one or more carbonate salts are selected from barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, or zinc carbonate. In some embodiments, the carbonate salt is calcium carbonate. In some embodiments, the carbonate salt is sodium carbonate. In some embodiments, the carbonate salt is potassium carbonate.

In some embodiments, there is provided a biophotonic composition comprising a first chromophore, one or more gelling agents, and calcium carbonate, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In certain embodiments of any of the foregoing or following, the composition further comprises at least one polyol. In some embodiments, the polyol is glycerine. In some embodiments, the polyol is at least one glycol, such as ethylene glycol and propylene glycol. In some embodiments, the glycol is propylene glycol. In some embodiments, there is provided a biophotonic composition comprising a first chromophore; one or more gelling agents; glycerine; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, there is provided a biophotonic composition comprising a first chromophore; one or more gelling agents; glycerine;

and sodium bicarbonate, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In certain embodiments, the first chromophore is present in an amount of from about 0.001% to about 40% by weight of the total composition, such as from about 0.005% to about 30% by weight of the total composition, from about 0.005% to about 20% by weight of the total composition, from about 0.005% to about 10% by weight of the total composition, from about 0.005% to about 8% by weight of the total composition, from about 0.005% to about 6% by weight of the total composition, from about 0.005% to about 4% by weight of the total composition, about 0.005% to about 2% by weight of the total composition; such as about 0.2% by weight of the total composition, about 0.4% by weight of the total composition, about 0.6% by weight of the total composition, about 0.8% by weight of the total composition, about 1% by weight of the total composition, about 1.2% by weight of the total composition, about 1.4% by weight of the total composition, about 1.6% by weight of the total composition, or about 1.8% by weight of the total composition.

In some aspects, there is provided a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the polyol is glycerine. In some embodiments, the polyol is at least one glycol. In some embodiments, the glycol is selected from ethylene glycol and propylene glycol. In some embodiments, the glycol is propylene glycol.

In some embodiments, there is provided a biophotonic composition comprising a first chromophore, one or more gelling agents, and glycerine, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In certain embodiments, wherein the biophotonic composition comprises one or more gelling agents, the gelling agent is a carbomer comprising a polymer of acrylic acid. In some embodiments, the carbomer is crosslinked.

In certain embodiments, the first chromophore is in solution in a medium of the biophotonic composition. In certain such embodiments, the medium is an aqueous substance or an alcohol, such as an aqueous substance.

In certain embodiments, the first chromophore of the biophotonic composition is a fluorescent chromophore. In certain embodiments, the first chromophore of the biophotonic composition is a xanthene dye. In some embodiments, the first chromophore is selected from Eosin Y, Eosin B, Erythrosin B, Fluorescein, Rose Bengal and Phloxin B. In some embodiments, the first chromophore is Eosin Y.

In some embodiments, the biophotonic composition further comprises a second chromophore. In certain such embodiments, the first chromophore has an emission spectrum that overlaps at least 20% with an absorption spectrum of the second chromophore. In some embodiments, the first chromophore transfers energy to the second chromophore upon illumination with a light. In some embodiments, the first chromophore is Eosin Y, and the second chromophore is one or more of Fluorescein, Phloxine B and Erythrosine B. In some embodiments, the first chromophore is Fluorescein, and the second chromophore is Eosin Y. In some embodiments, the second chromophore is present in an amount of from about 0.0001% to about 40% by weight of the total composition, such as about from about 0.0001% to about 2% by weight of the total composition.

In some embodiments, the biophotonic composition further comprises a third chromophore. In certain such embodiments, the third chromophore is a chlorophyll or saffron.

In some embodiments, the pH of the biophotonic composition is within the range of from about 4.0 to about 7.0, from about 4.0 to about 6.5, or from about 4.0 to about 5.0. In some embodiments, the pH of the biophotonic composition is within the range of from about 6.0 to about 8.0 or from about 6.5 to about 7.5.

In some embodiments, the biophotonic composition further comprises one or more healing factors selected from the group consisting of glucosamine, hyaluronic acid, and allantoin.

In some aspects, the disclosure of this application provides a method for promoting skin rejuvenation, comprising applying topically to a skin a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for promoting skin rejuvenation, comprising applying topically to a skin a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method of promoting wound healing, comprising: applying topically to a wound a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method of promoting wound healing, comprising: applying topically to a wound a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of a skin disorder, comprising: applying topically to a target skin tissue afflicted with the skin disorder a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of a skin disorder, comprising: applying topically to a target skin tissue afflicted with the skin disorder a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of acne, comprising: applying topically to a target tissue a biophotonic composition comprising a first chromophore one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of acne, comprising: applying topically to a target tissue a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of acne scars, comprising: applying topically to a target tissue a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method for biophotonic treatment of acne scars, comprising: applying topically to a target tissue a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the disclosure of this application provides a method of biophotonic treatment of on oral disease, comprising: applying topically to a target site a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the disclosure of this application provides a method of biophotonic treatment of an oral disease, comprising: applying topically to a target site a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some embodiments, the method further comprises removing the biophotonic composition after illumination.

In some embodiments, the biophotonic composition is illuminated for about 1 minute to about 30 minutes. In certain embodiments of any of the foregoing or following, the biophotonic composition is illuminated for less than about 20 minutes, about 15 minutes, about 10 minutes, or about 5 minutes.

In some embodiments, the biophotonic composition is illuminated with actinic light.

In some embodiments, the biophotonic composition is illuminated with violet and/or blue light.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of wounds.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of wounds.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment or prevention of skin disorders.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment or prevention of skin disorders.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acne.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acne.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acne scars.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acne scars.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment or prevention of an oral disease. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment or prevention of an oral disease. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the disclosure of this application provides a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acute or chronic inflammation.

In some aspects, the disclosure of this application provides a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate for use in the treatment of acute or chronic inflammation.

In some aspects, the disclosure of this application provides a kit comprising:

a) a biophotonic composition comprising: a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and b) one or more of a light source for activating the first chromophore; instructions for use of the composition and/or the light source; a dressing; and a device for applying and/or removing the composition from a treatment area.

In some aspects, the disclosure of this application provides a kit comprising a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate and one or more of a light source for activating the first chromophore, instructions for use of the composition and/or the light source, a dressing, and a device for applying and/or removing the composition from a treatment area.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of wounds.

In some aspects, the disclosure of this application provides use of a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of wounds.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment or prevention of skin disorders.

In some aspects, the disclosure of this application provides use of a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment or prevention of skin disorders.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acne.

In some aspects, the disclosure of this application provides use of biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acne.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acne scars.

In some aspects, the disclosure of this application provides use of biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acne scars.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment or prevention of an oral disease. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the disclosure of this application provides use of a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment or prevention of an oral disease. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the disclosure of this application provides use of a biophotonic composition comprising a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acute or chronic inflammation.

In some aspects, the disclosure of this application provides use of a biophotonic composition comprising a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate in the manufacture of a medicament for the treatment of acute or chronic inflammation.

DETAILED DESCRIPTION (1) Overview

Figure 1:
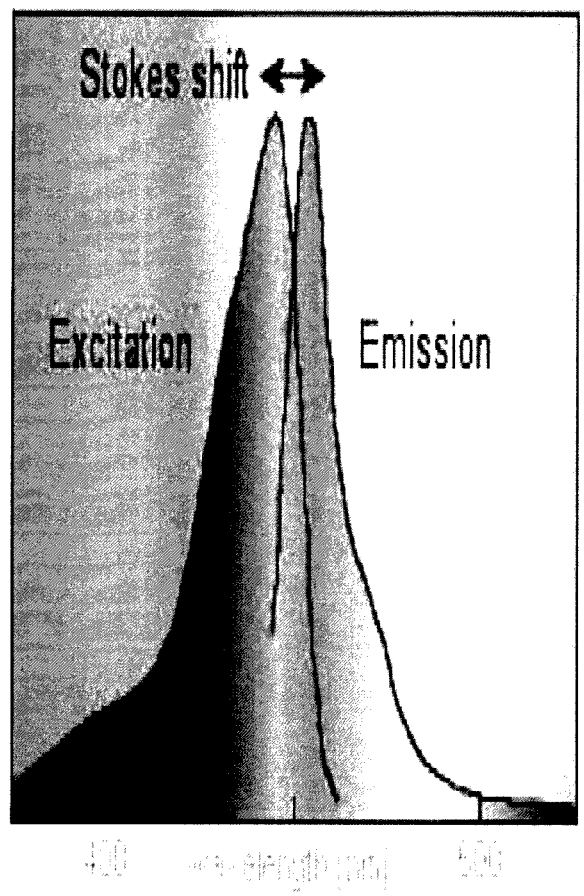
FIG. 1 illustrates the Stokes' shift.

Photodynamic therapy regimens have been developed to promote wound healing, rejuvenate facial skins and treat various skin disorders. However, these methods tend to require the presence of oxidants, such as peroxides (e.g., hydrogen peroxide and carbamide peroxide). The presence of peroxides in the composition can lead to undesired side-effects, including skin irritation and bleaching, redness and stinging, and blisters or ulcers to the patient.

Phototherapy on the other hand utilizes the therapeutic effect of light. However, expensive and sophisticated light sources are often required to provide therapeutic wavelengths and intensities of light.

The present disclosure provides biophotonic compositions which are useful in phototherapy and which include photoactive exogenous chromophores which can emit a therapeutic light or which can promote a therapeutic effect on a treatment site by activating other components of the biophotonic composition. The present disclosure also provides methods useful for promoting wound healing, cosmetic treatment of skin such as skin rejuvenation, treating acne and treating other skin disorders, treating acute or chronic inflammation, which are distinguished from conventional photodynamic therapy.

Biophotonic therapy using these compositions does not rely on the presence of an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. Therefore, the undesired side effects caused by such oxidants may be reduced, minimized, or prevented.

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. "Biophotonic composition" is a composition as described herein that may be activated by light to produce photons for biologically relevant applications.

"Gels" are defined as substantially dilute cross-linked systems. Gels may be semi-solids and exhibit substantially no flow when in the steady state at room temperature (e.g. about 20-25° C.). By steady state is meant herein during a treatment time and under treatment conditions. Gels, as defined herein, may be physically or chemically cross-linked. As defined herein, gels also include gel-like compositions such as viscous liquids.

"Topical" means as applied to body surfaces, such as the skin, mucous membranes, vagina, oral cavity, internal surgical wound sites, and the like.

Terms "chromophore", "photoactivating agent" and "photoactivator" are used herein interchangeably. A chromophore means a chemical compound, moiety, or complex, when contacted by light irradiation, is capable of absorbing the light. The chromophore readily undergoes photoexcitation and can then transfer its energy to other molecules or emit it as light.

The "initial level of fluorescence" is the level of fluorescence exhibited by a biophotonic composition of the disclosure immediately upon application of or activation with light.

"Photobleaching" means the photochemical destruction of a chromophore.

The term "actinic light" is intended to mean light energy emitted from a specific light source (e.g., lamp, LED, or laser) and capable of being absorbed by matter (e.g. the chromophore or photoactivator defined above). In some embodiments, the actinic light is visible light.

As used herein, a "hygroscopic" substance is a substance capable of taking up water, for example, by absorption or adsorption even at relative humidity as low as 50%, at room temperature (e.g. about 20-25° C.).

"Impermeable membrane" means that the material contained within the membrane is sufficiently or substantially impermeable to the surrounding environment such that the migration of such material out of the membrane, and/or the migration of the environmental components (such as water) into the membrane, is so low as to having substantially no adverse impact on the function or activity of the materials retained within the membrane. The impermeable membrane may be 'breathable' in that gas flow through the membrane is permitted whilst the flow of liquid is not permitted. The impermeable membrane may also selectively allow the migration of some of the materials through the membrane but not others.

"Wound" means an injury to any tissue, including for example, acute, subacute, delayed or difficult to heal wounds, and chronic wounds. Examples of wounds include both open and closed wounds. Wounds include, for example, burns, incisions, excisions, lesions, lacerations, abrasions, puncture or penetrating wounds, gunshot wounds, surgical wounds, contusions, hematomas, crushing injuries, ulcers (such as for example pressure, venous, pressure or diabetic), wounds caused by periodontitis (inflammation of the periodontium), or other soft tissue disorders.

"Skin rejuvenation" means a process of reducing, diminishing, retarding or reversing one or more signs of skin aging. For instance, common signs of skin aging include, but are not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. According to the present disclosure, one or more of the above signs of aging may be reduced, diminished, retarded or even reversed by the compositions and methods of the present disclosure.

(3) Biophotonic Topical Compositions

The present disclosure provides biophotonic compositions. Biophotonic compositions are compositions that are, in a broad sense, activated by light (e.g., photons) of specific wavelength. These compositions contain at least one exogenous chromophore which is activated by light and accelerates the dispersion of light energy, which leads to light carrying on a therapeutic effect on its own, and/or to the photochemical activation of other agents contained in the composition. The composition may comprise an agent which, when mixed with the first chromophore and subsequently activated by light, can be photochemically activated which may lead to the formation of oxygen radicals, such as singlet oxygen.

In some aspects, the present disclosure provides biophotonic compositions comprising at least a first chromophore; one or more gelling agents; and one or more salts selected from bicarbonate salts, carbonate salts or a combination of the foregoing salts, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides biophotonic compositions comprising at least a first chromophore; one or more salts selected from bicarbonate salts, carbonate salts or a combination of the foregoing salts; one or more polyols; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the biophotonic compositions of the present disclosure comprise a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In certain such aspects, said biophotonic compositions maintain, within a first minute of illumination, at least 80% of their initial levels of fluorescence.

In some aspects, the present disclosure provides a first composition and a second composition that are mixed together before use to generate a biophotonic composition, wherein the first composition comprises at least a first chromophore and one or more gelling agents and the second composition comprises one or more salts selected from bicarbonate salts, carbonate salts or a combination of the foregoing salts, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and the second composition comprises one or more salts selected from bicarbonate salts, carbonate salts or a combination of the foregoing salts and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and one or more gelling agents and the second composition comprises one or more salts selected from bicarbonate salts, carbonate salts or a combination of the foregoing salts and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition that are mixed together before use to generate a biophotonic composition, wherein the first composition comprises at least a first chromophore, and the second composition comprises one or more gelling agents and one or more polyols, which, when mixed with the first composition and subsequently activated by light, disperses the light energy, leading to the photochemical activation of the combined compositions, which may lead to the formation of oxygen radicals, such as singlet oxygen. In certain such embodiments, said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, and one or more gelling agents and the second composition comprises one or more polyols, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, and one or more polyols and the second composition comprises one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, and one or more gelling agents and the second composition comprises one or more polyols and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, and one or more polyols and the second composition comprises one or more polyols and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and the second composition comprises one or more bicarbonate salts or carbonate salts or a combination of the foregoing salts; one or more gelling agents; and one or more polyols, which, when mixed with the first composition and subsequently activated by light, disperses the light energy, leading to the photochemical activation of the combined compositions, which may lead to the formation of oxygen radicals, such as singlet oxygen. In certain such embodiments, said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and one or more gelling agents and the second composition comprises one or more polyols and one or more bicarbonate salts or carbonate salts or a combination of the foregoing salts, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and one or more polyols and the second composition comprises one or more gelling agents and one or more bicarbonate salts or carbonate salts or a combination of the foregoing salts, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and one or more gelling agents and the second composition comprises one or more bicarbonate salts or carbonate salts or a combination of the foregoing salts; one or more polyols; and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore and one or more polyols and the second composition comprises one or more bicarbonate salts or carbonate salts or a combination of the foregoing salts; one or more polyols; and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, one or more gelling agents, and one or more polyols and the second composition comprises one or more bicarbonate salts or carbonate salts or a combination of the foregoing salts; one or more polyols; and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some aspects, the present disclosure provides a first composition and a second composition, wherein the first composition comprises at least a first chromophore, one or more gelling agents, and one or more polyols and the second composition comprises one or more bicarbonate salts or carbonate salts or a combination of the foregoing salts, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a treatment site on to which the biophotonic composition is topically applied. Differing wavelengths of light may have different and complementary therapeutic effects on tissue. Stokes' shift is illustrated in FIG. 1.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues. Moreover, in embodiments of the composition containing bicarbonate or carbonate salts, microbubbling within the composition has been observed by the inventor which may be associated with the generation of oxygen species by the photoactivated chromophores. This may have a physical impact on the tissue to which it is applied, for example by dislodging biofilm and debridement of necrotic tissue or providing a pressure stimulation. The biofilm can also be pre-treated with an oxygen-releasing agent to weaken the biofilm before treating with the composition of the present disclosure.

In certain embodiments, the biophotonic compositions of the present disclosure are substantially transparent/translucent and/or have high light transmittance in order to permit light dissipation into and through the composition. In this way, the area of tissue under the composition can be treated both with the fluorescent light emitted by the composition and the light irradiating the composition to activate it, which may benefit from the different therapeutic effects of light having different wavelengths.

The % transmittance of the biophotonic composition can be measured in the range of wavelengths from 250 nm to 800 nm using, for example, a Perkin-Elmer Lambda 9500 series UV-visible spectrophotometer. Alternatively, a Synergy HT spectrophotometer (BioTek Instrument, Inc.) can be used in the range of wavelengths from 380 nm to 900 nm.

Transmittance is calculated according to the following equation:

$$A_\lambda = \log_{10}\frac{I_0}{I} = \log_{10}\frac{1}{T}.$$

where A is absorbance, T is transmittance, $I_0$ is intensity of radiation before passing through material, I is intensity of light passing through material.

The values can be normalized for thickness. As stated herein, % transmittance (translucency) is as measured for a 2 mm thick sample at a wavelength of 526 nm. It will be clear that other wavelengths can be used.

The biophotonic compositions of the present disclosure are for topical uses. The biophotonic compositions can be in the form of a semi-solid or viscous liquid, such as a gel, or are gel-like, and which have a spreadable consistency at room temperature (e.g. about 20-25° C.), prior to illumination. By spreadable is meant that the composition can be topically applied to a treatment site at a thickness of about 0.5 mm to about 3.0 mm, about 0.5 mm to about 2.5 mm, about 1.0 mm to about 2.0 mm. In some embodiments, the composition can be topically applied to a treatment site at a thickness of about 2.0 mm or about 1.0 mm. Spreadable compositions can conform to a topography of a treatment site, e.g. a wound. This can have advantages over a non-conforming material in that a better and/or more complete illumination of the treatment site can be achieved and the compositions are easy to apply and remove.

These compositions may be described based on the components making up the composition. Additionally or alternatively, the compositions of the present disclosure have functional and structural properties and these properties may also be used to define and describe the compositions. Individual components of the composition of the present disclosure are detailed as below.

(a) Chromophores

The biophotonic topical compositions of the present disclosure comprise one or more chromophores, which can be considered exogenous, e.g., are not naturally present in skin or tissue. When a biophotonic composition of the present disclosure is illuminated with light, the chromophore(s) are excited to a higher energy state. When the chromophore(s)' electrons return to a lower energy state, they emit photons with a lower energy level, thus causing the emission of light of a longer wavelength (Stokes' shift). In the proper environment, some of this energy release is transferred to oxygen and causes the formation of oxygen radicals, such as singlet oxygen.

Suitable chromophores for the biophotonic compositions of the disclosure can be fluorescent dyes (or stains), although other dye groups or dyes (biological and histological dyes, food colorings, carotenoids, naturally occurring fluorescent and other dyes) can also be used.

In some embodiments, the biophotonic topical composition of the present disclosure comprises a first chromophore which undergoes partial or complete photobleaching upon application of light. By photobleaching is meant a photochemical destruction of the chromophore which can generally be visualized as a loss of color. Without wishing to be bound by theory, the biophotonic compositions of the present disclosure may take longer to photobleach upon application of light than compositions comprising one or more chromophores and one or more oxidants selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the biophotonic compositions of the disclosure maintain, within a first minute of illumination, at least 80% of their initial level of fluorescence.

In some embodiments, the first chromophore absorbs at a wavelength in the range of the visible spectrum, such as at a wavelength of about 380-800 nm, about 380-700 nm, or about 380-600 nm. In some embodiments, the first chromophore absorbs at a wavelength of about 200-800 nm, about 200-700 nm, about 200-600 nm or about 200-500 nm. In some embodiments, the first chromophore absorbs at a wavelength of about 200-600 nm. In some embodiments, the first chromophore absorbs light at a wavelength of about 200-300 nm, about 250-350 nm, about 300-400 nm, about 350-450 nm, about 400-500 nm, about 400-600 nm, about 450-650 nm, about 600-700 nm, about 650-750 nm or about 700-800 nm.

In some embodiments, the first chromophore is present in an amount of about 0.001-40% by weight of the composition. In some embodiments, the first chromophore is present in an amount of about 0.005-2%, about 0.01-1%, about 0.01-2%, about 0.05-1%, about 0.05-2%, about 0.1-1%, about 0.1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition.

In some embodiments, the first chromophore is present in an amount of 0.001-40% by weight of the composition. In some embodiments, the first chromophore is present in an amount of 0.005-2%, 0.01-1%, 0.01-2%, 0.05-1%, 0.05-2%, 0.1-1%, 0.1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore is present in an amount of at least 0.2% by weight of the composition.

In some embodiments, the first chromophore is present in an amount of about 0.05% by weight of the composition. In some embodiments, the first chromophore is present in an amount of about 0.1% by weight of the composition. In some embodiments, the first chromophore is present in an amount of about 0.15% by weight of the composition. In some embodiments, the first chromophore is present in an amount of about 0.2% by weight of the composition. In some embodiments, the first chromophore is present in an amount of about 0.25% by weight of the composition. In some embodiments, the first chromophore is present in an amount of about 0.3% by weight of the composition. In some embodiments, the first chromophore is present in an amount of about 0.35% by weight of the composition. In some embodiments, the first chromophore is present in an amount of about 0.4% by weight of the composition. In some embodiments, the first chromophore is present in an amount of about 0.45% by weight of the composition. In some embodiments, the first chromophore is present in an amount of about 0.5% by weight of the composition. In some embodiments, the first chromophore is present in an amount of about 0.55% by weight of the composition. In some embodiments, the first chromophore is present in an amount of about 0.6% by weight of the composition. In some embodiments, the first chromophore is present in an amount of about 0.65% by weight of the composition. In some embodiments, the first chromophore is present in an amount of about 0.7% by weight of the composition. In some embodiments, the first chromophore is present in an amount of about 0.75% by weight of the composition. In some embodiments, the first chromophore is present in an amount of about 0.8% by weight of the composition. In some embodiments, the first chromophore is present in an amount of about 0.85% by weight of the composition. In some embodiments, the first chromophore is present in an amount of about 0.9% by weight of the composition. In some embodiments, the first chromophore is present in an amount of about 0.95% by weight of the composition. In some embodiments, the first chromophore is present in an amount of about 1% by weight of the composition.

In some embodiments, the first chromophore is present in an amount of 0.05% by weight of the composition. In some embodiments, the first chromophore is present in an amount of 0.1% by weight of the composition. In some embodiments, the first chromophore is present in an amount of 0.15% by weight of the composition. In some embodiments, the first chromophore is present in an amount of 0.2% by weight of the composition. In some embodiments, the first chromophore is present in an amount of 0.25% by weight of the composition. In some embodiments, the first chromophore is present in an amount of 0.3% by weight of the composition. In some embodiments, the first chromophore is present in an amount of 0.35% by weight of the composition. In some embodiments, the first chromophore is present in an amount of 0.4% by weight of the composition. In some embodiments, the first chromophore is present in an amount of 0.45% by weight of the composition. In some embodiments, the first chromophore is present in an amount of 0.5% by weight of the composition. In some embodiments, the first chromophore is present in an amount of 0.55% by weight of the composition. In some embodiments, the first chromophore is present in an amount of 0.6% by weight of the composition. In some embodiments, the first chromophore is present in an amount of 0.65% by weight of the composition. In some embodiments, the first chromophore is present in an amount of 0.7% by weight of the composition. In some embodiments, the first chromophore is present in an amount of 0.75% by weight of the composition. In some embodiments, the first chromophore is present in an amount of 0.8% by weight of the composition. In some embodiments, the first chromophore is present in an amount of 0.85% by weight of the composition. In some embodiments, the first chromophore is present in an amount of 0.9% by weight of the composition. In some embodiments, the first chromophore is present in an amount of 0.95% by weight of the composition. In some embodiments, the first chromophore is present in an amount of 1% by weight of the composition.

In some embodiments, the first chromophore is present in an amount of at least about 0.05% by weight of the composition. In some embodiments, the first chromophore is present in an amount of at least about 0.1% by weight of the composition. In some embodiments, the first chromophore is present in an amount of at least about 0.15% by weight of the composition. In some embodiments, the first chromophore is present in an amount of at least about 0.2% by weight of the composition. In some embodiments, the first chromophore is present in an amount of at least about 0.25% by weight of the composition. In some embodiments, the first chromophore is present in an amount of at least about 0.3% by weight of the composition. In some embodiments, the first chromophore is present in an amount of at least about 0.35% by weight of the composition. In some embodiments, the first chromophore is present in an amount of at least about 0.4% by weight of the composition. In some embodiments, the first chromophore is present in an amount of at least about 0.45% by weight of the composition. In some embodiments, the first chromophore is present in an amount of at least about 0.5% by weight of the composition. In some embodiments, the first chromophore is present in an amount of at least about 0.55% by weight of the composition. In some embodiments, the first chromophore is present in an amount of at least about 0.6% by weight of the composition. In some embodiments, the first chromophore is present in an amount of at least about 0.65% by weight of the composition. In some embodiments, the first chromophore is present in an amount of at least about 0.7% by weight of the composition. In some embodiments, the first chromophore is present in an amount of at least about 0.75% by weight of the composition. In some embodiments, the first chromophore is present in an amount of at least about 0.8% by weight of the composition. In some embodiments, the first chromophore is present in an amount of at least about 0.85% by weight of the composition. In some embodiments, the first chromophore is present in an amount of at least about 0.9% by weight of the composition. In some embodiments, the first chromophore is present in an amount of at least about 0.95% by weight of the composition. In some embodiments, the first chromophore is present in an amount of at least about 1% by weight of the composition.

In some embodiments, the first chromophore is present in an amount of at least 0.05% by weight of the composition. In some embodiments, the first chromophore is present in an amount of at least 0.1% by weight of the composition. In some embodiments, the first chromophore is present in an amount of at least 0.15% by weight of the composition. In some embodiments, the first chromophore is present in an amount of at least 0.2% by weight of the composition. In some embodiments, the first chromophore is present in an amount of at least 0.25% by weight of the composition. In some embodiments, the first chromophore is present in an amount of at least 0.3% by weight of the composition. In some embodiments, the first chromophore is present in an amount of at least 0.35% by weight of the composition. In some embodiments, the first chromophore is present in an amount of at least 0.4% by weight of the composition. In some embodiments, the first chromophore is present in an amount of at least 0.45% by weight of the composition. In some embodiments, the first chromophore is present in an amount of at least 0.5% by weight of the composition. In some embodiments, the first chromophore is present in an amount of at least 0.55% by weight of the composition. In some embodiments, the first chromophore is present in an amount of at least 0.6% by weight of the composition. In some embodiments, the first chromophore is present in an amount of at least 0.65% by weight of the composition. In some embodiments, the first chromophore is present in an amount of at least 0.7% by weight of the composition. In some embodiments, the first chromophore is present in an amount of at least 0.75% by weight of the composition. In some embodiments, the first chromophore is present in an amount of at least 0.8% by weight of the composition. In some embodiments, the first chromophore is present in an amount of at least 0.85% by weight of the composition. In some embodiments, the first chromophore is present in an amount of at least 0.9% by weight of the composition. In some embodiments, the first chromophore is present in an amount of at least 0.95% by weight of the composition. In some embodiments, the first chromophore is present in an amount of at least 1% by weight of the composition.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic composition of the present disclosure.

The biophotonic compositions disclosed herein may include at least one additional chromophore (e.g., a second or third chromophore). Combining chromophores may increase photo-absorption by the combined dye molecules and enhance absorption and photo-biomodulation selectivity. This creates multiple possibilities of generating new photosensitive, and/or selective chromophores mixtures.

Figure 2:
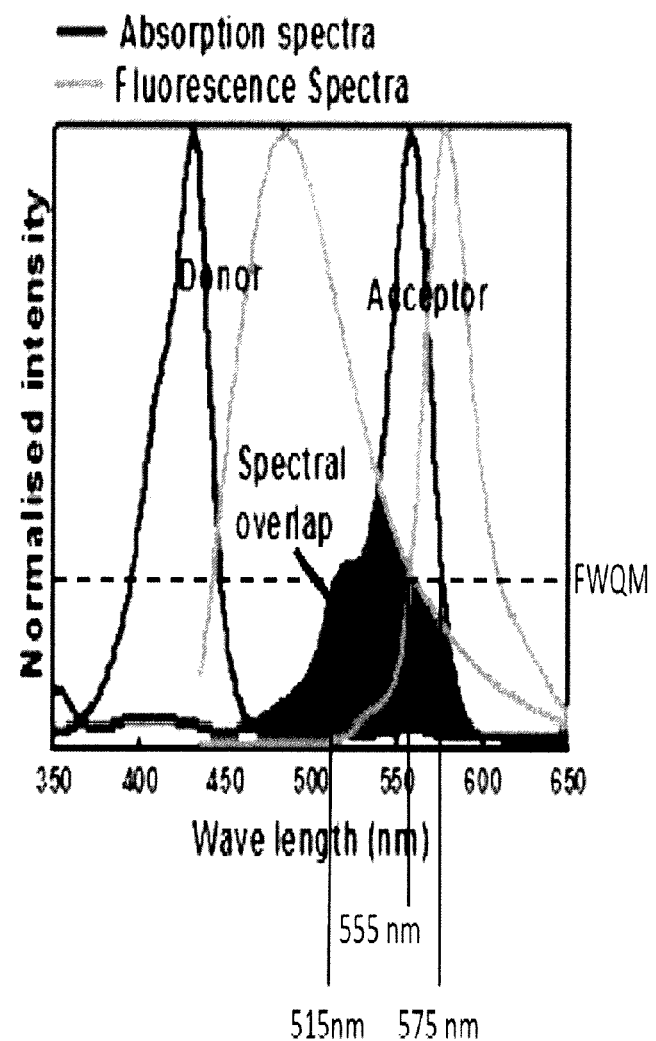
FIG. 2 illustrates the absorption and emission spectra of donor and acceptor chromophores. The spectral overlap between the absorption spectrum of the acceptor chromophore and the emission spectrum of the donor chromophore is also shown.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore (FIG. 2).

Figure 3:
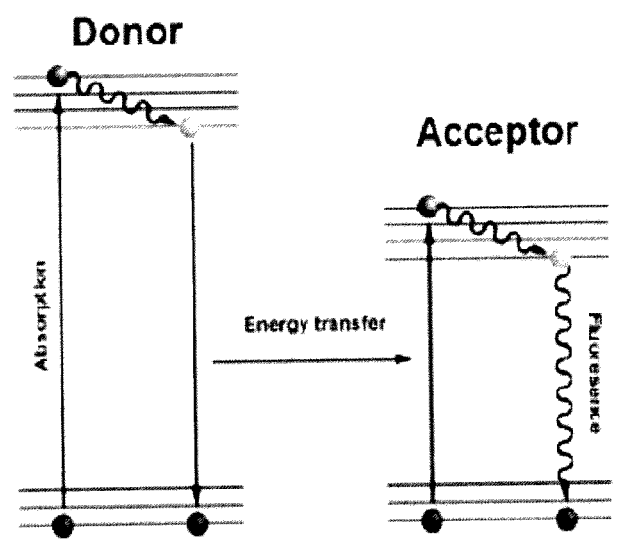
FIG. 3 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, it is thought that the more overlap there is between the donor chromophore's emission spectra and the acceptor chromophore's absorption spectra, the better a donor chromophore can transfer energy to the acceptor chromophore.

In some embodiments, the biophotonic topical composition of the present disclosure further comprises a second chromophore. In some embodiments, the first chromophore has an emission spectrum that overlaps at least about 80%, about 70%, about 60%, about 50%, about 40%, about 30%, about 20%, or about 10% with an absorption spectrum of the second chromophore. In some embodiments, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Percentage (%) spectral overlap, as used herein, means the % overlap of a donor chromophore's emission wavelength range with an acceptor chromophore's absorption wavelength range, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (about 515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In some embodiments, the second chromophore has an absorption wavelength that is relatively longer than that of the first chromophore within the range of about 50-250 nm, about 25-150 nm or about 10-100 nm.

As discussed above, the application of light to the compositions of the present disclosure can result in a cascade of energy transfer between the chromophores. In some embodiments, such a cascade of energy transfer provides photons that penetrate the epidermis, dermis and/or mucosa at the target tissue, including, such as, a site of wound, or a tissue afflicted with acne or a skin disorder. In some embodiments, such a cascade of energy transfer is not accompanied by concomitant generation of heat. In some other embodiments, the cascade of energy transfer does not result in tissue damage.

Optionally, in embodiments wherein the biophotonic topical composition comprises a first and a second chromophore, the first chromophore is present in an amount of about 0.005-40% by weight of the composition, and the second chromophore is present in an amount of about 0.0001-40% by weight of the composition. In some embodiments, the total weight by weight of the first chromophore or combination of chromophores may be in the amount of about 0.005-40% by weight of the composition. In some embodiments, the first chromophore is present in an amount of about 0.005-1%, about 0.005-2%, about 0.01-2%, about 0.02-1%, about 0.02-2%, about 0.05-1%, about 0.05-2%, about 0.05-1%, about 0.05-2%, about 0.1-1%, about 0.1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition. In some embodiments, the second chromophore is present in an amount of about 0.0001-2%, about 0.001-1%, about 0.001-2%, about 0.001-0.01%, about 0.01-0.1%, about 0.1-1%, about 0.1-2%, about 1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the total weight by weight of the first chromophore or combination of chromophores may be in the amount of about 0.005-1%, about 0.005-2%, about 0.01-2%, about 0.05-2%, about 0.1-1%, about 0.1-2%, about 0.5-1%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition.

In some embodiments, when the biophotonic topical composition comprises a first and a second chromophore, the first chromophore is present in an amount of 0.005-40% by weight of the composition, and the second chromophore is present in an amount of 0.0001-40% by weight of the composition. In some embodiments, the total weight by weight of the first chromophore or combination of chromophores may be in the amount of 0.005-40% by weight of the composition. In some embodiments, the first chromophore is present in an amount of 0.005-1%, 0.005-2%, 0.01-2%, 0.02-1%, 0.02-2%, 0.05-1%, 0.05-2%, 0.05-1%, 0.05-2%, 0.1-1%, 0.1-2%, 1-5%, 2.5-7.5%, 5-10%, 7.5-12.5%, 10-15%, 12.5-17.5%, 15- 20%, 17.5-22.5%, 20-25%, 22.5-27.5%, 25-30%, 27.5-32.5%, 30-35%, 32.5-37.5%, or 35-40% by weight of the composition. In some embodiments, the first chromophore is present in an amount of at least 0.2% by weight of the composition. In some embodiments, the second chromophore is present in an amount of 0.0001-2%, 0.001-1%, 0.001-2%, 0.001-0.01%, 0.01-0.1%, 0.1-1%, 0.1-2%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the total weight by weight of the first chromophore or combination of chromophores may be in the amount of 0.005-1%, 0.005-2%, 0.01-2%, 0.05-2%, 0.1-1%, 0.1-2%, 0.5-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore or combination of chromophores is present in an amount of at least 0.2% by weight of the composition.

In some embodiments, when the biophotonic topical composition comprises a first, a second chromophore, and a third chromophore, the first chromophore is present in an amount of about 0.005-40% by weight of the composition, the second chromophore is present in an amount of about 0.0001-40% by weight of the composition, and the third chromophore is present in an amount of about 0.0001-40% by weight of the composition. In some embodiments, the total weight by weight of the first chromophore or combination of chromophores may be in the amount of 0.005-40% by weight of the composition. In some embodiments, the first chromophore is present in an amount of about 0.005-1%, about 0.005-2%, about 0.01-2%, about 0.02-1%, about 0.02-2%, about 0.05-1%, about 0.05-2%, about 0.05-1%, about 0.1-1%, about 0.1-2%, about 0.05-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition. In some embodiments, the second chromophore is present in an amount of about 0.0001-2%, about 0.001-1%, about 0.001-2%, about 0.001-0.01%, about 0.01-0.1%, about 0.1-1%, about 0.1-2%, about 1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the third chromophore is present in an amount of about 0.0001-2%, about 0.001-1%, about 0.001-2%, about 0.001-0.01%, about 0.01-0.1%, about 0.1-1%, about 0.1-2%, about 1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the total weight by weight of the first chromophore or combination of chromophores may be in the amount of about 0.005-1%, about 0.005-2%, about 0.01-2%, about 0.05-2%, about 0.1-1%, about 0.1-2%, about 0.5-1%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore or combination of chromophores is present in an amount of at least about 0.2% by weight of the composition.

In some embodiments, when the biophotonic topical composition comprises a first, a second chromophore, and a third chromophore, the first chromophore is present in an amount of 0.005-40% by weight of the composition, the second chromophore is present in an amount of 0.0001-40% by weight of the composition, and the third chromophore is present in an amount of 0.0001-40% by weight of the composition. In some embodiments, the total weight by weight of chromophore or combination of chromophores may be in the amount of 0.005-40% by weight of the composition. In some embodiments, the first chromophore is present in an amount of 0.005-1%, 0.005-2%, 0.01-2%, 0.02-1%, 0.02-2%, 0.05-1%, 0.05-2%, 0.05-1%, 0.1-2%, 0.05-2%, 1-5%, 2.5-7.5%, 5-10%, 7.5-12.5%, 10-15%, 12.5-17.5%, 15- 20%, 17.5-22.5%, 20-25%, 22.5-27.5%, 25-30%, 27.5-32.5%, 30-35%, 32.5-37.5%, or 35-40% by weight of the composition. In some embodiments, the second chromophore is present in an amount of 0.0001-2%, 0.001-1%, 0.001-2%, 0.001-0.01%, 0.01-0.1%, 0.1-1%, 0.1-2%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the third chromophore is present in an amount of 0.0001-2%, 0.001-1%, 0.001-2%, 0.001-0.01%, 0.01-0.1%, 0.1-1%, 0.1-2%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the total weight by weight of chromophore or combination of chromophores may be in the amount of 0.005-1%, 0.005-2%, 0.01-2%, 0.05-2%, 0.1-1%, 0.1-2%, 0.5-1%, 0.5-2%, 1-5%, 2.5-7.5%, 5-10%, 7.5-12.5%, 10-15%, 12.5-17.5%, 15- 20%, 17.5-22.5%, 20-25%, 22.5-27.5%, 25-30%, 27.5-32.5%, 30-35%, 32.5-37.5%, or 35-40% by weight of the composition.

In some embodiments, the chromophore or chromophores are selected such that their emitted fluorescent light, upon photoactivation, is within one or more of the green, yellow, orange, red and infrared portions of the electromagnetic spectrum, for example having a peak wavelength within the range of about 490 nm to about 800 nm. In some embodiments, the emitted fluorescent light has a power density of between 0.005 to about 10 mW/cm$^2$, about 0.5 to about 5 mW/cm$^2$.

Suitable chromophores useful in the biophotonic topical compositions of the present disclosure include, but are not limited to the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene Derivatives

Exemplary xanthene dyes include but are not limited to Eosin B (4',5'-dibromo,2',7'-dinitr-o-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropyl-benzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tri-bromo-fluorescein, dianion); eosin derivative (2',4',5',7'-tetrachloro-fluorescein, dianion); eosin; eosin dicetyl-pyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodo-fluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-amino-phenothiazine; and 1,9-dimethyl-3-diethyl-amino-7-dibutyl-amino-phenothiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In some embodiments, the composition of the present disclosure includes any of the chromophores listed above, or a combination thereof, so as to provide a biophotonic impact at the application site. This is a distinct application of these agents and differs from the use of chromophores as simple stains or as a catalyst for photo-polymerization.

Chromophores can be selected, for example, on their emission wavelength properties in the case of fluorophores, on the basis of their energy transfer potential, their ability to generate reactive oxygen species, or their antimicrobial effect. These needs may vary depending on the condition requiring treatment. For example, chlorophylls may have an antimicrobial effect on bacteria found on the face.

In some embodiments, the composition includes Eosin Y as a first chromophore. In some embodiments, the composition includes Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. This absorbed and re-emitted light is thought to be transmitted throughout the composition, and also to be transmitted into the site of treatment.

In some embodiments, the composition includes the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine. Other synergistic chromophore combinations are also possible.

By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when photoactivated in the presence of molecular oxygen, however it has a low quantum yield in terms of emitted fluorescent light. Rose Bengal has a peak absorption around 540 nm and so is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal as well as emitting some energy as fluorescence.

Chromophore combinations can also have a synergistic effect in terms of their photoactivated state. For example, two chromophores may be used, one of which emits fluorescent light when activated in the blue and green range, and the other which emits fluorescent light in the red, orange and yellow range, thereby complementing each other and irradiating the target tissue with a broad wavelength of light having different depths of penetration into target tissue and different therapeutic effects.

(b) Gelling Agent

The biophotonic topical compositions of the present disclosure comprise one or more gelling agents. In some embodiments, the disclosure provides biophotonic compositions that comprise at least a first chromophore; one or more salts selected from bicarbonate salts, carbonate salts or a combination of the foregoing salts; and one or more gelling agents. In some embodiments the disclosure provides biophotonic compositions that comprise at least a first chromophore; one or more salts selected from bicarbonate salts, carbonate salts or a combination of the foregoing salts; one or more polyols, and one or more gelling agents. In some embodiments the disclosure provides biophotonic compositions that comprise at least a first chromophore, one or more polyols, and one or more gelling agents.

A gelling agent for use according to the present disclosure may comprise any ingredient suitable for use in a topical biophotonic formulation as described herein. The gelling agent may be an agent capable of forming a cross-linked matrix, including physical and/or chemical cross-links. The gelling agent can be biocompatible, and may be biodegradable. In some embodiments, the gelling agent is able to form a hydrogel or a hydrocolloid. An appropriate gelling agent is one that can form a viscous liquid or a semisolid. In some embodiments, the gelling agent and/or the composition has appropriate light transmission properties. It is also important to select a gelling agent which will allow biophotonic activity of the chromophore(s). For example, some chromophores require a hydrated environment in order to fluoresce. The gelling agent may be able to form a gel by itself or in combination with other ingredients such as water or another gelling agent, or when applied to a treatment site, or when illuminated with light.

The gelling agent of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly (methacrylamide), poly(dimethylacrylamide), and poly(N-isopropyl-acrylamide); poly(olefinic alcohol)s such as poly (vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); silicones, polyvinyl silicates, tetramethoxyorthosilicates, methyltrimethoxyorthosilicates, tetraalkoxyorthosilicates, trialkoxyorthosilicates, pressure sensitive silicone adhesives (such as BioPSA from Dow-Corning), and polyvinylamines.

The gelling agent of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or about 100,000, or about 1,000,000) and/or cross-linked polyacrylic acid polymer.

In some embodiments, the one or more gelling agents comprise about 0.01-20% by weight of the biophotonic composition. In some embodiments, the one or more gelling agents are present in an amount of about 0.01-10% by weight of the biophotonic composition. In some embodiments, the one or more gelling agents are present in an amount of about 0.01-5% by weight of the biophotonic composition. In some embodiments, the one or more gelling agents are present in an amount of about 0.01-2% by weight of the biophotonic composition. In some embodiments, the one or more gelling agents are present in an amount of about 0.01-1% by weight of the biophotonic composition. In some embodiments, the one or more gelling agents are present in an amount of about 0.05-20% by weight of the biophotonic composition. In some embodiments, the one or more gelling agents are present in an amount of about 0.05-10% by weight of the biophotonic composition. In some embodiments, the one or more gelling agents are present in an amount of about 0.05-5% by weight of the biophotonic composition. In some embodiments, the one or more gelling agents are present in an amount of about 0.05-2% by weight of the biophotonic composition. In some embodiments, the one or more gelling agents are present in an amount of about 0.05-1% by weight of the biophotonic composition. In some embodiments, the one or more gelling agents are present in an amount of about 0.1-20% by weight of the biophotonic composition. In some embodiments, the one or more gelling agents are present in an amount of about 0.1-10% by weight of the biophotonic composition. In some embodiments, the one or more gelling agents are present in an amount of about 0.1-5% by weight of the biophotonic composition. In some embodiments, the one or more gelling agents are present in an amount of about 0.1-2% by weight of the biophotonic composition. In some embodiments, the one or more gelling agents comprise are present in an amount of 0.5-20% by weight of the biophotonic composition. In some embodiments, the one or more gelling agents are present in an amount of about 0.5-10% by weight of the biophotonic composition. In some embodiments, the one or more gelling agents are present in an amount of about 0.5-5% by weight of the biophotonic composition. In some embodiments, the one or more gelling agents are present in an amount of about 0.5-2% by weight of the biophotonic composition. In some embodiments, the one or more gelling agents are present in an amount of about 0.5-1% by weight of the biophotonic composition. In some embodiments, the one or more gelling agents are present in an amount of about 1-20% by weight of the biophotonic composition. In some embodiments, the one or more gelling agents are present in an amount of about 1-10% by weight of the biophotonic composition. In some embodiments, the one or more gelling agents are present in an amount of about 1-5% by weight of the biophotonic composition. In some embodiments, the one or more gelling agents are present in an amount of about 1-4% by weight of the biophotonic composition. In some embodiments, the one or more gelling agents are present in an amount of about 1-3% by weight of the biophotonic composition. In some embodiments, the one or more gelling agents are present in an amount of about 1-2% by weight of the biophotonic composition. In some embodiments, the one or more gelling agents are present in an amount of about 1.5-2% by weight of the biophotonic composition. In some embodiments, the one or more gelling agents are present in an amount of about 5-20% by weight of the biophotonic composition. In some embodiments, the one or more gelling agents are present in an amount of about 10-20% by weight of the biophotonic composition. In some embodiments, the one or more gelling agents are present in an amount of about 15-20% by weight of the biophotonic composition. In some embodiments, the one or more gelling agents are present in an amount of about 5-10% by weight of the biophotonic composition. In some embodiments, the one or more gelling agents are present in an amount of about 1% by weight of the biophotonic composition. In some embodiments, the one or more gelling agents are present in an amount of about 1.25% by weight of the biophotonic composition. In some embodiments, the one or more gelling agents are present in an amount of about 1.5% by weight of the biophotonic composition. In some embodiments, the one or more gelling agents are present in an amount of about 1.75% by weight of the biophotonic composition. In some embodiments, the one or more gelling agents are present in an amount of about 2% by weight of the biophotonic composition. In some embodiments, the one or more gelling agents are present in an amount of about 2.5% by weight of the biophotonic composition. In some embodiments, the one or more gelling agents are present in an amount of about 3% by weight of the biophotonic composition.

In some embodiments, the one or more gelling agents are present in an amount of 0.01-20% by weight of the biophotonic composition. In some embodiments, the one or more gelling agents are present in an amount of 0.01-10% by weight of the biophotonic composition. In some embodiments, the one or more gelling agents are present in an amount of 0.01-5% by weight of the biophotonic composition. In some embodiments, the one or more gelling agents are present in an amount of 0.01-2% by weight of the biophotonic composition. In some embodiments, the one or more gelling agents are present in an amount of 0.01-1% by weight of the biophotonic composition. In some embodiments, the one or more gelling agents are present in an amount of 0.05-20% by weight of the biophotonic composition. In some embodiments, the one or more gelling agents are present in an amount of 0.05-10% by weight of the biophotonic composition. In some embodiments, the one or more gelling agents are present in an amount of 0.05-5% by weight of the biophotonic composition. In some embodiments, the one or more gelling agents are present in an amount of 0.05-2% by weight of the biophotonic composition. In some embodiments, the one or more gelling agents are present in an amount of 0.05-1% by weight of the biophotonic composition. In some embodiments, the one or more gelling agents are present in an amount of 0.1-20% by weight of the biophotonic composition. In some embodiments, the one or more gelling agents are present in an amount of 0.1-10% by weight of the biophotonic composition. In some embodiments, the one or more gelling agents are present in an amount of 0.1-5% by weight of the biophotonic composition. In some embodiments, the one or more gelling agents are present in an amount of 0.1-2% by weight of the biophotonic composition. In some embodiments, the one or more gelling agents are present in an amount of 0.5-20% by weight of the biophotonic composition. In some embodiments, the one or more gelling agents are present in an amount of 0.5-10% by weight of the biophotonic composition. In some embodiments, the one or more gelling agents are present in an amount of 0.5-5% by weight of the biophotonic composition. In some embodiments, the one or more gelling agents are present in an amount of 0.5-2% by weight of the biophotonic composition. In some embodiments, the one or more gelling agents are present in an amount of 0.5-1% by weight of the biophotonic composition. In some embodiments, the one or more gelling agents are present in an amount of 1-20% by weight of the biophotonic composition. In some embodiments, the one or more gelling agents are present in an amount of 1-10% by weight of the biophotonic composition. In some embodiments, the one or more gelling agents are present in an amount of 1-5% by weight of the biophotonic composition. In some embodiments, the one or more gelling agents are present in an amount of 1-4% by weight of the biophotonic composition. In some embodiments, the one or more gelling agents are present in an amount of 1-3% by weight of the biophotonic composition. In some embodiments, the one or more gelling agents are present in an amount of 1-2% by weight of the biophotonic composition. In some embodiments, the one or more gelling agents are present in an amount of 1.5-2% by weight of the biophotonic composition. In some embodiments, the one or more gelling agents are present in an amount of 5-20% by weight of the biophotonic composition. In some embodiments, the one or more gelling agents are present in an amount of 10-20% by weight of the biophotonic composition. In some embodiments, the one or more gelling agents comprise are present in an amount of 15-20% by weight of the biophotonic composition. In some embodiments, the one or more gelling agents are present in an amount of 5-10% by weight of the biophotonic composition. In some embodiments, the one or more gelling agents are present in an amount of 1% by weight of the biophotonic composition. In some embodiments, the one or more gelling agents are present in an amount of 1.25% by weight of the biophotonic composition. In some embodiments, the one or more gelling agents are present in an amount of 1.5% by weight of the biophotonic composition. In some embodiments, the one or more gelling agents are present in an amount of 1.75% by weight of the biophotonic composition. In some embodiments, the one or more gelling agents are present in an amount of 2% by weight of the biophotonic composition. In some embodiments, the one or more gelling agents are present in an amount of 2.5% by weight of the biophotonic composition. In some embodiments, the one or more gelling agents are present in an amount of 3% by weight of the biophotonic composition.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

In some embodiments, the carbomer is present in an amount of about 0.01-10% by weight of the biophotonic composition. In some embodiments, the carbomer is present in an amount of about 0.01-5% by weight of the biophotonic composition. In some embodiments, the carbomer is present in an amount of about 0.01-2% by weight of the biophotonic composition. In some embodiments, the carbomer is present in an amount of about 0.01-1% by weight of the biophotonic composition. In some embodiments, the carbomer is present in an amount of about 0.05-10% by weight of the biophotonic composition. In some embodiments, the carbomer is present in an amount of about 0.05-5% by weight of the biophotonic composition. In some embodiments, the carbomer is present in an amount of about 0.05-2% by weight of the biophotonic composition. In some embodiments, the carbomer is present in an amount of about 0.05-1% by weight of the biophotonic composition. In some embodiments, the carbomer is present in an amount of about 0.1-10% by weight of the biophotonic composition. In some embodiments, the carbomer is present in an amount of about 0.1-5% by weight of the biophotonic composition. In some embodiments, the carbomer is present in an amount of about 0.1-2% by weight of the biophotonic composition. In some embodiments, the carbomer is present in an amount of about 0.1-1% by weight of the biophotonic composition. In some embodiments, the carbomer is present in an amount of about 0.5-10% by weight of the biophotonic composition. In some embodiments, the carbomer is present in an amount of about 0.5-5% by weight of the biophotonic composition. In some embodiments, the carbomer is present in an amount of about 0.5-2% by weight of the biophotonic composition. In some embodiments, the carbomer is present in an amount of about 0.5-1% by weight of the biophotonic composition. In some embodiments, the carbomer is present in an amount of about 1-5% by weight of the biophotonic composition. In some embodiments, the carbomer is present in an amount of about 1-4% by weight of the biophotonic composition. In some embodiments, the carbomer is present in an amount of about 1-3% by weight of the biophotonic composition. In some embodiments, the carbomer is present in an amount of about 1-2% by weight of the biophotonic composition. In some embodiments, the carbomer is present in an amount of about 1.5-2% by weight of the biophotonic composition. In some embodiments, the carbomer is present in an amount of about 1% by weight of the biophotonic composition. In some embodiments, the carbomer is present in an amount of about 1.25% by weight of the biophotonic composition. In some embodiments, the carbomer is present in an amount of about 1.5% by weight of the biophotonic composition. In some embodiments, the carbomer is present in an amount of about 1.75% by weight of the biophotonic composition. In some embodiments, the carbomer is present in an amount of about 2% by weight of the biophotonic composition. In some embodiments, the carbomer is present in an amount of about 2.5% by weight of the biophotonic composition. In some embodiments, the carbomer is present in an amount of about 3% by weight of the biophotonic composition.

In some embodiments, the carbomer is present in an amount of 0.01-10% by weight of the biophotonic composition. In some embodiments, the carbomer is present in an amount of 0.01-5% by weight of the biophotonic composition. In some embodiments, the carbomer is present in an amount of 0.01-2% by weight of the biophotonic composition. In some embodiments, the carbomer is present in an amount of 0.01-1% by weight of the biophotonic composition. In some embodiments, the carbomer is present in an amount of 0.05-10% by weight of the biophotonic composition. In some embodiments, the carbomer is present in an amount of 0.05-5% by weight of the biophotonic composition. In some embodiments, the carbomer is present in an amount of 0.05-2% by weight of the biophotonic composition. In some embodiments, the carbomer is present in an amount of 0.05-1% by weight of the biophotonic composition. In some embodiments, the carbomer is present in an amount of 0.1-10% by weight of the biophotonic composition. In some embodiments, the carbomer is present in an amount of 0.1-5% by weight of the biophotonic composition. In some embodiments, the carbomer is present in an amount of 0.1-2% by weight of the biophotonic composition. In some embodiments, the carbomer is present in an amount of 0.1-1% by weight of the biophotonic composition. In some embodiments, the carbomer is present in an amount of 0.5-10% by weight of the biophotonic composition. In some embodiments, the carbomer is present in an amount of 0.5-5% by weight of the biophotonic composition. In some embodiments, the carbomer is present in an amount of 0.5-2% by weight of the biophotonic composition. In some embodiments, the carbomer is present in an amount of 0.5-1% by weight of the biophotonic composition. In some embodiments, the carbomer is present in an amount of 1-5% by weight of the biophotonic composition. In some embodiments, the carbomer is present in an amount of 1-4% by weight of the biophotonic composition. In some embodiments, the carbomer is present in an amount of 1-3% by weight of the biophotonic composition. In some embodiments, the carbomer is present in an amount of 1-2% by weight of the biophotonic composition. In some embodiments, the carbomer is present in an amount of 1.5-2% by weight of the biophotonic composition. In some embodiments, the carbomer is present in an amount of 1% by weight of the biophotonic composition. In some embodiments, the carbomer is present in an amount of 1.25% by weight of the biophotonic composition. In some embodiments, the carbomer is present in an amount of 1.5% by weight of the biophotonic composition. In some embodiments, the carbomer is present in an amount of 1.75% by weight of the biophotonic composition. In some embodiments, the carbomer is present in an amount of 2% by weight of the biophotonic composition. In some embodiments, the carbomer is present in an amount of 2.5% by weight of the biophotonic composition. In some embodiments, the carbomer is present in an amount of 3% by weight of the biophotonic composition.

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments, the carbomer is Carbopol. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp) 8:S-135 (1991)), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In some embodiments, the carbomer is Carbopol® 980 NF, ETD 2020 NF, Ultrez 10 NF, Ultrez 21 or 1382 Polymer, 1342 NF, 940 NF. For example, about 0.05 to 10%, about 0.5 to 5%, or about 1 to 3% by weight of the final composition of a high molecular weight carbopol can be present as the gelling agent. In some embodiments, the biophotonic composition of the disclosure comprises 0.05 to 10%, about 0.5 to 5%, or about 1 to 3% by weight of the final composition of a high molecular weight carbopol.

In some embodiments, the high molecular weight carbopol is present in an amount of less than about 1.5% by weight of the total composition. In some embodiments, the high molecular weight carbopol is present in an amount of about 1.5-3% by weight of the total composition. In some embodiments, the high molecular weight carbopol is present in an amount of about 1.5-2.5% by weight of the total composition. In some embodiments, the high molecular weight carbopol is present in an amount of about 1.5-2% by weight of the total composition. In some embodiments, the high molecular weight carbopol is present in an amount of about 1% by weight of the total composition. In some embodiments, the high molecular weight carbopol is present in an amount of about 1.25% by weight of the total composition. In some embodiments, the high molecular weight carbopol is present in an amount of about 1.5% by weight of the total composition. In some embodiments, the high molecular weight carbopol is present in an amount of about 1.75% by weight of the total composition. In some embodiments, the high molecular weight carbopol is present in an amount of about 2% by weight of the total composition. In some embodiments, the high molecular weight carbopol is present in an amount of about 2.5% by weight of the total composition. In some embodiments, the high molecular weight carbopol is present in an amount of about 3% by weight of the total composition.

In some embodiments, the high molecular weight carbopol is present in an amount of less than 1.5% by weight of the total composition. In some embodiments, the high molecular weight carbopol is present in an amount of 1.5-3% by weight of the total composition. In some embodiments, the high molecular weight carbopol is present in an amount of 1.5-2.5% by weight of the total composition. In some embodiments, the high molecular weight carbopol is present in an amount of 1.5-2% by weight of the total composition. In some embodiments, the high molecular weight carbopol is present in an amount of 1% by weight of the total composition. In some embodiments, the high molecular weight carbopol is present in an amount of 1.25% by weight of the total composition. In some embodiments, the high molecular weight carbopol is present in an amount of 1.5% by weight of the total composition. In some embodiments, the high molecular weight carbopol is present in an amount of 1.75% by weight of the total composition. In some embodiments, the high molecular weight carbopol is present in an amount of 2% by weight of the total composition. In some embodiments, the high molecular weight carbopol is present in an amount of 2.5% by weight of the total composition. In some embodiments, the high molecular weight carbopol is present in an amount of 3% by weight of the total composition.

In some embodiments, the gelling agent comprises a hygroscopic and/or a hydrophilic material useful for their water attracting properties. The hygroscopic or hydrophilic material may include, but is not limited to, glucosamine, glucosamine sulfate, polysaccharides, cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like), glycosaminoglycan, poly(vinyl alcohol), poly(2-hydroxy-ethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate).

The gelling agent may be protein-based/naturally derived material such as sodium hyaluronate, gelatin or collagen, lipids, or the like. The gelling agent may be a polysaccharide such as starch, chitosan, chitin, agarose, agar, locust bean gum, carrageenan, gellan gum, pectin, alginate, xanthan, guar gum, and the like.

In some embodiments, the composition can include up to about 2% by weight of the final composition of sodium hyaluronate as the single gelling agent. In some embodiments, the composition can include more than about 4%, more than about 5%, by weight of the final composition of gelatin as the single gelling agent. In some embodiments, the composition can include up to about 10%, up to about 8%, starch as the single gelling agent. In some embodiments, the composition can include more than about 5%, more than about 10%, by weight of the final composition of collagen as the gelling agent. In some embodiments, about 0.1 to about 10%, or about 0.5 to about 3%, by weight of the final composition of chitin can be used as the gelling agent. In some embodiments, about 0.5% to about 5% by weight of the final composition of corn starch, or about 5 to about 10% by weight of the final composition of starch can be used as the gelling agent. In some embodiments, more than about 2.5 wt % by weight of the final composition of alginate can be used in the composition as the gelling agent. In some embodiments, the percentages by weight percent of the final composition of the gelling agents can be as follows: cellulose gel (about 0.3 to about 2.0%), konjac gum (about 0.5 to about 0.7%), carrageenan gum (about 0.02 to about 2.0%), xanthan gum (about 0.01 to about 2.0%), acacia gum (about 3 to about 30%), agar (about 0.04 to about 1.2%), guar gum (about 0.1 to about 1%), locust bean gum (about 0.15 to about 0.75%), pectin (about 0.1 to about 0.6%), tara gum (about 0.1 to about 1.0%), polyvinylypyrrolidone (about 1 to about 5%), sodium polyacrylate (about 1 to about 10%). Other gelling agents can be used in amounts sufficient to gel the composition or to sufficiently thicken the composition. It will be appreciated that lower amounts of the above gelling agents may be used in the presence of another gelling agent or a thickener.

The biophotonic composition of the present disclosure may be further encapsulated, e.g., in a membrane. Such a membrane may be transparent, and/or substantially, or fully impermeable. The membrane may be impermeable to liquid but permeable to gases such as air. In some embodiments, the composition may form a membrane that encapsulates the chromophore(s) of the biophotonic topical composition, where the membrane may be substantially impermeable to liquid and/or gas. The membrane may be formed of one or more lipidic agents, polymers, gelatin, cellulose or cyclodextrins, or the like. In some embodiments, the membrane is translucent or transparent to allow light to infiltrate to and from the chromophore(s). In some embodiments, the composition is a dendrimer with an outer membrane comprising poly(propylene amine). In some embodiments, the outer membrane comprises gelatin.

(c) Carbonate and Bicarbonate Salts

In some embodiments, the compositions of the present disclosure may optionally further comprise one or more carbonate or bicarbonate salts.

Suitable carbonate or bicarbonate salts that may be present in the composition include, but are not limited to: ammonium bicarbonate, caesium bicarbonate, potassium bicarbonate, sodium bicarbonate, choline bicarbonate, aminoguanidine bicarbonate, tetraethylammonium bicarbonate, barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, or zinc carbonate.

In some embodiments, the biophotonic composition of the disclosure comprises one or more salts selected from bicarbonate salts, carbonate salts or a combination of the foregoing salts. In some embodiments, the biophotonic composition of the disclosure comprises one or more bicarbonate salts. In some embodiments when the biophotonic composition comprises one or more bicarbonate salts, the bicarbonate salt is sodium bicarbonate. In some embodiments when the biophotonic composition comprises one or more bicarbonate salts, the bicarbonate salt is potassium bicarbonate. In some embodiments, the biophotonic composition of the disclosure comprises one or more carbonate salts. In some embodiments when the biophotonic composition comprises one or more carbonate salts, the carbonate salt is sodium carbonate. In some embodiments when the biophotonic composition comprises one or more carbonate salts, the carbonate salt is potassium carbonate. In some embodiments when the biophotonic composition comprises one or more carbonate salts, the carbonate salt is calcium carbonate.

In some embodiments, the one or more salts selected from bicarbonate salts, carbonate salts or a combination of the foregoing salts are present in an amount of about 0.01-30% by weight of the total composition. In some embodiments, the one or more salts selected from bicarbonate salts, carbonate salts or a combination of the foregoing salts are present in an amount of about 0.01-20% by weight of the total composition. In some embodiments, the one or more salts selected from bicarbonate salts, carbonate salts or a combination of the foregoing salts are present in an amount of about 0.01-10% by weight of the total composition. In some embodiments, the one or more salts selected from bicarbonate salts, carbonate salts or a combination of the foregoing salts are present in an amount of about 0.01-5% by weight of the total composition. In some embodiments, the one or more salts selected from bicarbonate salts, carbonate salts or a combination of the foregoing salts are present in an amount of about 0.05-30% by weight of the total composition. In some embodiments, the one or more salts selected from bicarbonate salts, carbonate salts or a combination of the foregoing salts are present in an amount of about 0.05-20% by weight of the total composition. In some embodiments, the one or more salts selected from bicarbonate salts, carbonate salts or a combination of the foregoing salts are present in an amount of about 0.05-10% by weight of the total composition. In some embodiments, the one or more salts selected from bicarbonate salts, carbonate salts or a combination of the foregoing salts are present in an amount of about 0.05-5% by weight of the total composition. In some embodiments, the one or more salts selected from bicarbonate salts, carbonate salts or a combination of the foregoing salts are present in an amount of about 0.1-30% by weight of the total composition. In some embodiments, the one or more salts selected from bicarbonate salts, carbonate salts or a combination of the foregoing salts are present in an amount of about 0.1-20% by weight of the total composition. In some embodiments, the one or more salts selected from bicarbonate salts, carbonate salts or a combination of the foregoing salts are present in an amount of about 0.1-10% by weight of the total composition. In some embodiments, the one or more salts selected from bicarbonate salts, carbonate salts or a combination of the foregoing salts are present in an amount of about 0.1-5% by weight of the total composition. In some embodiments, the one or more salts selected from bicarbonate salts, carbonate salts or a combination of the foregoing salts are present in an amount of about 0.5-30% by weight of the total composition. In some embodiments, the one or more salts selected from bicarbonate salts, carbonate salts or a combination of the foregoing salts are present in an amount of about 0.5-20% by weight of the total composition. In some embodiments, the one or more salts selected from bicarbonate salts, carbonate salts or a combination of the foregoing salts are present in an amount of about 0.5-10% by weight of the total composition. In some embodiments, the one or more salts selected from bicarbonate salts, carbonate salts or a combination of the foregoing salts are present in an amount of about 0.5-5% by weight of the total composition. In some embodiments, the one or more salts selected from bicarbonate salts, carbonate salts or a combination of the foregoing salts are present in an amount of about 1-30% by weight of the total composition. In some embodiments, the one or more salts selected from bicarbonate salts, carbonate salts or a combination of the foregoing salts are present in an amount of about 1-20% by weight of the total composition. In some embodiments, the one or more salts selected from bicarbonate salts, carbonate salts or a combination of the foregoing salts are present in an amount of about 1-10% by weight of the total composition. In some embodiments, the one or more salts selected from bicarbonate salts, carbonate salts or a combination of the foregoing salts are present in an amount of about 5-30% by weight of the total composition. In some embodiments, the one or more salts selected from bicarbonate salts, carbonate salts or a combination of the foregoing salts are present in an amount of about 5-20% by weight of the total composition. In some embodiments, the one or more salts selected from bicarbonate salts, carbonate salts or a combination of the foregoing salts are present in an amount of about 5-10% by weight of the total composition. In some embodiments, the one or more salts selected from bicarbonate salts, carbonate salts or a combination of the foregoing salts are present in an amount of about 10-30% by weight of the total composition. In some embodiments, the one or more salts selected from bicarbonate salts, carbonate salts or a combination of the foregoing salts are present in an amount of about 10-20% by weight of the total composition. In some embodiments, the one or more salts selected from bicarbonate salts, carbonate salts or a combination of the foregoing salts are present in an amount of about 20-30% by weight of the total composition. In some embodiments, the one or more salts selected from bicarbonate salts, carbonate salts or a combination of the foregoing salts are present in an amount of about 1-5% by weight of the total composition. In some embodiments, the one or more salts selected from bicarbonate salts, carbonate salts or a combination of the foregoing salts are present in an amount of about 0.1% by weight of the total composition. In some embodiments, the one or more salts selected from bicarbonate salts, carbonate salts or a combination of the foregoing salts are present in an amount of about 0.2% by weight of the total composition. In some embodiments, the one or more salts selected from bicarbonate salts, carbonate salts or a combination of the foregoing salts are present in an amount of about 0.3% by weight of the total composition. In some embodiments, the one or more salts selected from bicarbonate salts, carbonate salts or a combination of the foregoing salts are present in an amount of about 0.4% by weight of the total composition. In some embodiments, the one or more salts selected from bicarbonate salts, carbonate salts or a combination of the foregoing salts are present in an amount of about 0.5% by weight of the total composition. In some embodiments, the one or more salts selected from bicarbonate salts, carbonate salts or a combination of the foregoing salts are present in an amount of about 1% by weight of the total composition. In some embodiments, the one or more salts selected from bicarbonate salts, carbonate salts or a combination of the foregoing salts are present in an amount of about 1.5% by weight of the total composition. In some embodiments, the one or more salts selected from bicarbonate salts, carbonate salts or a combination of the foregoing salts are present in an amount of about 2% by weight of the total composition. In some embodiments, the one or more salts selected from bicarbonate salts, carbonate salts or a combination of the foregoing salts are present in an amount of about 2.5% by weight of the total composition. In some embodiments, the one or more salts selected from bicarbonate salts, carbonate salts or a combination of the foregoing salts are present in an amount of about 3% by weight of the total composition. In some embodiments, the one or more salts selected from bicarbonate salts, carbonate salts or a combination of the foregoing salts are present in an amount of about 3.5% by weight of the total composition. In some embodiments, the one or more salts selected from bicarbonate salts, carbonate salts or a combination of the foregoing salts are present in an amount of about 4% by weight of the total composition. In some embodiments, the one or more salts selected from bicarbonate salts, carbonate salts or a combination of the foregoing salts are present in an amount of about 4.5% by weight of the total composition. In some embodiments, the one or more salts selected from bicarbonate salts, carbonate salts or a combination of the foregoing salts are present in an amount of about 5% by weight of the total composition. In some embodiments, the one or more salts selected from bicarbonate salts, carbonate salts or a combination of the foregoing salts are present in an amount of about 5.5% by weight of the total composition. In some embodiments, the one or more salts selected from bicarbonate salts, carbonate salts or a combination of the foregoing salts are present in an amount of about 6% by weight of the total composition. In some embodiments, the one or more salts selected from bicarbonate salts, carbonate salts or a combination of the foregoing salts are present in an amount of about 6.5% by weight of the total composition. In some embodiments, the one or more salts selected from bicarbonate salts, carbonate salts or a combination of the foregoing salts are present in an amount of about 7% by weight of the total composition. In some embodiments, the one or more salts selected from bicarbonate salts, carbonate salts or a combination of the foregoing salts are present in an amount of about 7.5% by weight of the total composition. In some embodiments, the one or more salts selected from bicarbonate salts, carbonate salts or a combination of the foregoing salts are present in an amount of about 8% by weight of the total composition. In some embodiments, the one or more salts selected from bicarbonate salts, carbonate salts or a combination of the foregoing salts are present in an amount of about 8.5% by weight of the total composition. In some embodiments, the one or more salts selected from bicarbonate salts, carbonate salts or a combination of the foregoing salts are present in an amount of about 9% by weight of the total composition. In some embodiments, the one or more salts selected from bicarbonate salts, carbonate salts or a combination of the foregoing salts are present in an amount of about 9.5% by weight of the total composition. In some embodiments, the one or more salts selected from bicarbonate salts, carbonate salts or a combination of the foregoing salts are present in an amount of about 10% by weight of the total composition. In some embodiments, the one or more salts selected from bicarbonate salts, carbonate salts or a combination of the foregoing salts are present in an amount of about 12.5% by weight of the total composition. In some embodiments, the one or more salts selected from bicarbonate salts, carbonate salts or a combination of the foregoing salts are present in an amount of about 15% by weight of the total composition. In some embodiments, the one or more salts selected from bicarbonate salts, carbonate salts or a combination of the foregoing salts are present in an amount of about 17.5% by weight of the total composition. In some embodiments, the one or more salts selected from bicarbonate salts, carbonate salts or a combination of the foregoing salts are present in an amount of about 20% by weight of the total composition.

In some embodiments, the one or more salts selected from bicarbonate salts, carbonate salts or a combination of the foregoing salts are present in an amount of 0.01-30% by weight of the total composition. In some embodiments, the one or more salts selected from bicarbonate salts, carbonate salts or a combination of the foregoing salts are present in an amount of 0.01-20% by weight of the total composition. In some embodiments, the one or more salts selected from bicarbonate salts, carbonate salts or a combination of the foregoing salts are present in an amount of 0.01-10% by weight of the total composition. In some embodiments, the one or more salts selected from bicarbonate salts, carbonate salts or a combination of the foregoing salts are present in an amount of 0.01-5% by weight of the total composition. In some embodiments, the one or more salts selected from bicarbonate salts, carbonate salts or a combination of the foregoing salts are present in an amount of 0.05-30% by weight of the total composition. In some embodiments, the one or more salts selected from bicarbonate salts, carbonate salts or a combination of the foregoing salts are present in an amount of 0.05-20% by weight of the total composition. In some embodiments, the one or more salts selected from bicarbonate salts, carbonate salts or a combination of the foregoing salts are present in an amount of 0.05-10% by weight of the total composition. In some embodiments, the one or more salts selected from bicarbonate salts, carbonate salts or a combination of the foregoing salts are present in an amount of 0.05-5% by weight of the total composition. In some embodiments, the one or more salts selected from bicarbonate salts, carbonate salts or a combination of the foregoing salts are present in an amount of 0.1-30% by weight of the total composition. In some embodiments, the one or more salts selected from bicarbonate salts, carbonate salts or a combination of the foregoing salts are present in an amount of 0.1-20% by weight of the total composition. In some embodiments, the one or more salts selected from bicarbonate salts, carbonate salts or a combination of the foregoing salts are present in an amount of 0.1-10% by weight of the total composition. In some embodiments, the one or more salts selected from bicarbonate salts, carbonate salts or a combination of the foregoing salts are present in an amount of 0.1-5% by weight of the total composition. In some embodiments, the one or more salts selected from bicarbonate salts, carbonate salts or a combination of the foregoing salts are present in an amount of 0.5-30% by weight of the total composition. In some embodiments, the one or more salts selected from bicarbonate salts, carbonate salts or a combination of the foregoing salts are present in an amount of 0.5-20% by weight of the total composition. In some embodiments, the one or more salts selected from bicarbonate salts, carbonate salts or a combination of the foregoing salts are present in an amount of 0.5-10% by weight of the total composition. In some embodiments, the one or more salts selected from bicarbonate salts, carbonate salts or a combination of the foregoing salts are present in an amount of 0.5-5% by weight of the total composition. In some embodiments, the one or more salts selected from bicarbonate salts, carbonate salts or a combination of the foregoing salts are present in an amount of 1-30% by weight of the total composition. In some embodiments, the one or more salts selected from bicarbonate salts, carbonate salts or a combination of the foregoing salts are present in an amount of 1-20% by weight of the total composition. In some embodiments, the one or more salts selected from bicarbonate salts, carbonate salts or a combination of the foregoing salts are present in an amount of 1-10% by weight of the total composition. In some embodiments, the one or more salts selected from bicarbonate salts, carbonate salts or a combination of the foregoing salts are present in an amount of 5-30% by weight of the total composition. In some embodiments, the one or more salts selected from bicarbonate salts, carbonate salts or a combination of the foregoing salts are present in an amount of 5-20% by weight of the total composition. In some embodiments, the one or more salts selected from bicarbonate salts, carbonate salts or a combination of the foregoing salts are present in an amount of 5-10% by weight of the total composition. In some embodiments, the one or more salts selected from bicarbonate salts, carbonate salts or a combination of the foregoing salts are present in an amount of 10-30% by weight of the total composition. In some embodiments, the one or more salts selected from bicarbonate salts, carbonate salts or a combination of the foregoing salts are present in an amount of 10-20% by weight of the total composition. In some embodiments, the one or more salts selected from bicarbonate salts, carbonate salts or a combination of the foregoing salts are present in an amount of 20-30% by weight of the total composition. In some embodiments, the one or more salts selected from bicarbonate salts, carbonate salts or a combination of the foregoing salts are present in an amount of 1-5% by weight of the total composition. In some embodiments, the one or more salts selected from bicarbonate salts, carbonate salts or a combination of the foregoing salts are present in an amount of 0.1% by weight of the total composition. In some embodiments, the one or more salts selected from bicarbonate salts, carbonate salts or a combination of the foregoing salts are present in an amount of 0.2% by weight of the total composition. In some embodiments, the one or more salts selected from bicarbonate salts, carbonate salts or a combination of the foregoing salts are present in an amount of 0.3% by weight of the total composition. In some embodiments, the one or more salts selected from bicarbonate salts, carbonate salts or a combination of the foregoing salts are present in an amount of 0.4% by weight of the total composition. In some embodiments, the one or more salts selected from bicarbonate salts, carbonate salts or a combination of the foregoing salts are present in an amount of 0.5% by weight of the total composition. In some embodiments, the one or more salts selected from bicarbonate salts, carbonate salts or a combination of the foregoing salts are present in an amount of 1% by weight of the total composition. In some embodiments, the one or more salts selected from bicarbonate salts, carbonate salts or a combination of the foregoing salts are present in an amount of 1.5% by weight of the total composition. In some embodiments, the one or more salts selected from bicarbonate salts, carbonate salts or a combination of the foregoing salts are present in an amount of 2% by weight of the total composition. In some embodiments, the one or more salts selected from bicarbonate salts, carbonate salts or a combination of the foregoing salts are present in an amount of 2.5% by weight of the total composition. In some embodiments, the one or more salts selected from bicarbonate salts, carbonate salts or a combination of the foregoing salts are present in an amount of 3% by weight of the total composition. In some embodiments, the one or more salts selected from bicarbonate salts, carbonate salts or a combination of the foregoing salts are present in an amount of 3.5% by weight of the total composition. In some embodiments, the one or more salts selected from bicarbonate salts, carbonate salts or a combination of the foregoing salts are present in an amount of 4% by weight of the total composition. In some embodiments, the one or more salts selected from bicarbonate salts, carbonate salts or a combination of the foregoing salts are present in an amount of 4.5% by weight of the total composition. In some embodiments, the one or more salts selected from bicarbonate salts, carbonate salts or a combination of the foregoing salts are present in an amount of 5% by weight of the total composition. In some embodiments, the one or more salts selected from bicarbonate salts, carbonate salts or a combination of the foregoing salts are present in an amount of 5.5% by weight of the total composition. In some embodiments, the one or more salts selected from bicarbonate salts, carbonate salts or a combination of the foregoing salts are present in an amount of 6% by weight of the total composition. In some embodiments, the one or more salts selected from bicarbonate salts, carbonate salts or a combination of the foregoing salts are present in an amount of 6.5% by weight of the total composition. In some embodiments, the one or more salts selected from bicarbonate salts, carbonate salts or a combination of the foregoing salts are present in an amount of 7% by weight of the total composition. In some embodiments, the one or more salts selected from bicarbonate salts, carbonate salts or a combination of the foregoing salts are present in an amount of 7.5% by weight of the total composition. In some embodiments, the one or more salts selected from bicarbonate salts, carbonate salts or a combination of the foregoing salts are present in an amount of 8% by weight of the total composition. In some embodiments, the one or more salts selected from bicarbonate salts, carbonate salts or a combination of the foregoing salts are present in an amount of 8.5% by weight of the total composition. In some embodiments, the one or more salts selected from bicarbonate salts, carbonate salts or a combination of the foregoing salts are present in an amount of 9% by weight of the total composition. In some embodiments, the one or more salts selected from bicarbonate salts, carbonate salts or a combination of the foregoing salts are present in an amount of 9.5% by weight of the total composition. In some embodiments, the one or more salts selected from bicarbonate salts, carbonate salts or a combination of the foregoing salts are present in an amount of 10% by weight of the total composition. In some embodiments, the one or more salts selected from bicarbonate salts, carbonate salts or a combination of the foregoing salts are present in an amount of 12.5% by weight of the total composition. In some embodiments, the one or more salts selected from bicarbonate salts, carbonate salts or a combination of the foregoing salts are present in an amount of 15% by weight of the total composition. In some embodiments, the one or more salts selected from bicarbonate salts, carbonate salts or a combination of the foregoing salts are present in an amount of 17.5% by weight of the total composition. In some embodiments, the one or more salts selected from bicarbonate salts, carbonate salts or a combination of the foregoing salts are present in an amount of 20% by weight of the total composition.

In some embodiments, one or more bicarbonate salts are present in an amount of about 0.01-30% by weight of the total composition. In some embodiments, one or more bicarbonate salts are present in an amount of about 0.01-20% by weight of the total composition. In some embodiments, one or more bicarbonate salts are present in an amount of about 0.01-10% by weight of the total composition. In some embodiments, one or more bicarbonate salts are present in an amount of about 0.01-5% by weight of the total composition. In some embodiments, one or more bicarbonate salts are present in an amount of about 0.05-30% by weight of the total composition. In some embodiments, one or more bicarbonate salts are present in an amount of about 0.05-20% by weight of the total composition. In some embodiments, one or more bicarbonate salts are present in an amount of about 0.05-10% by weight of the total composition. In some embodiments, one or more bicarbonate salts are present in an amount of about 0.05-5% by weight of the total composition. In some embodiments, one or more bicarbonate salts are present in an amount of about 0.1-30% by weight of the total composition. In some embodiments, one or more bicarbonate salts are present in an amount of about 0.1-20% by weight of the total composition. In some embodiments, one or more bicarbonate salts are present in an amount of about 0.1-10% by weight of the total composition. In some embodiments, one or more bicarbonate salts are present in an amount of about 0.1-5% by weight of the total composition. In some embodiments, one or more bicarbonate salts are present in an amount of about 0.5-30% by weight of the total composition. In some embodiments, one or more bicarbonate salts are present in an amount of about 0.5-20% by weight of the total composition. In some embodiments, one or more bicarbonate salts are present in an amount of about 0.5-10% by weight of the total composition. In some embodiments, one or more bicarbonate salts are present in an amount of about 0.5-5% by weight of the total composition. In some embodiments, one or more bicarbonate salts are present in an amount of about 1-30% by weight of the total composition. In some embodiments, one or more bicarbonate salts are present in an amount of about 1-20% by weight of the total composition. In some embodiments, one or more bicarbonate salts are present in an amount of about 1-10% by weight of the total composition. In some embodiments, one or more bicarbonate salts are present in an amount of about 5-30% by weight of the total composition. In some embodiments, one or more bicarbonate salts are present in an amount of about 5-20% by weight of the total composition. In some embodiments, one or more bicarbonate salts are present in an amount of about 5-10% by weight of the total composition. In some embodiments, one or more bicarbonate salts are present in an amount of about 10-30% by weight of the total composition. In some embodiments, one or more bicarbonate salts are present in an amount of about 10-20% by weight of the total composition. In some embodiments, one or more bicarbonate salts are present in an amount of about 20-30% by weight of the total composition. In some embodiments, one or more bicarbonate salts are present in an amount of about 1-5% by weight of the total composition. In some embodiments, one or more bicarbonate salts are present in an amount of about 0.1% by weight of the total composition. In some embodiments, one or more bicarbonate salts are present in an amount of about 0.2% by weight of the total composition. In some embodiments, one or more bicarbonate salts are present in an amount of about 0.3% by weight of the total composition. In some embodiments, one or more bicarbonate salts are present in an amount of about 0.4% by weight of the total composition. In some embodiments, one or more bicarbonate salts are present in an amount of about 0.5% by weight of the total composition. In some embodiments, one or more bicarbonate salts are present in an amount of about 1% by weight of the total composition. In some embodiments, one or more bicarbonate salts are present in an amount of about 1.5% by weight of the total composition. In some embodiments, one or more bicarbonate salts are present in an amount of about 2% by weight of the total composition. In some embodiments, one or more bicarbonate salts are present in an amount of about 2.5% by weight of the total composition. In some embodiments, one or more bicarbonate salts are present in an amount of about 3% by weight of the total composition. In some embodiments, one or more bicarbonate salts are present in an amount of about 3.5% by weight of the total composition. In some embodiments, one or more bicarbonate salts are present in an amount of about 4% by weight of the total composition. In some embodiments, one or more bicarbonate salts are present in an amount of about 4.5% by weight of the total composition. In some embodiments, one or more bicarbonate salts are present in an amount of about 5% by weight of the total composition. In some embodiments, one or more bicarbonate salts are present in an amount of about 5.5% by weight of the total composition. In some embodiments, one or more bicarbonate salts are present in an amount of about 6% by weight of the total composition. In some embodiments, one or more bicarbonate salts are present in an amount of about 6.5% by weight of the total composition. In some embodiments, one or more bicarbonate salts are present in an amount of about 7% by weight of the total composition. In some embodiments, one or more bicarbonate salts are present in an amount of about 7.5% by weight of the total composition. In some embodiments, one or more bicarbonate salts are present in an amount of about 8% by weight of the total composition. In some embodiments, one or more bicarbonate salts are present in an amount of about 8.5% by weight of the total composition. In some embodiments, one or more bicarbonate salts are present in an amount of about 9% by weight of the total composition. In some embodiments, one or more bicarbonate salts are present in an amount of about 9.5% by weight of the total composition. In some embodiments, one or more bicarbonate salts are present in an amount of about 10% by weight of the total composition. In some embodiments, one or more bicarbonate salts are present in an amount of about 12.5% by weight of the total composition. In some embodiments, one or more bicarbonate salts are present in an amount of about 15% by weight of the total composition. In some embodiments, one or more bicarbonate salts are present in an amount of about 17.5% by weight of the total composition. In some embodiments, one or more bicarbonate salts are present in an amount of about 20% by weight of the total composition.

In some embodiments, one or more bicarbonate salts are present in an amount of 0.01-30% by weight of the total composition. In some embodiments, one or more bicarbonate salts are present in an amount of 0.01-20% by weight of the total composition. In some embodiments, one or more bicarbonate salts are present in an amount of 0.01-10% by weight of the total composition. In some embodiments, one or more bicarbonate salts are present in an amount of 0.01-5% by weight of the total composition. In some embodiments, one or more bicarbonate salts are present in an amount of 0.05-30% by weight of the total composition. In some embodiments, one or more bicarbonate salts are present in an amount of 0.05-20% by weight of the total composition. In some embodiments, one or more bicarbonate salts are present in an amount of 0.05-10% by weight of the total composition. In some embodiments, one or more bicarbonate salts are present in an amount of 0.05-5% by weight of the total composition. In some embodiments, one or more bicarbonate salts are present in an amount of 0.1-30% by weight of the total composition. In some embodiments, one or more bicarbonate salts are present in an amount of 0.1-20% by weight of the total composition. In some embodiments, one or more bicarbonate salts are present in an amount of 0.1-10% by weight of the total composition. In some embodiments, one or more bicarbonate salts are present in an amount of 0.1-5% by weight of the total composition. In some embodiments, one or more bicarbonate salts are present in an amount of 0.5-30% by weight of the total composition. In some embodiments, one or more bicarbonate salts are present in an amount of 0.5-20% by weight of the total composition. In some embodiments, one or more bicarbonate salts are present in an amount of 0.5-10% by weight of the total composition. In some embodiments, one or more bicarbonate salts are present in an amount of 0.5-5% by weight of the total composition. In some embodiments, one or more bicarbonate salts are present in an amount of 1-30% by weight of the total composition. In some embodiments, one or more bicarbonate salts are present in an amount of 1-20% by weight of the total composition. In some embodiments, one or more bicarbonate salts are present in an amount of 1-10% by weight of the total composition. In some embodiments, one or more bicarbonate salts are present in an amount of 5-30% by weight of the total composition. In some embodiments, one or more bicarbonate salts are present in an amount of 5-20% by weight of the total composition. In some embodiments, one or more bicarbonate salts are present in an amount of 5-10% by weight of the total composition. In some embodiments, one or more bicarbonate salts are present in an amount of 10-30% by weight of the total composition. In some embodiments, one or more bicarbonate salts are present in an amount of 10-20% by weight of the total composition. In some embodiments, one or more bicarbonate salts are present in an amount of 20-30% by weight of the total composition. In some embodiments, one or more bicarbonate salts are present in an amount of 1-5% by weight of the total composition. In some embodiments, one or more bicarbonate salts are present in an amount of 0.1% by weight of the total composition. In some embodiments, one or more bicarbonate salts are present in an amount of 0.2% by weight of the total composition. In some embodiments, one or more bicarbonate salts are present in an amount of 0.3% by weight of the total composition. In some embodiments, one or more bicarbonate salts are present in an amount of 0.4% by weight of the total composition. In some embodiments, one or more bicarbonate salts are present in an amount of 0.5% by weight of the total composition. In some embodiments, one or more bicarbonate salts are present in an amount of 1% by weight of the total composition. In some embodiments, one or more bicarbonate salts are present in an amount of 1.5% by weight of the total composition. In some embodiments, one or more bicarbonate salts are present in an amount of 2% by weight of the total composition. In some embodiments, one or more bicarbonate salts are present in an amount of 2.5% by weight of the total composition. In some embodiments, one or more bicarbonate salts are present in an amount of 3% by weight of the total composition. In some embodiments, one or more bicarbonate salts are present in an amount of 3.5% by weight of the total composition. In some embodiments, one or more bicarbonate salts are present in an amount of 4% by weight of the total composition. In some embodiments, one or more bicarbonate salts are present in an amount of 4.5% by weight of the total composition. In some embodiments, one or more bicarbonate salts are present in an amount of 5% by weight of the total composition. In some embodiments, one or more bicarbonate salts are present in an amount of 5.5% by weight of the total composition. In some embodiments, one or more bicarbonate salts are present in an amount of 6% by weight of the total composition. In some embodiments, one or more bicarbonate salts are present in an amount of 6.5% by weight of the total composition. In some embodiments, one or more bicarbonate salts are present in an amount of 7% by weight of the total composition. In some embodiments, one or more bicarbonate salts are present in an amount of 7.5% by weight of the total composition. In some embodiments, one or more bicarbonate salts are present in an amount of 8% by weight of the total composition. In some embodiments, one or more bicarbonate salts are present in an amount of 8.5% by weight of the total composition. In some embodiments, one or more bicarbonate salts are present in an amount of 9% by weight of the total composition. In some embodiments, one or more bicarbonate salts are present in an amount of 9.5% by weight of the total composition. In some embodiments, one or more bicarbonate salts are present in an amount of 10% by weight of the total composition. In some embodiments, one or more bicarbonate salts are present in an amount of 12.5% by weight of the total composition. In some embodiments, one or more bicarbonate salts are present in an amount of 15% by weight of the total composition. In some embodiments, one or more bicarbonate salts are present in an amount of 17.5% by weight of the total composition. In some embodiments, one or more bicarbonate salts are present in an amount of 20% by weight of the total composition.

In some embodiments, one or more carbonate salts are present in an amount of about 0.01-30% by weight of the total composition. In some embodiments, one or more carbonate salts are present in an amount of about 0.01-20% by weight of the total composition. In some embodiments, one or more carbonate salts are present in an amount of about 0.01-10% by weight of the total composition. In some embodiments, one or more carbonate salts are present in an amount of about 0.01-5% by weight of the total composition. In some embodiments, one or more carbonate salts are present in an amount of about 0.05-30% by weight of the total composition. In some embodiments, one or more carbonate salts are present in an amount of about 0.05-20% by weight of the total composition. In some embodiments, one or more carbonate salts are present in an amount of about 0.05-10% by weight of the total composition. In some embodiments, one or more carbonate salts are present in an amount of about 0.05-5% by weight of the total composition. In some embodiments, one or more carbonate salts are present in an amount of about 0.1-30% by weight of the total composition. In some embodiments, one or more carbonate salts are present in an amount of about 0.1-20% by weight of the total composition. In some embodiments, one or more carbonate salts are present in an amount of about 0.1-10% by weight of the total composition. In some embodiments, one or more carbonate salts are present in an amount of about 0.1-5% by weight of the total composition. In some embodiments, one or more carbonate salts are present in an amount of about 0.5-30% by weight of the total composition. In some embodiments, one or more carbonate salts are present in an amount of about 0.5-20% by weight of the total composition. In some embodiments, one or more carbonate salts are present in an amount of about 0.5-10% by weight of the total composition. In some embodiments, one or more carbonate salts are present in an amount of about 0.5-5% by weight of the total composition. In some embodiments, one or more carbonate salts are present in an amount of about 1-30% by weight of the total composition. In some embodiments, one or more carbonate salts are present in an amount of about 1-20% by weight of the total composition. In some embodiments, one or more carbonate salts are present in an amount of about 1-10% by weight of the total composition. In some embodiments, one or more carbonate salts are present in an amount of about 5-30% by weight of the total composition. In some embodiments, one or more carbonate salts are present in an amount of about 5-20% by weight of the total composition. In some embodiments, one or more carbonate salts are present in an amount of about 5-10% by weight of the total composition. In some embodiments, one or more carbonate salts are present in an amount of about 10-30% by weight of the total composition. In some embodiments, one or more carbonate salts are present in an amount of about 10-20% by weight of the total composition. In some embodiments, one or more carbonate salts are present in an amount of about 20-30% by weight of the total composition. In some embodiments, one or more carbonate salts are present in an amount of about 1-5% by weight of the total composition. In some embodiments, one or more carbonate salts are present in an amount of about 0.1% by weight of the total composition. In some embodiments, one or more carbonate salts are present in an amount of about 0.2% by weight of the total composition. In some embodiments, one or more carbonate salts are present in an amount of about 0.3% by weight of the total composition. In some embodiments, one or more carbonate salts are present in an amount of about 0.4% by weight of the total composition. In some embodiments, one or more carbonate salts are present in an amount of about 0.5% by weight of the total composition. In some embodiments, one or more carbonate salts are present in an amount of about 1% by weight of the total composition. In some embodiments, one or more carbonate salts are present in an amount of about 1.5% by weight of the total composition. In some embodiments, one or more carbonate salts are present in an amount of about 2% by weight of the total composition. In some embodiments, one or more carbonate salts are present in an amount of about 2.5% by weight of the total composition. In some embodiments, one or more carbonate salts are present in an amount of about 3% by weight of the total composition. In some embodiments, one or more carbonate salts are present in an amount of about 3.5% by weight of the total composition. In some embodiments, one or more carbonate salts are present in an amount of about 4% by weight of the total composition. In some embodiments, one or more carbonate salts are present in an amount of about 4.5% by weight of the total composition. In some embodiments, one or more carbonate salts are present in an amount of about 5% by weight of the total composition. In some embodiments, one or more carbonate salts are present in an amount of about 5.5% by weight of the total composition. In some embodiments, one or more carbonate salts are present in an amount of about 6% by weight of the total composition. In some embodiments, one or more carbonate salts are present in an amount of about 6.5% by weight of the total composition. In some embodiments, one or more carbonate salts are present in an amount of about 7% by weight of the total composition. In some embodiments, one or more carbonate salts are present in an amount of about 7.5% by weight of the total composition. In some embodiments, one or more carbonate salts are present in an amount of about 8% by weight of the total composition. In some embodiments, one or more carbonate salts are present in an amount of about 8.5% by weight of the total composition. In some embodiments, one or more carbonate salts are present in an amount of about 9% by weight of the total composition. In some embodiments, one or more carbonate salts are present in an amount of about 9.5% by weight of the total composition. In some embodiments, one or more carbonate salts are present in an amount of about 10% by weight of the total composition. In some embodiments, one or more carbonate salts are present in an amount of about 12.5% by weight of the total composition. In some embodiments, one or more carbonate salts are present in an amount of about 15% by weight of the total composition. In some embodiments, one or more carbonate salts are present in an amount of about 17.5% by weight of the total composition. In some embodiments, one or more carbonate salts are present in an amount of about 20% by weight of the total composition.

In some embodiments, one or more carbonate salts are present in an amount of 0.01-30% by weight of the total composition. In some embodiments, one or more carbonate salts are present in an amount of 0.01-20% by weight of the total composition. In some embodiments, one or more carbonate salts are present in an amount of 0.01-10% by weight of the total composition. In some embodiments, one or more carbonate salts are present in an amount of 0.01-5% by weight of the total composition. In some embodiments, one or more carbonate salts are present in an amount of 0.05-30% by weight of the total composition. In some embodiments, one or more carbonate salts are present in an amount of 0.05-20% by weight of the total composition. In some embodiments, one or more carbonate salts are present in an amount of 0.05-10% by weight of the total composition. In some embodiments, one or more carbonate salts are present in an amount of 0.05-5% by weight of the total composition. In some embodiments, one or more carbonate salts are present in an amount of 0.1-30% by weight of the total composition. In some embodiments, one or more carbonate salts are present in an amount of 0.1-20% by weight of the total composition. In some embodiments, one or more carbonate salts are present in an amount of 0.1-10% by weight of the total composition. In some embodiments, one or more carbonate salts are present in an amount of 0.1-5% by weight of the total composition. In some embodiments, one or more carbonate salts are present in an amount of 0.5-30% by weight of the total composition. In some embodiments, one or more carbonate salts are present in an amount of 0.5-20% by weight of the total composition. In some embodiments, one or more carbonate salts are present in an amount of 0.5-10% by weight of the total composition. In some embodiments, one or more carbonate salts are present in an amount of 0.5-5% by weight of the total composition. In some embodiments, one or more carbonate salts are present in an amount of 1-30% by weight of the total composition. In some embodiments, one or more carbonate salts are present in an amount of 1-20% by weight of the total composition. In some embodiments, one or more carbonate salts are present in an amount of 1-10% by weight of the total composition. In some embodiments, one or more carbonate salts are present in an amount of 5-30% by weight of the total composition. In some embodiments, one or more carbonate salts are present in an amount of 5-20% by weight of the total composition. In some embodiments, one or more carbonate salts are present in an amount of 5-10% by weight of the total composition. In some embodiments, one or more carbonate salts are present in an amount of 10-30% by weight of the total composition. In some embodiments, one or more carbonate salts are present in an amount of 10-20% by weight of the total composition. In some embodiments, one or more carbonate salts are present in an amount of 20-30% by weight of the total composition. In some embodiments, one or more carbonate salts are present in an amount of 1-5% by weight of the total composition. In some embodiments, one or more carbonate salts are present in an amount of 0.1% by weight of the total composition. In some embodiments, one or more carbonate salts are present in an amount of 0.2% by weight of the total composition. In some embodiments, one or more carbonate salts are present in an amount of 0.3% by weight of the total composition. In some embodiments, one or more carbonate salts are present in an amount of 0.4% by weight of the total composition. In some embodiments, one or more carbonate salts are present in an amount of 0.5% by weight of the total composition. In some embodiments, one or more carbonate salts are present in an amount of 1% by weight of the total composition. In some embodiments, one or more carbonate salts are present in an amount of 1.5% by weight of the total composition. In some embodiments, one or more carbonate salts are present in an amount of 2% by weight of the total composition. In some embodiments, one or more carbonate salts are present in an amount of 2.5% by weight of the total composition. In some embodiments, one or more carbonate salts are present in an amount of 3% by weight of the total composition. In some embodiments, one or more carbonate salts are present in an amount of 3.5% by weight of the total composition. In some embodiments, one or more carbonate salts are present in an amount of 4% by weight of the total composition. In some embodiments, one or more carbonate salts are present in an amount of 4.5% by weight of the total composition. In some embodiments, one or more carbonate salts are present in an amount of 5% by weight of the total composition. In some embodiments, one or more carbonate salts are present in an amount of 5.5% by weight of the total composition. In some embodiments, one or more carbonate salts are present in an amount of 6% by weight of the total composition. In some embodiments, one or more carbonate salts are present in an amount of 6.5% by weight of the total composition. In some embodiments, one or more carbonate salts are present in an amount of 7% by weight of the total composition. In some embodiments, one or more carbonate salts are present in an amount of 7.5% by weight of the total composition. In some embodiments, one or more carbonate salts are present in an amount of 8% by weight of the total composition. In some embodiments, one or more carbonate salts are present in an amount of 8.5% by weight of the total composition. In some embodiments, one or more carbonate salts are present in an amount of 9% by weight of the total composition. In some embodiments, one or more carbonate salts are present in an amount of 9.5% by weight of the total composition. In some embodiments, one or more carbonate salts are present in an amount of 10% by weight of the total composition. In some embodiments, one or more carbonate salts are present in an amount of 12.5% by weight of the total composition. In some embodiments, one or more carbonate salts are present in an amount of 15% by weight of the total composition. In some embodiments, one or more carbonate salts are present in an amount of 17.5% by weight of the total composition. In some embodiments, one or more carbonate salts are present in an amount of 20% by weight of the total composition.

(d) Polyols

In some embodiments, the compositions of the present disclosure may optionally further comprise one or more polyols. Suitable polyols that may be included in the composition include, but are not limited to a diol, a triol, a saccharide, glycerine, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol. In some embodiments when the biophotonic composition of the disclosure includes one or more polyols, the polyol is glycerine. In some embodiments when the biophotonic composition of the disclosure includes one or more polyols, the polyol is propylene glycol. In some embodiments when the biophotonic composition of the disclosure includes one or more polyols, the polyol is a combination of glycerine and propylene glycol.

In some embodiments, one or more polyols are present in an amount of about 5-75% by weight of the total composition. In some embodiments, one or more polyols are present in an amount of about 10-75% by weight of the total composition. In some embodiments, one or more polyols are present in an amount of about 15-75% by weight of the total composition. In some embodiments, one or more polyols are present in an amount of about 20-75% by weight of the total composition. In some embodiments, one or more polyols are present in an amount of about 10% by weight of the total composition. In some embodiments, one or more polyols are present in an amount of about 15% by weight of the total composition. In some embodiments, one or more polyols are present in an amount of about 20% by weight of the total composition. In some embodiments, one or more polyols are present in an amount of about 25% by weight of the total composition. In some embodiments, one or more polyols are present in an amount of about 30% by weight of the total composition. In some embodiments, one or more polyols are present in an amount of about 35% by weight of the total composition. In some embodiments, one or more polyols are present in an amount of about 40% by weight of the total composition. In some embodiments, one or more polyols are present in an amount of about 45% by weight of the total composition. In some embodiments, one or more polyols are present in an amount of about 50% by weight of the total composition. In some embodiments, one or more polyols are present in an amount of about 55% by weight of the total composition. In some embodiments, one or more polyols are present in an amount of about 60% by weight of the total composition. In some embodiments, one or more polyols are present in an amount of about 65% by weight of the total composition. In some embodiments, one or more polyols are present in an amount of about 70% by weight of the total composition. In some embodiments, one or more polyols are present in an amount of about 75% by weight of the total composition.

In some embodiments, one or more polyols are present in an amount of 5-75% by weight of the total composition. In some embodiments, one or more polyols are present in an amount of 10-75% by weight of the total composition. In some embodiments, one or more polyols are present in an amount of 15-75% by weight of the total composition. In some embodiments, one or more polyols are present in an amount of 20-75% by weight of the total composition. In some embodiments, one or more polyols are present in an amount of 10% by weight of the total composition. In some embodiments, one or more polyols are present in an amount of 15% by weight of the total composition. In some embodiments, one or more polyols are present in an amount of 20% by weight of the total composition. In some embodiments, one or more polyols are present in an amount of 25% by weight of the total composition. In some embodiments, one or more polyols are present in an amount of 30% by weight of the total composition. In some embodiments, one or more polyols are present in an amount of 35% by weight of the total composition. In some embodiments, one or more polyols are present in an amount of 40% by weight of the total composition. In some embodiments, one or more polyols are present in an amount of 45% by weight of the total composition. In some embodiments, one or more polyols are present in an amount of 50% by weight of the total composition. In some embodiments, one or more polyols are present in an amount of 55% by weight of the total composition. In some embodiments, one or more polyols are present in an amount of 60% by weight of the total composition. In some embodiments, one or more polyols are present in an amount of 65% by weight of the total composition. In some embodiments, one or more polyols are present in an amount of 70% by weight of the total composition. In some embodiments, one or more polyols are present in an amount of 75% by weight of the total composition.

In the compositions and methods of the present disclosure, additional components may optionally be included, or used in combination with the biophotonic compositions as described herein. Such additional components include, but are not limited to, healing factors, growth factors, antimicrobials, wrinkle fillers (e.g. botox, hyaluronic acid or polylactic acid), collagens, anti-virals, anti-fungals, antibiotics, drugs, and/or agents that promote collagen synthesis. These additional components may be applied to the wound, skin or soft tissues including mucosa in a topical fashion, prior to, at the same time of, and/or after topical application of the biophotonic composition of the present disclosure, and may also be systemically administered. Suitable healing factors, antimicrobials, collagens, and/or agents that promote collagen synthesis are discussed below:

(e) Healing Factors

In some embodiments, the compositions of the present disclosure may optionally further comprise one or more healing factors. Healing factors comprise compounds that promote or enhance the healing or regenerative process of the tissues on the application site of the composition. During the photoactivation of the composition of the present disclosure, there is an increase of the absorption of molecules at the treatment site by the skin, wound or the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Studies have shown hyaluronic acid appearing in the early stages of healing to physically create room for white blood cells that mediate the immune response. It is used in the synthesis of biological scaffolds for wound healing applications and in wrinkle treatment. A suitable range of concentration over which hyaluronic acid can be used in the present composition is from about 0.001% to about 3% by weight of the total composition.

Glucosamine: is one of the most abundant monosaccharides in human tissues and a precursor in the biological synthesis of glycosylated proteins and lipids. It is commonly used in the treatment of osteoarthritis. The common form of glucosamine used is its sulfate salt and including glucosamine sulfate sodium chloride. Glucosamine shows a number of effects including an anti-inflammatory activity, stimulation of the synthesis of proteoglycans and the synthesis of proteolytic enzymes. A suitable range of concentration over which glucosamine can be used in the present composition is from about 0.01% to about 3% by weight of the total composition.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing.

Also, saffron can act as both a chromophore and a healing factor, and as a potentiator. Other healing agents can also be included such as growth factors.

(f) Antimicrobials

In some embodiments, the compositions of the present disclosure may optionally further comprise one or more antimicrobials. Antimicrobials kill microbes or inhibit their growth or accumulation. Exemplary antimicrobials (or antimicrobial agent) are recited in U.S. Patent Application Publications 20040009227 and 20110081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the trade name Triclosan®; 2,2'-methylene bis-(3,4,6-trichlorophenol); 2,2'-methylene bis-(4-chloro-6-bromophenol); bis-(2-hydroxy-3,5-dichlorophenyl) sulphide; and bis-(2-hydroxy-5-chlorobenzyl)sulphide.

Specific benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the disclosure include, but are not limited to: N—(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; *eucalyptus*; vervain; peppermint; gum benzoin; basil; fennel; fir; balsam; menthol; ocmea origanuin; hydastis; carradensis; Berberidaceac daceae; Ratanhiae *longa*; and *Curcuma longa*. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used in the disclosure include, but are not limited to, salts of metals in Groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethium; samarium; europium; gadolinium; terbium; dysprosium; holmium; erbium; thallium; ytterbium; lutetium; and mixtures thereof. An example of the metal-ion based antimicrobial agent is sold under the tradename HealthShield®, and is manufactured by HealthShield Technology, Wakefield, Mass.

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropynyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimerosal; dichlorobenzyl alcohol; captan; chlorphenesin; dichlorophene; chlorobutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, and U.S. Pat. Appl. Publ. Nos. 20040009227 and 20110081530, the contents of all of which are incorporated herein by reference.

(g) Collagens and Agents that Promote Collagen Synthesis

In some embodiments, the compositions of the present disclosure may optionally further comprise one or more collagens or agents that promote collagen synthesis. Collagen is a fibrous protein produced in dermal fibroblast cells and forming 70% of the dermis. Collagen is responsible for the smoothing and firming of the skin. Therefore, when the synthesis of collagen is reduced, skin aging will occur, and so the firming and smoothing of the skin will be rapidly reduced. As a result, the skin will be flaccid and wrinkled. On the other hand, when metabolism of collagen is activated by the stimulation of collagen synthesis in the skin, the components of dermal matrices will be increased, leading to effects, such as wrinkle improvement, firmness improvement and skin strengthening. Thus, collagens and agents that promote collagen synthesis may also be useful in the present disclosure. Agents that promote collagen synthesis (i.e., pro-collagen synthesis agents) include amino acids, peptides, proteins, lipids, small chemical molecules, natural products and extracts from natural products.

For instance, it was discovered that intake of vitamin C, iron, and collagen can effectively increase the amount of collagen in skin or bone. See, e.g., U.S. Patent Application Publication 20090069217, the contents of which are all incorporated herein by reference. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola and lemon may also be used. Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsin, trypsin, or chymotrypsin; and a mixture containing two or more of those collagens at an arbitrary rate. Collagens extracted from plant sources may also be used.

Additional pro-collagen synthesis agents are described, for example, in U.S. Pat. Nos. 7,598,291, 7,722,904, 6,203, 805, 5,529,769, etc., and U.S. Patent Application Publications 20060247313, 20080108681, 20110130459, 20090325885, and 20110086060, the contents of all of which are incorporated herein by reference.

The compositions of the disclosure can also include other ingredients such as humectants (e.g. glycerine, ethylene glycol, and propylene glycol), preservatives such as parabens, and pH adjusters such as sodium hydroxide and HCl. In some embodiments, the pH of the composition is in or adjusted to the range of about 4 to about 10. In some embodiments, the pH of the composition is in or adjusted to the range of about 4 to about 9. In some embodiments, the pH of the composition is in or adjusted to the range of about 4 to about 8. In some embodiments, the pH of the composition is within the range of about 4 to about 7. In some embodiments, the pH of the composition is within the range of about 4 to about 6.5. In some embodiments, the pH of the composition is within the range of about 4 to about 6. In some embodiments, the pH of the composition is within the range of about 4 to about 5.5. In some embodiments, the pH of the composition is within the range of about 4 to about 5. In some embodiments, the pH of the composition is within the range of about 5.0 to about 8.0. In some embodiments, the pH of the composition is within the range of about 6.0 to about 8.0. In some embodiments, the pH of the composition is within the range of about 6.5 to about 7.5. In some embodiments, the pH of the composition is within the range of about 5.5 to about 7.5.

In some embodiments, the pH of the composition is in or adjusted to the range of 4 to 10. In some embodiments, the pH of the composition is in or adjusted to the range of 4 to 9. In some embodiments, the pH of the composition is in or adjusted to the range of 4 to 8. In some embodiments, the pH of the composition is within the range of 4 to 7. In some embodiments, the pH of the composition is within the range of 4 to 6.5. In some embodiments, the pH of the composition is within the range of 4 to 6. In some embodiments, the pH of the composition is within the range of 4 to 5.5. In some embodiments, the pH of the composition is within the range of 4 to 5. In some embodiments, the pH of the composition is within the range of 5.0 to 8.0. In some embodiments, the pH of the composition is within the range of 6.0 to 8.0. In some embodiments, the pH of the composition is within the range of 6.5 to 7.5. In some embodiments, the pH of the composition is within the range of 5.5 to 7.5.

In some embodiments, the compositions of the disclosure also include an aqueous substance (water) or an alcohol. Alcohols include, but are not limited to, ethanol, propanol, isopropanol, butanol, iso-butanol, t-butanol or pentanol. In some embodiments, the first chromophore is in solution in a medium of the biophotonic composition. In some embodiments wherein the first chromophore is in solution in a medium of the biophotonic composition, the medium is an aqueous substance. In some embodiments, the first and second chromophores are in solution in a medium of the biophotonic composition. In some embodiments wherein the first and second chromophores are in solution in a medium of the biophotonic composition, the medium is an aqueous substance. In some embodiments, the first, second, and third chromophores are in solution in a medium of the biophotonic composition. In some embodiments wherein the first, second, and third chromophores are in solution in a medium of the biophotonic composition, the medium is an aqueous substance.

(4) Methods of Use

The biophotonic compositions of the present disclosure have numerous uses. Without being bound by theory, the biophotonic compositions of the present disclosure are useful in promoting wound healing or tissue repair. The biophotonic compositions of the present disclosure are useful for treating or preventing a skin disorder. The biophotonic compositions of the present disclosure are useful in treating acne. The biophotonic compositions of the present disclosure are useful in treating acne scars. The biophotonic compositions of the present disclosure are useful for skin rejuvenation. The biophotonic compositions of the present disclosure are useful for treating acute or chronic inflammation. The biophotonic compositions of the present disclosure are useful for treating or preventing an oral disease. Therefore, it is an objective of the present disclosure to provide a method of providing biophotonic therapy to a wound, wherein the method promotes wound healing. It is also an objective of the present disclosure to provide a method of providing biophotonic therapy to a skin tissue afflicted with acne, wherein the method is used to treat acne. It is an objective of the present disclosure to provide a method of providing biophotonic therapy to a skin tissue afflicted with acne scars, wherein the method is used to treat acne scars. It is also an objective of the present disclosure to provide a method of providing biophotonic therapy to a skin tissue afflicted with a skin disorder, wherein the method is used to treat or prevent the skin disorder. It is an objective of the present disclosure to provide a method of providing biophotonic therapy to skin tissue, wherein the method is used for promoting skin rejuvenation. It is also an objective of the present disclosure to provide a method of providing biophotonic therapy to a subject's mouth, wherein the method is used to treat or prevent an oral disease.

A "patient," "subject," or "host" to be treated by the disclosed compositions and methods may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In some embodiments, the subject is a mammal. In some embodiments, the subject is a human. A patient refers to a subject afflicted with a disease or disorder.

The term "therapeutic" treatment is art-recognized and includes administration to the host of one or more of the subject compositions. If treatment is administered after manifestation of the unwanted condition, the treatment is therapeutic (i.e., it is intended to diminish, ameliorate, or stabilize the existing unwanted condition or side effects thereof).

The present disclosure provides a method for providing a biophotonic therapy to a wound, the method comprising: applying (e.g., by topical application) to a site of a wound a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy to a wound, comprising: topically applying to a wound a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy to a wound, comprising: topically applying to a wound a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for treating a wound, the method comprising: topically applying to a site of a wound a biophotonic composition of the present disclosure, and illuminating the biophotonic composition with light having a wavelength that overlaps with an absorption spectrum of the chromophore(s) of the biophotonic composition.

In another aspect, the present disclosure provides a method of treating a wound, comprising: topically applying to a site of a wound a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method of treating a wound, comprising: topically to a site of a wound applying a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy for skin rejuvenation, the method comprising: applying (e.g., by topical application) to the skin a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy for skin rejuvenation, comprising: topically applying to the skin a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy for skin rejuvenation, comprising: topically applying to the skin a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In some aspects, the present disclosure provides a method for providing skin rejuvenation, the method comprising: applying (e.g., by topical application) to the skin a biophotonic composition of the present disclosure, and illuminating the biophotonic composition with light having a wavelength that overlaps with an absorption spectrum of the chromophore(s) of the biophotonic composition.

The present disclosure provides a method for promoting skin rejuvenation comprising: topically applying to the skin a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some embodiments, the present disclosure provides a method for promoting skin rejuvenation comprising: topically applying to the skin a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy to a target skin tissue, the method comprising: applying (e.g., by topical application) to a target skin tissue a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy to a target skin tissue afflicted with a skin disorder, comprising: topically applying to a target skin tissue a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy to a target skin tissue afflicted with a skin disorder, comprising: topically applying to a target skin tissue a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for treating or preventing a skin disorder, the method comprising: topically applying to a target skin tissue afflicted with the skin disorder a biophotonic composition of the present disclosure, and illuminating the biophotonic composition with light having a wavelength that overlaps with an absorption spectrum of the chromophore(s) of the biophotonic composition.

The present disclosure provides a method for treating or preventing a skin disorder, comprising: topically applying to a target skin tissue afflicted with the skin disorder a biophotonic composition, wherein the biophotonic composition comprises a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some embodiments, the present disclosure provides a method for treating or preventing a skin disorder, comprising: topically applying to a target skin tissue afflicted with the skin disorder a biophotonic composition, wherein the biophotonic composition comprises a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy to a target skin tissue afflicted with acne, the method comprising: applying (e.g., by topical application) to a target skin tissue a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy to a target skin tissue afflicted with acne, comprising: topically applying to a target skin tissue a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy to a target skin tissue afflicted with acne, comprising: topically applying to a target skin tissue a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for treating acne, the method comprising: topically applying to a target skin tissue a biophotonic composition of the present disclosure, and illuminating the biophotonic composition with light having a wavelength that overlaps with an absorption spectrum of the chromophore(s) of the biophotonic composition.

The present disclosure provides a method for treating acne, comprising: topically applying to a target skin tissue a biophotonic composition, wherein the biophotonic composition comprises a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

The present disclosure further provides a method for treating acne, comprising: topically applying to a target skin tissue a biophotonic composition, wherein the biophotonic composition comprises a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy to a target skin tissue afflicted with acne scars, the method comprising: applying (e.g., by topical application) to a target skin tissue a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy to a target skin tissue afflicted with acne scars, comprising: topically applying to a target skin tissue a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy to a target skin tissue afflicted with acne scars, comprising: topically applying to a target skin tissue a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for treating acne scars, comprising: topically applying to a target skin a biophotonic composition comprising a first chromophore; and illuminating said biophotonic composition with light having a wavelength that overlaps with an absorption spectrum of the first chromophore.

The present disclosure provides a method for treating acne scars, comprising: topically applying to a target skin a biophotonic composition, wherein the biophotonic composition comprises a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

The present disclosure further provides a method for treating acne scars, comprising: topically applying to a target skin afflicted a biophotonic composition, wherein the biophotonic composition comprises a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy to a target tissue afflicted with acute or chronic inflammation, the method comprising: applying (e.g., by topical application) to a target skin tissue a biophotonic composition of the present disclosure, and illuminating the biophotonic composition with light having a wavelength that overlaps with an absorption spectrum of the chromophore(s) of the biophotonic composition.

In some aspects, the present disclosure provides a method for providing biophotonic therapy to a target tissue afflicted with acute or chronic inflammation, comprising: topically applying to a target skin tissue a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

In some aspects, the present disclosure provides a method for providing biophotonic therapy to a target tissue afflicted with acute or chronic inflammation, comprising: topically applying to a target skin tissue a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

In another aspect, the present disclosure provides a method for treating acute or chronic inflammation, comprising: topically applying to a target tissue with acute or chronic inflammation a biophotonic composition comprising a first chromophore; and illuminating said biophotonic composition with light having a wavelength that overlaps with an absorption spectrum of the first chromophore.

The present disclosure provides a method for treating acute or chronic inflammation, comprising: topically applying to a target tissue with acute or chronic inflammation a biophotonic composition, wherein the biophotonic composition comprises a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols.

The present disclosure also provides a method for treating acute or chronic inflammation, comprising: topically applying to a target tissue with acute or chronic inflammation a biophotonic composition, wherein the biophotonic composition comprises a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore.

The present disclosure provides a method for providing a biophotonic therapy to a target tissue afflicted with acute or chronic inflammation, the method comprising: applying (e.g., by topical application) to a target skin tissue a biophotonic composition of the present disclosure, and illuminating the biophotonic composition with light having a wavelength that overlaps with an absorption spectrum of the chromophore(s) of the biophotonic composition. In some embodiments, the target site may be skin or nails.

In some aspects, the present disclosure provides a method for providing biophotonic therapy to a target site afflicted with fungal infection, comprising: topically applying to a target site a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the target site may be skin or nails. In some embodiments, the composition further comprises one or more polyols.

In some aspects, the present disclosure provides a method for providing biophotonic therapy to a target site afflicted with fungal infection, comprising: topically applying to a target site a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the target site may be skin or nails.

In another aspect, the present disclosure provides a method for treating a fungal infection, comprising: topically applying to a target site afflicted with fungal infection a biophotonic composition comprising a first chromophore; and illuminating said biophotonic composition with light having a wavelength that overlaps with an absorption spectrum of the first chromophore. In some embodiments, the target site may be skin or nails.

In another aspect, the present disclosure provides a method for treating a fungal infection, comprising: topically applying to a target site afflicted with fungal infection a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the target site may be skin or nails. In some embodiments, the composition further comprises one or more polyols.

In another aspect, the present disclosure provides a method for a treating fungal infection, comprising: topically applying to a target site afflicted with fungal infection a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the target site may be skin or nails.

The present disclosure provides a method for providing a biophotonic therapy to a target mouth afflicted with an oral disease, the method comprising: applying (e.g., by topical application) to a target site a biophotonic composition of the present disclosure, and illuminating the biophotonic composition with light having a wavelength that overlaps with an absorption spectrum of the chromophore(s) of the biophotonic composition. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the present disclosure provides a method for providing biophotonic therapy to a target mouth afflicted with an oral disease, comprising: topically applying to a target site a biophotonic composition comprising a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the present disclosure provides a method for providing biophotonic therapy to a target mouth afflicted with an oral disease, comprising: topically applying to a target site a biophotonic composition comprising a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

In some aspects, the present disclosure provides a method for treating or preventing an oral disease, comprising: topically applying to the mouth of a subject a biophotonic composition comprising a first chromophore; and illuminating said biophotonic composition with light having a wavelength that overlaps with an absorption spectrum of the first chromophore. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

The present disclosure provides a method for treating or preventing an oral disease, comprising: topically applying to the mouth of a subject a biophotonic composition, wherein the biophotonic composition comprises a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In some embodiments, the composition further comprises one or more polyols. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

The present disclosure also provides a method for treating or preventing an oral disease, comprising: topically applying to the mouth of a subject a biophotonic composition, wherein the biophotonic composition comprises a first chromophore, one or more polyols, and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate; and illuminating said biophotonic composition with light having a wavelength that overlaps with an absorption spectrum of the first chromophore. In certain such embodiments, said oral disease is chosen from gingivitis, periodontitis, periodontal disease, oral thrush, lichen planus, stomatitis, herpes simplex lesion, oral mucositis, oral ulcers, oral submucous fibrosis, and glossitis.

The biophotonic compositions suitable for use in the methods of the present disclosure may be selected from any of the embodiments of the biophotonic compositions described above. For instance, the biophotonic compositions useful in the method of the present disclosure may comprise a first chromophore that undergoes at least partial photobleaching upon application of light. In some embodiments, the biophotonic compositions of the disclosure maintain, within a first minute of illumination, at least 80% of their initial level of fluorescence. The first chromophore may absorb at a wavelength of about 200 to about 800 nm, about 200 to about 700 nm, about 200 to about 600 nm or about 200 to about 500 nm. In some embodiments, the first chromophore absorbs at a wavelength of about 200 to about 600 nm. In some embodiments, the first chromophore absorbs light at a wavelength of about 200 to about 300 nm, about 250 to about 350 nm, about 300 to about 400 nm, about 350 to about 450 nm, about 400 to about 500 nm, about 450 to about 650 nm, about 600 to about 700 nm, about 650 to about 750 nm or about 700 to about 800 nm. In other examples, suitable biophotonic compositions for the methods of the present disclosure may further comprise at least one additional chromophore (e.g., a second chromophore). The absorption spectrum of the second chromophore overlaps at least about 80%, about 70%, about 60%, about 50%, about 40%, about 30%, or about 20% with the emission spectrum of the first chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Illumination of the biophotonic composition with light may cause a transfer of energy from the first chromophore to the second chromophore. Subsequently, the second chromophore may emit energy as fluorescence and/or generate reactive oxygen species. In some embodiments of the methods the present disclosure, energy transfer caused by the application of light is not accompanied by concomitant generation of heat, or does not result in tissue damage.

When the method involves a biophotonic composition having at least two chromophores, the first chromophore is present in an amount of about 0.005-40% by weight of the composition, and the second chromophore is present in an amount of about 0.0001-40% by weight of the composition. In some embodiments, the first chromophore is present in an amount of about 0.005-2%, about 0.01-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition. In some embodiments, the second chromophore is present in an amount of about 0.0001-2%, about 0.001-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the total weight by weight of the first chromophore or combination of chromophores may be in the amount of about 0.005-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore or combination of chromophores is present in an amount of at least about 0.2% by weight of the composition.

In some embodiments when the method involves a biophotonic composition having at least two chromophores, the first chromophore is present in an amount of 0.005-40% by weight of the composition, and the second chromophore is present in an amount of 0.0001-40% by weight of the composition. In some embodiments, the first chromophore is present in an amount of 0.005-2%, 0.01-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore is present in an amount of at least 0.2% by weight of the composition. In some embodiments, the second chromophore is present in an amount of 0.0001-2%, 0.001-1%, 0.1-1%, 0.1-2%, 0.5-2%, 1-5%, 2.5-7.5%, 5-10%, 7.5-12.5%, 10- 15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the total weight by weight of the first chromophore or combination of chromophores may be in the amount of 0.005-1%, 0.1-1%, 0.1-2%, 0.5-2%, 1-5%, 2.5-7.5%, 5-10%, 7.5-12.5%, 10-15%, 12.5- 17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore or combination of chromophores is present in an amount of at least 0.2% by weight of the composition.

In the methods of the present disclosure, any source of actinic light can be used to illuminate the biophotonic compositions. Any type of halogen, LED or plasma arc lamp or laser may be suitable. The primary characteristic of suitable sources of actinic light will be that they emit light in a wavelength (or wavelengths) appropriate for activating the one or more photoactivators present in the composition. In some embodiments, an argon laser is used. In some embodiments, a potassium-titanyl phosphate (KTP) laser (e.g. a GreenLight™ laser) is used. In another embodiment, sunlight may be used. In some embodiments, a LED photocuring device is the source of the actinic light. In some embodiments, the source of the actinic light is a source of light having a wavelength between about 200 nm to about 800 nm. In some embodiments, the source of the actinic light is a source of visible light having a wavelength between about 400 nm and about 700 nm. In some embodiments, the source of the actinic light is a source of visible light having a wavelength between about 400 nm and about 600 nm. In some embodiments, the source of the actinic light is a source of visible light having a wavelength between about 400 nm and about 550 nm. In some embodiments, the source of the actinic light is a source of visible light having a wavelength between about 380 nm and about 700 nm. In some embodiments, the source of the actinic light is a source of visible light having a wavelength between about 380 nm and about 600 nm. In some embodiments, the source of the actinic light is a source of visible light having a wavelength between about 380 nm and about 550 nm. In some embodiments, the source of the actinic light is a source of light having a wavelength between 200 nm to 800 nm. In some embodiments, the source of the actinic light is a source of visible light having a wavelength between 400 nm and 700 nm. In some embodiments, the source of the actinic light is a source of visible light having a wavelength between 400 nm and 600 nm. In some embodiments, the source of the actinic light is a source of visible light having a wavelength between 400 nm and 550 nm. In some embodiments, the source of the actinic light is a source of visible light having a wavelength between 380 nm and 700 nm. In some embodiments, the source of the actinic light is a source of visible light having a wavelength between 380 nm and 600 nm. In some embodiments, the source of the actinic light is a source of visible light having a wavelength between 380 nm and 550 nm. In some embodiments, the biophotonic composition of the disclosure is illuminated with violet and/or blue light. Furthermore, the source of actinic light should have a suitable power density. Suitable power density for non-collimated light sources (LED, halogen or plasma lamps) are in the range from about 1 mW/cm$^2$ to about 200 mW/cm$^2$. Suitable power density for laser light sources are in the range from about 0.5 mW/cm$^2$ to about 0.8 mW/cm$^2$.

In some embodiments of the methods of the present disclosure, the light has an energy at the subject's skin, wound or mucosa surface of between about 1 mW/cm$^2$ and about 500 mW/cm$^2$, about 1-300 mW/cm$^2$, or about 1-200 mW/cm$^2$, wherein the energy applied depends at least on the condition being treated, the wavelength of the light, the distance of the subject's skin from the light source, and the thickness of the biophotonic composition. In some embodiments, the light at the subject's skin is between about 1-40 mW/cm$^2$, or about 20-60 mW/cm$^2$, or about 40-80 mW/cm$^2$, or about 60-100 mW/cm$^2$, or about 80-120 mW/cm$^2$, or about 100-140 mW/cm$^2$, or about 120-160 mW/cm$^2$, or about 140-180 mW/cm$^2$, or about 160-200 mW/cm$^2$, or about 110-240 mW/cm$^2$, or about 110-150 mW/cm$^2$, or about 190-240 mW/cm$^2$.

In some embodiments, a mobile device can be used to activate embodiments of the biophotonic composition of the present disclosure, wherein the mobile device can emit light having an emission spectrum which overlaps an absorption spectrum of the chromophore in the biophotonic composition. The mobile device can have a display screen through which the light is emitted and/or the mobile device can emit light from a flashlight which photoactivates the biophotonic composition.

In some embodiments, a display screen on a television or a computer monitor can be used to activate the biophotonic composition, wherein the display screen can emit light having an emission spectrum which overlaps an absorption spectrum of a photoactive agent in the photoactivatable composition.

In some embodiments, the first and/or the second chromophore (when present) can be photoactivated by ambient light which may originate from the sun or other light sources. Ambient light can be considered to be a general illumination that comes from all directions in a room that has no visible source. In some embodiments, the first and/or the second chromophore (when present) can be photoactivated by light in the visible range of the electromagnetic spectrum. Exposure times to ambient light may be longer than that to direct light.

In some embodiments, different sources of light can be used to activate the biophotonic compositions, such as a combination of ambient light and direct LED light.

The duration of the exposure to actinic light required will be dependent on the surface of the treated area, the type of lesion, trauma or injury that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In some embodiments, the time of exposure to actinic light of the tissue, skin or wound on which the biophotonic composition has been applied is a period between 1 minute and 30 minutes. In some embodiments, the time of exposure to actinic light of the tissue, skin or wound on which the biophotonic composition has been applied is a period between 1 minute and 5 minutes. In some embodiments, the time of exposure to actinic light of the tissue, skin or wound on which the biophotonic composition has been applied is a period between 1 minute and 5 minutes. In some embodiments, the biophotonic composition is illuminated for a period between 1 minute and 3 minutes. In some embodiments, light is applied for a period of 1-30 seconds, 1-60 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 20-30 minutes. In some embodiments, light is applied for a period of 1 second. In some embodiments, the biophotonic composition is illuminated for a period less than 30 minutes. In some embodiments, the biophotonic composition is illuminated for a period less than 20 minutes. In some embodiments, the biophotonic composition is illuminated for a period less than 15 minutes. In some embodiments, the biophotonic composition is illuminated for a period less than 10 minutes. In some embodiments, the biophotonic composition is illuminated for a period less than 5 minutes. In some embodiments, the biophotonic composition is illuminated for a period less than 1 minute. In some embodiments, the biophotonic composition is illuminated for a period less than 30 seconds. In some embodiments, the biophotonic composition is illuminated for a period less than 20 seconds. In some embodiments, the biophotonic composition is illuminated for a period less than 10 seconds. In some embodiments, the biophotonic composition is illuminated for a period less than 5 seconds. In some embodiments, the biophotonic composition is illuminated for a period less than 1 second. In some embodiments, the source of actinic light is in continuous motion over the treated area for the appropriate time of exposure. In some embodiments, multiple applications of the biophotonic composition and actinic light are performed. In some embodiments, the tissue, skin or wound is exposed to actinic light at least two, three, four, five or six times. In some embodiments, a fresh application of the biophotonic composition is applied before exposure to actinic light.

In the methods of the present disclosure, the biophotonic composition may be optionally removed from the site of treatment following application of light. In some embodiments, the biophotonic composition is left on the treatment site for more than 30 minutes, more than one hour, more than 2 hours, more than 3 hours. It can be illuminated with ambient light. To prevent drying, the composition can be covered with a transparent or translucent cover such as a polymer film, or an opaque cover which can be removed before illumination.

For any of the methods described herein, the embodiments of this disclosure contemplate the use of any of the compositions, or mixtures of them, described throughout the application. In addition, in various embodiments of any of the methods described herein, combinations of any step or steps of one method with any step or steps from another method may be employed.

(5) Wounds and Wound Healing

The biophotonic compositions and methods of the present disclosure are useful to treat wounds and promote wound healing. Wounds that may be treated by the biophotonic compositions and methods of the present disclosure include, for example, injuries to the skin and subcutaneous tissue initiated in different ways (e.g., pressure ulcers from extended bed rest, wounds induced by trauma, wounds induced by conditions such as periodontitis) and with varying characteristics. In some embodiments, the present disclosure provides biophotonic compositions and methods for treating and/or promoting the healing of, for example, burns, incisions, excisions, lacerations, abrasions, puncture or penetrating wounds, surgical wounds, contusions, hematomas, crushing injuries, sores and ulcers. Wounds that may be treated by the biophotonic compositions and methods of the present disclosure also include wounds of the skin and soft tissues. The biophotonic compositions and methods of the present disclosure are also useful for cosmesis.

Biophotonic compositions and methods of the present disclosure are useful to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

The present disclosure provides biophotonic compositions and methods for treating and/or promoting healing, Grade I-IV ulcers. In some embodiments, the application provides compositions suitable for use with Grade II ulcers in particular. Ulcers may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

For example, the present disclosure provides biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In some embodiments, compositions and methods of treating a chronic wound are provided here in, where the chronic wound is characterized by diabetic foot ulcers and/or ulcerations due to neurologic and/or vascular complications of diabetes.

In other examples, the present disclosure provides biophotonic compositions and methods for treating and/or promoting healing of a pressure ulcer. Pressure ulcer includes bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turns red, becomes painful and can become necrotic. If untreated, the skin breaks open and can become infected. An ulcer sore is therefore a skin ulcer that occurs in an area of the skin that is under pressure from e.g. lying in bed, sitting in a wheelchair, and/or wearing a cast for a prolonged period of time. Pressure ulcer can occur when a person is bedridden, unconscious, unable to sense pain, or immobile. Pressure ulcer often occur in boney prominences of the body such as the buttocks area (on the sacrum or iliac crest), or on the heels of foot.

In other examples, the present disclosure provides biophotonic compositions and methods for treating and/or promoting healing of acute wounds.

Additional types of wound that can be treated by the biophotonic compositions and methods of the present disclosure include those disclosed by U.S. Pat. Appl. Publ. No. 20090220450, which is incorporated herein by reference.

Wound healing in adult tissues is a complicated reparative process. For example, the healing process for skin involves the recruitment of a variety of specialized cells to the site of the wound, extracellular matrix and basement membrane deposition, angiogenesis, selective protease activity and re-epithelialization.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote the wound healing by promoting the formation of substantially uniform epithelialization; promoting collagen synthesis; promoting controlled contraction; and/or by reducing the formation of scar tissue. In some embodiments, the biophotonic compositions and methods of the present disclosure are useful in promoting wound healing by promoting the formation of substantially uniform epithelialization. In some embodiments, the biophotonic compositions and methods of the present disclosure promote collagen synthesis. In some embodiments, the biophotonic compositions and methods of the present disclosure promote controlled contraction. In some embodiments, the biophotonic compositions and methods of the present disclosure promote wound healing, for example, by reducing the formation of scar tissue or by speeding up the wound closure process. In some embodiments, the biophotonic compositions and methods of the present disclosure promote wound healing, for example, by reducing inflammation. In some embodiments, the biophotonic composition can be used following wound closure to optimize scar revision. In this case, the biophotonic composition may be applied at regular intervals such as once a week, or at an interval deemed appropriate by the physician.

The biophotonic composition may be soaked into a woven or non-woven material or a sponge and applied as a wound dressing. A light source, such as LEDs or waveguides, may be provided within or adjacent the wound dressing or the composition to illuminate the composition. The waveguides can be optical fibers which can transmit light, not only from their ends, but also from their body. In some embodiments, the waveguides are made of polycarbonate or polymethylmethacrylate.

Adjunct therapies which may be topical or systemic such as antibiotic treatment may also be used. Negative pressure assisted wound closure can also be used to assist wound closure and/or to remove the composition.

(6) Acne and Acne Scars

The biophotonic compositions and methods of the present disclosure are useful to treat acne. As used herein, "acne" means a disorder of the skin caused by inflammation of skin glands or hair follicles. The biophotonic compositions and methods of the disclosure can be used to treat acne at early pre-emergent stages or later stages where lesions from acne are visible. Mild, moderate and severe acne can be treated with embodiments of the biophotonic compositions and methods. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the biophotonic compositions and methods of the present disclosure can be used to treat one or more of skin irritation, pitting, development of scars, acne scars, comedones, inflammatory papules, cysts, hyperkeratinazation, and thickening and hardening of sebum associated with acne.

The composition may be soaked into or applied to a woven or non-woven material or a sponge and applied as a mask to body parts such as the face, body, arms, legs, etc. A light source, such as LEDs or waveguides, may be provided within or adjacent the mask or the composition to illuminate the composition. The waveguides can be optical fibers which can transmit light, not only from their ends, but also from their body. In some embodiments, the waveguides are made of polycarbonate or polymethylmethacrylate.

The biophotonic compositions and methods of the present disclosure are useful in the treatment of various types of acne. Some types of acne include, for example, acne vulgaris, cystic acne, acne atrophica, bromide acne, chlorine acne, acne conglobate, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne *pustulosa*, acne scorbutica, acne scrofulosorum, acne urticata, acne varioliformis, acne *venenata*, propionic acne, acne excoriee, gram negative acne, steroid acne, and nodulocystic acne.

(7) Skin Aging and Rejuvenation

The dermis is the second layer of skin, containing the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The aging of skin comes with significant physiological changes to the skin. The generation of new skin cells slows down, and the epidermal ridges of the dermal-epidermal junction flatten out. While the number of elastin fibers increases, their structure and coherence decrease. Also, the amount of collagen and the thickness of the dermis decrease with the aging of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-ageing. The skin becomes drier, roughness and scaling increase, the appearance becomes duller, and most obviously fine lines and wrinkles appear. Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of α-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles generally referred to as expression wrinkles, got general recognition. These wrinkles require loss of resilience, particularly in the dermis, because of which the skin is no longer able to resume its original state when facial muscles which produce facial expressions exert stress on the skin, resulting in expression wrinkles.

The compositions and methods of the present disclosure promote skin rejuvenation. In some embodiments, the compositions and methods of the present disclosure promote collagen synthesis. The compositions and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In some embodiments, the compositions and methods of the present disclosure may induce a reduction in pore size, enhance sculpturing of skin subsections, and/or enhance skin translucence.

(8) Skin Disorders

The biophotonic compositions and methods of the present disclosure are useful to treat skin disorders that include, but are not limited to, erythema, telangiectasia, actinic telangiectasia, psoriasis, skin cancer, pemphigus, sunburn, dermatitis, eczema, rashes, impetigo, lichen simplex chronicus, rhinophyma, perioral dermatitis, pseudofolliculitis barbae, drug eruptions, erythema multiforme, erythema nodosum, granuloma annulare, actinic keratosis, purpura, alopecia areata, aphthous stomatitis, drug eruptions, dry skin, chapping, xerosis, ichthyosis vulgaris, fungal infections, parasitic infection, herpes simplex, intertrigo, keloids, keratoses, milia, moluscum contagiosum, *pityriasis rosea*, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors. Accordingly, the biophotonic compositions and methods of the present disclosure can be used to treat redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors.

The composition may be soaked into or applied to a woven or non-woven material or a sponge and applied as a mask to body parts to treat skin disorders. A light source, such as LEDs or waveguides, may be provided within or adjacent the mask or the composition to illuminate the composition. The waveguides can be optical fibres which can transmit light, not only from their ends, but also from their body. In some embodiments, the waveguides are made of polycarbonate or polymethylmethacrylate.

(9) Acute and Chronic Inflammation

Acute inflammation can present itself as pain, heat, redness, swelling and loss of function. It includes conditions seen in allergic reactions e.g.; such as insect bites (mosquito, bees, wasps, ants, spiders etc.), reaction to poison ivy or stinging nettle or the like, post-ablative treatment.

Chronic inflammation can be caused by conditions including, but not limited to, persistent injuries or infections, such as ulcers or tuberculosis; prolonged exposure to a toxic agent; cancer, diabetes, or autoimmune diseases such as rheumatoid arthritis, systemic lupus erythematosus, and multiple sclerosis.

The composition may be soaked into or applied to a woven or non-woven material or a sponge and applied as a mask to body parts to treat skin disorders. A light source, such as LEDs or waveguides, may be provided within or adjacent the mask or the composition to illuminate the composition. The waveguides can be optical fibres which can transmit light, not only from their ends, but also from their body. In some embodiments, the waveguides are made of polycarbonate or polymethylmethacrylate.

(10) Oral Diseases

The biophotonic compositions and methods of the present disclosure are useful to treat oral diseases. The oral disease may be chosen from, but is not limited to, gingivitis, periodontitis, periodontal disease, oral thrush, lichen planus, and stomatitis.

Gingivitis

Gingivitis is a disorder that is defined by the inflammation of the gums, and is characterized as a periodontal disease, which are characterized by the destruction of the gums, tissue, tooth sockets, and ligaments which create the structure that holds the teeth in place. Gingivitis is one of the first stages of serious periodontal disease.

The symptoms of gingivitis include swollen gums, mouth sores, a bright red or purple appearance to the gums, shiny gums, gums that are painless except when touched, and bleeding gums. Often the first signs of gingivitis have no symptoms except for visual symptoms and is likely only to be diagnosed by a dental professional.

Periodontal Disease

Periodontal disease is more prevalent in developing nations and in most cases, a professional cleaning and antibiotics can clear up most cases of periodontal disease. However, if left untreated the infection can spread throughout the body and can lead to serious health complications.

Symptoms of periodontal disease include painful gums, bad breath, a foul taste to the mouth, fever, gums that bleed with only mild amounts of pressure, crater sized canker sores between the teeth and gums, swollen lymph nodes around the head, neck, or jaw, a gray film on the gums, red gums, swollen gums, and pain when eating and swallowing.

Periodontitis

Periodontitis or Pyorrhea alveolaris is the inflammation of the periodontium which comprises tissues supporting the teeth in the oral cavity. Parts included in the periodontium are the gingiva (gum tissue), the alveolar bone which are sockets where teeth are attached, the cementum or outer layer of teeth roots and the periodontal ligaments or PDL composed of connective tissue fibers linking the gingival and cementum to the alveolar bone. The condition is described as the progressive loss of bone around teeth leading to loose teeth or loss of teeth if left unattended. There are different causes for the disease in which bacteria is the most common. Periodontitis is considered as an advanced phase of gum disease since it already involves bone loss in the area. It is the effect of mild gingivitis being left untreated. Due to the presence of bacterial infection, the body can also respond negatively to it leading to further complications. The condition is one of the leading causes of tooth loss among adults, affecting around 50% of everyone over the age of 30.

Signs and symptoms arise due to the unstable anchoring of teeth as well as the presence of microorganisms. Gums occasionally or frequently bleed or turn red while brushing teeth, using dental floss, biting into food, chewing or touching with fingers. Gums swell or develop pus occasionally as well. The affected individual likely has halitosis or bad breath and have a lingering metallic or tinny taste inside the mouth. Teeth seem longer and sharper due to gingival recession which partly may also be caused by hard brushing. If enzymes called collagenases have begun destroying collagen, the person will have deep pockets between the teeth and gums. In some embodiments, biophotonic compositions of the present disclosure are applied to the periodontal pockets of a subject.

During the early stages of periodontal disease, only a few signs and symptoms may be noticeable. Aggressive periodontitis may affect younger individuals and can occur in episodes. Some episodes may present very mild symptoms while others may be very severe. The signs and symptoms especially in the case of chronic periodontitis are usually progressive in nature.

Oral Thrush

Oral thrush is the condition where the fungus *Candida albicans* grows rapidly and uncontrollably in the mouth. The bacterium known as flora keeps the growth of *Candida albicans* under control in a healthy body. Oral thrush presents with creamy white paste that covers the tongue, and can spread rapidly to the roof of the mouth, gums, back of the throat, tonsils, and the inside of the cheeks. Babies, toddlers, older adults, and patients whose immune systems have been somehow compromised are most likely to come down with oral thrush.

Symptoms of oral thrush begin with a white pasty covering over the tongue and inside of the cheeks. As the oral thrush continues to develop, it can cause a mild amount of bleeding if the tongue is scraped or when the patient brushes their teeth. These symptoms may develop very quickly, but thrush can last for months. If the lesions of oral thrush spread down the esophagus, the patient may develop addition symptoms such as difficulty swallowing, the sensation of food being caught in the throat or the middle of the chest, and a fever should the infection continue to spread past the esophagus.

Lichen Planus

Lichen planus is most often defined as an oral disease that affects the lining of the mouth with inflammation. Lichen planus is most often recognized as a rash that irritates the tissue of the oral cavity. Most patients come down with their first case between the age of 45 and 60, although a slowly increasing number of reports dealing with younger patients have trickled in. While lichen planus is most often associated with the interior of the cheeks, many cases will find the entire mouth is affected, including the gums, the tongue, the lips, and in rare cases, the throat or esophagus. Lichen planus also occurs on the skin, as a skin disease, and often must be referred to specifically as skin lichen planus to differentiate between the oral type.

Lichen planus is a self-contained disease that can last for weeks, months, and in some cases, years. It is not contagious. It is often mistaken for genital diseases, as the genitalia are often the most noticeably affected during the early development stage. Because the symptoms and outbreaks occur rapidly and then disappear, often for weeks, treatment is difficult. While some patients find great relief in cool compresses or tub soaks and cool baths, most patients require medical treatment in order to relieve their symptoms.

Stomatitis

Stomatitis basically means inflammation of the mouth, but more specifically, stomatitis is the inflammation of the mucous lining of the mouth which may include the gums, tongue, cheeks, lips and the floor or roof of the mouth. There are different types of stomatitis and classification is based on how the disease was acquired by a person. The two types of stomatitis are contact stomatitis and aphthous stomatitis. Contact stomatitis is an inflammation of the oral mucosa caused by coming in contact with allergens or irritants. It is classified by its pattern of distribution, etiologic factors, and clinical features. There some cases of contact stomatitis that are left undetected because of the lack of clinical signs. Anybody can have contact stomatitis regardless of race, age and sex. Although it has been observed that it is more common in the elders.

Aphthous stomatitis, also known as canker sore or apthous ulcers, has an unknown etiology. Just like contact stomatitis, canker sore affects the oral mucosa. An aphthous ulcer is a type of oral ulcer, which presents as a painful open sore inside the mouth or upper throat (including the uvula) caused by a break in the mucous membrane. The condition is also known as Sutton's Disease, especially in the case of major, multiple, or recurring ulcers. The ulcers can be described as shallow, discrete, and painful and are usually visible on the mucous membranes that are unattached. This type of stomatitis, just like contact stomatitis, is self limited and do not usually cause complications. The normal size of ulcers may last for 1 to 2 weeks but larger ulcers may last for months.

Herpes Simplex Lesions

Herpes simplex is a viral disease caused by herpes simplex viruses; both herpes simplex virus 1 (HSV-1) and herpes simplex virus 2 (HSV-2) cause herpes simplex. Infection with the herpes virus is categorized into one of several distinct disorders based on the site of infection. Oral Herpes, the visible symptoms of which are colloquially called cold sores, and infects the face and mouth. Oral herpes is the most common form of herpes simplex viruses infection.

Other Oral Inflammatory Lesions

The subject matters of the present disclosure may be used to treat other types of oral inflammation, including but not limited to oral mucositis, oral ulcers caused by viral, bacterial, fungal or protozoan infections, or caused by disorders of the immune system (immunodeficiency, autoimmunity, or allergy). Also included is Oral Submucous Fibrosis, a chronic debilitating disease of the oral cavity characterized by inflammation and progressive fibrosis of the submucosal tissues. Also included is Glossitis, an inflammation or infection of the tongue. It causes the tongue to swell and change color.

(11) Kits

The present disclosure also provides kits for preparing and/or applying any of the compositions of the present disclosure. The kit may include a biophotonic topical composition, as defined above, together with one or more of a light source, devices for applying or removing the composition, instructions of use for the composition and/or light source. In some embodiments, the composition comprises at least a first chromophore; one or more salts selected from bicarbonate salts, carbonate salts or a combination of the foregoing salts; and one or more gelling agents, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the composition further comprises one or more polyols.

In some embodiments, the composition comprises at least a first chromophore, one or more gelling agents, and one or more polyols, wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

The first chromophore may be present in an amount of about 0.005-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition. The first chromophore may be present in an amount of 0.005-0.1%, 0.05-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore is present in an amount of at least 0.2% by weight of the composition.

In embodiments where the composition comprises more than one chromophore, the first chromophore may be present in an amount of about 0.005-40% by weight of the composition, and a second chromophore may be present in an amount of about 0.0001-40% by weight of the composition. In some embodiments, the first chromophore is present in an amount of about 0.005-2%, about 0.01-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore is present in an amount of at least about 0.2% by weight of the composition. In some embodiments, the second chromophore is present in an amount of about 0.0001-2%, about 0.001-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 2.5-37.5%, or about 35-40% by weight of the composition. In some embodiments, the amount of the first chromophore or combination of chromophores may be in the amount of about 0.05-40% by weight of the composition. In some embodiments, the amount of the first chromophore or combination of chromophores may be in the amount of about 0.005-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the composition. In some embodiments, the first chromophore or combination of chromophores is present in an amount of at least about 0.2% by weight of the composition. In embodiments where the composition comprises more than one chromophore, the first chromophore may be present in an amount of about 0.005-40% by weight of the composition, and a second chromophore may be present in an amount of about 0.0001-40% by weight of the composition. In some embodiments, the first chromophore is present in an amount of 0.005-2%, 0.01-0.1%, 0.05-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore is present in an amount of at least 0.2% by weight of the composition. In some embodiments, the second chromophore is present in an amount of 0.0001-2%, 0.001-0.1%, 0.05-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the amount of the first chromophore or combination of chromophores may be in the amount of about 0.05-40% by weight of the composition. In some embodiments, the amount of the first chromophore or combination of chromophores may be in the amount of 0.005-0.1%, 0.05-1%, 0.1-1%, 0.1-2%, 0.5-2%, 1-5%, 2.5-7.5%, 5-10%, 7.5-12.5%, 10- 15%, 12.5-17.5%, 15-20%, 17.5-22.5%, 20-25%, 22.5-27.5%, 25-30%, 27.5-32.5%, 30-35%, 32.5-37.5%, or 35-40% by weight of the composition. In some embodiments, the first chromophore or combination of chromophores is present in an amount of at least 0.2% by weight of the composition.

In some embodiments, the kit includes more than one composition, for example, a first and a second composition. The first composition may include one or more salts selected from bicarbonate salts, carbonate salts or a combination of the foregoing salts and the second composition may include the first chromophore in the one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the first composition, the second composition, or both further comprise one or more polyols.

In some embodiments, the first composition may include one or more polyols and the second composition may include the first chromophore, and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

The first chromophore may have an emission wavelength between about 400 nm and about 570 nm. The first chromophore may be present in the second composition in an amount of about 0.005-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the second composition. In some embodiments, the first chromophore is present in an amount of at least about 0.2% by weight of the second composition. In embodiments where the second composition comprises more than one chromophore, the first chromophore may be present in an amount of about 0.005-40% by weight of the second composition, and a second chromophore may be present in an amount of about 0.0001-40% by weight of the second composition. In some embodiments, the first chromophore is present in an amount of about 0.005-2%, about 0.001-0.1%, about 0.05-1%, about 0.1-1%, about 0.1-2%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the second composition. In some embodiments, the first chromophore is present in an amount of at least about 0.2% by weight of the second composition. In some embodiments, the second chromophore is present in an amount of about 0.0001-2%, about 0.001-0.1%, about 0.05-1%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the second composition. In some embodiments, the amount of the first chromophore or combination of chromophores may be in the amount of about 0.005-40% by weight of the second composition. In some embodiments, the amount of the first chromophore or combination of chromophores may be in the amount of about 0.005-0.1%, about 0.1-1%, about 0.1-2%, about 0.05-1%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% by weight of the second composition. In some embodiments, the first chromophore or combination of chromophores is present in an amount of at least about 0.2% by weight of the second composition. In some embodiments, the first chromophore or combination of chromophores is present in an amount of at least about 0.2% by weight of the second composition. The first chromophore may be present in the second composition in an amount of 0.005-0.1%, 0.05-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the second composition. In some embodiments, the first chromophore is present in an amount of at least 0.2% by weight of the second composition. In embodiments where the second composition comprises more than one chromophore, the first chromophore may be present in an amount of 0.005-40% by weight of the second composition, and a second chromophore may be present in an amount of 0.0001-40% by weight of the second composition. In some embodiments, the first chromophore is present in an amount of 0.005-2%, 0.001-0.1%, 0.05-1%, 0.1-1%, 0.1-2%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the second composition. In some embodiments, the first chromophore is present in an amount of at least 0.2% by weight of the second composition. In some embodiments, the second chromophore is present in an amount of 0.0001-2%, 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the second composition. In some embodiments, the amount of the first chromophore or combination of chromophores may be in the amount of 0.005-40% by weight of the second composition. In some embodiments, the amount of the first chromophore or combination of chromophores may be in the amount of 0.005-0.1%, 0.1-1%, 0.1-2%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% by weight of the second composition. In some embodiments, the first chromophore is present in an amount of at least 0.2% by weight of the second composition.

In some embodiments, the first composition may comprise the first chromophore in a liquid or as a powder, and the second composition may comprise one or more gelling agents for thickening the first composition, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. The salt selected from one or more bicarbonate salts or carbonate salts or a combination of the foregoing salts may be contained in the second composition or in a third composition in the kit, wherein said first, second, and third compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the first composition, the second composition, the third composition or all three compositions further comprise one or more polyols.

In some embodiments, the first composition may comprise the first chromophore in a liquid or as a powder, and the second composition may comprise one or more gelling agents for thickening the first composition, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. The one or more polyols may be contained in the second composition or in a third composition in the kit, wherein said first, second, and third compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments, the first composition may comprise the first chromophore in a liquid or as a powder, and the second composition may comprise one or more gelling agents for thickening the first composition and one or more salts selected from bicarbonate salts, carbonate salts or a combination of the foregoing salts, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the first composition, the second composition, or both further comprise one or more polyols.

In some embodiments, the first composition may comprise the first chromophore in a liquid or as a powder, and the second composition may comprise one or more gelling agents for thickening the first composition and a polyol, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments, the first composition may comprise the first chromophore and a polyol, and the second composition may comprise one or more gelling agents for thickening the first composition, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

In some embodiments, the kit includes containers comprising the compositions of the present disclosure. In some embodiments, the kit includes a first container comprising a first composition that includes one or more salts selected from bicarbonate salts, carbonate salts or a combination of the foregoing salts, and a second container comprising a second composition that includes at least one chromophore and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the first composition further comprises one or more gelling agents. In some embodiments, the first composition, the second composition, or both further comprise one or more polyols.

In some embodiments, the kit includes containers comprising the compositions of the present disclosure. In some embodiments, the kit includes a first container comprising a first composition that includes one or more salts selected from bicarbonate salts, carbonate salts or a combination of the foregoing salts and one or more gelling agents, and a second container comprising a second composition that includes at least one chromophore, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the second composition further comprises one or more gelling agents. In some embodiments, the first composition, the second composition, or both further comprise one or more polyols.

In some embodiments, the kit includes containers comprising the compositions of the present disclosure. In some embodiments, the kit includes a first container comprising a first composition that includes one or more polyols and a second container comprising a second composition that includes at least the first chromophore and one or more gelling agents, wherein said first and second compositions do not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate. In some embodiments, the first composition further comprises one or more gelling agents. In some embodiments, the second composition further comprises one or more polyols.

The containers may be light impermeable, air-tight and/or leak resistant. Exemplary containers include, but are not limited to, syringes, vials, or pouches. The first and second compositions may be included within the same container but separated from one another until a user mixes the compositions. For example, the container may be a dual-chamber syringe where the contents of the chambers mix on expulsion of the compositions from the chambers. In another example, the pouch may include two chambers separated by a frangible membrane. In another example, one component may be contained in a syringe and injectable into a container comprising the second component.

The biophotonic composition may also be provided in a container comprising one or more chambers for holding one or more components of the biophotonic composition, and an outlet in communication with the one or more chambers for discharging the biophotonic composition from the container.

In some embodiments, the kit comprises a systemic or topical drug for augmenting the treatment of the composition. For example, the kit may include a systemic or topical antibiotic or hormone treatment for acne treatment or wound healing.

Written instructions on how to use the biophotonic composition in accordance with the present disclosure may be included in the kit, or may be included on or associated with the containers comprising the compositions of the present disclosure.

In some embodiments, the kit may comprise a further component which is a dressing. The dressing may be a porous or semi-porous structure for receiving the biophotonic composition. The dressing may comprise woven or non-woven fibrous materials.

In some embodiments of the kit, the kit may further comprise a light source such as a portable light with a wavelength appropriate to activate the chromophore in the biophotonic composition. The portable light may be battery operated or re-chargeable.

In some embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

It should be appreciated that the subject matters of this disclosure are not limited to the particular embodiments described and illustrated herein but includes all modifications and variations falling within the scope of the subject matters of this disclosure as defined in the appended claims.

PART A. Oxygen/Oxygen-Species Production

Example 1

Brief Description of Gel Compositions and Assays for Oxygen/Oxygen-Species (ROS) Production The Examples of the present disclosure recite a number of differing gel compositions utilized in the course of various experimental protocols. For convenience and reference, a summary table (Table 1 below) is presented listing the various gel compositions along with a cross-reference to the particular Example of the present disclosure wherein the particular gel composition is mentioned. It is to be noted that for the Examples of the present disclosure, if a particular component were added to a given gel composition for testing of that particular component, the given component is identified as being added to the given gel composition.

TABLE 1

Gel compositions referred to Examples of the description

| Gel Name - Letter Abbreviation | Components | First Referred to in Example Number |
|---|---|---|
| A | Gel composition comprising gels A1 + A2 mixed together | 2 |
| A1 | Gel composition having urea peroxide (UP) + other components (but lacks having a chromophore) (% amount of UP may vary) | 2 |
| A2 | Gel composition containing a chromophore (Eosin Y @ 109 µg/g) + other components (but lacks UP). | 2 |
| A3 | A1 gel composition, lacking the UP | 2 |
| A4 | A2 gel composition, lacking the chromophore | 4 |
| B | Carbopol + $H_2O$ | 4 |
| C | Carbopol + $H_2O$ + (sodium) bicarbonate + chromophore | 5 |
| D1 | Carbopol + $H_2O$ + glycerin + chromophore | 5 |
| D2 | Carbopol + $H_2O$ + glycerin + propylene glycol (PG) + chromophore | 15 |
| E | Carbopol + $H_2O$ + glycerin + PG + parabens + chromophore | 17 |

A concentration of the chromophore such as Eosin Y (which may be abbreviated herein as EY or E) of 109 µg/g (per 100 grams of gel) is noted throughout the present disclosure to be 1×, and would translate into a chromophore concentration of 0.109% per 100 gram weight of a gel composition. In Examples wherein the amount of chromophore was altered, such levels are stated, as being 2× for twice the amount, 3× for three times the amount, etc., based on the noted 1× concentration.

Assays (i) The In Vitro Release Assay:

In an initial experiment, an in vitro release test was employed, the general procedure for which is described in "Topical and Transdermal Drug Products" (*Dissolution Technologies*, November 2010, at pages 17-18), incorporated herein by reference, and which consists of a placing a test sample (e.g., a gel or ointment or cream) onto a 3 cm diameter polycarbonate (PC) membrane having a pore size of 3 µm. The membrane is secured in a polycarbonate holder device, which is placed into a well of a 6 well plate such that the membrane is in direct contact (but not submerged) with a phosphate buffer saline (PBS) solution situated in the well. A typical form of the apparatus is a Thermo Scientific™ GENESYS™ 10S UV-Vis spectrophotometer, which is commercially available from Thermo Fisher Scientific Inc. In the case of the present disclosure, in order to assay for the production of ROS, the PBS solution also contained a quantity of liposomes (0.77 mg/mL of liposome are loaded into the well with the total sample), and the total volume of the PBS-liposome mixture in the well is 11 mL. A volume of 1.4 mL of the given gel sample, which equates to an approximately 2 mm thick layer of gel that would be typically applied in vivo, is placed onto the membrane and the gel is illuminated for 5 minutes using the KLOX multi-LED blue light (THERA™) at a distance of 5 cm from the gel surface. Upon completion of the illumination period, a 100 µL to 300 µL aliquot of the PBS-liposome solution is transferred from the test apparatus to a 96-well microtiter plate for performance of the ROS test (as further described below at (iii)).

(ii) The Dilution Assay:

For the dilution assay, an amount of a given gel composition is taken and mixed into a volume of PBS in order to dilute the gel. For example, to make a 10 mL solution ten times diluted, a 1 gram sample of the particular gel is mixed into 9 mL of PBS. Thereafter, depending on the make-up of the sample to be tested, an amount of a particular compound, for example urea peroxide (UP) or a particular salt, could be added in order to either boost an amount of the particular compound that was already in the sample to be tested or to test the effect of adding that given compound per se. With respect to adding UP in order to make test samples with various concentrations to be tested in a concomitant series of tests, an initial sample with a high concentration would be prepared from which aliquots would be taken and diluted down with PBS in order to the test samples with the various concentration of UP. In a multi-well plate, the given diluted sample are mixed with 19.1 µL of the liposome solution (to give a final liposome concentration of 15.4 mg/mL in the test sample) in order to provide a 2 mm thickness of the resulting paste-like mixture, this thickness being equivalent to a thickness of gel that would be spread on a patient or used in an in vitro assay. Also present in the sample-liposome mixture is a quantity of the chemical probe that is used in the reactive oxygen species (ROS) test assay (362.9 µL of the of the diluted gel (i.e., the given gel sample that is to be tested) is mixed with 19.1 µL of liposome-probe, as including the chemical probe in the sample-liposome mixture is to ensure that any ROS species will be afforded a maximal opportunity to interact with the probe and thus be detectable as having been generated as a result of any interaction that may occur in the gel composition upon it becoming activated. The prepared sample-liposome mixture is then illuminated under the THERA light that is placed at a distance of 5 cm from the sample, with the illumination time being 5 minutes. After the illumination is completed, a 100 µL to 300 µL aliquot of the sample-liposome transferred to a 96-well plate for conducting the ROS test (as further described in (iii) below). For the test samples, stock solutions of the samples were made and diluted such that direct comparisons could be made between the samples (e.g., for the measurement of reactive oxygen species).

(iii) The ROS Test Assay

The ROS test assay utilized in the experimental protocols of the Examples of the present disclosure is that which is described in Krumova et al. "How Lipid Unsaturation, Peroxyl Radical Partitioning, and Chromanol Lipophilic Tail Affect the Antioxidant Activity of α-Tocopherol: direct Visualization via High-Throughput Fluorescence Studies Conducted with Fluorogenic α-Tocopherol Analogues" (*J. Am. Chem. Soc.* 2012, vol. 134, pages 10102-10113). The assay utilizes highly sensitive fluorogenic α-tocopherol (TOH) analogues that undergo a 30-fold fluorescence intensity enhancement upon their reaction with peroxyl radicals that are generated due to the oxidation of the liposome membrane with ROS species that may be present in the reaction mixture. The assay utilizes a high-throughput microplate reader that relies on the high sensitivity of the TOH probes and provides a quantitative treatment of the temporal evolution of the fluorescence intensity thereby allowing for kinetic information to be obtained under the conditions being analyzed. The TOH analogues are two-segment receptor-reporter probes that consist of a chromanol moiety coupled to the meso position of a BODIPY fluorophore, either by an ester linker (the probe being called $H_2B$-TOH) or via a methylene linker (the probe being called $H_2B$-PMHC). The chromanol moiety quenches the emission of the fluorophore until it is oxidized following reaction with peroxyl radicals. The reporter segment for both probes is an improved BODIPY dye having improved redox potential; the favorable photoinduced electron transfer from the chromanol to the BODIPY group allows for an excellent contrast between the dark (reduced) and emissive (oxidized) states, thereby allowing for the high-throughput fluorescence method to be practiced. Both probes have been designed to ensure the efficient photoinduced electron transfer from the chromanol to the BODIPY segment, thereby ensuring an overall sensitivity to the "off-on" probe.

Example 2

ROS Level Establishment

A series of experiments were performed to allow for an assessment as to what degree the presence of a peroxide may contribute to the formation of oxygen/oxygen-species in a particular gel, and to test the for sensitivity of the in vitro release test and the dilution assay.

In a first set of tests to establish the sensitivity of the in vitro release test, samples of the gel A compositions were prepared in which either no oxidant or an oxidant (a peroxide, in the form of UP) was present in an amount as indicated in Table 2 below. The gel samples were placed on the membranes as described in Example 1, and the samples illuminated for a period of 5 minutes, after which an aliquot of the well-solution was taken and analyzed for the amount of ROS present utilizing the ROS test described above. The results are presented in Table 2 below.

TABLE 2

Testing for ROS production using the in vitro release test

| Samples | Average Fluorescence | | Total Fluorescence | ROS µM |
|---|---|---|---|---|
| | With Probe | Without Prob | | |
| Gel A (4.6% UP) | 16000 | 5800 | 10200 | 1.10 |
| Gel A (1% UP) | 16600 | 5790 | 10810 | 1.17 |
| Gel A (0% UP) | 15800 | 5400 | 10400 | 1.12 |

From the results presented in Table 1, it was a determined that while both of the chromophore-containing gel samples that were tested produced ROS, distinguishing between the sample gel having 4.6% UP versus the sample gel containing 1% UP could not be made despite the more than four-fold difference in the amount of UP between the two samples, and furthermore, that the presence of the chromophore may be a substantial contributing factor for the generation of ROS in the gel composition. As such, a second round of testing was performed utilizing the dilution assay methodology (as described above in Example 1) to test for the generation of ROS in illuminated gel samples.

Figure 4A:
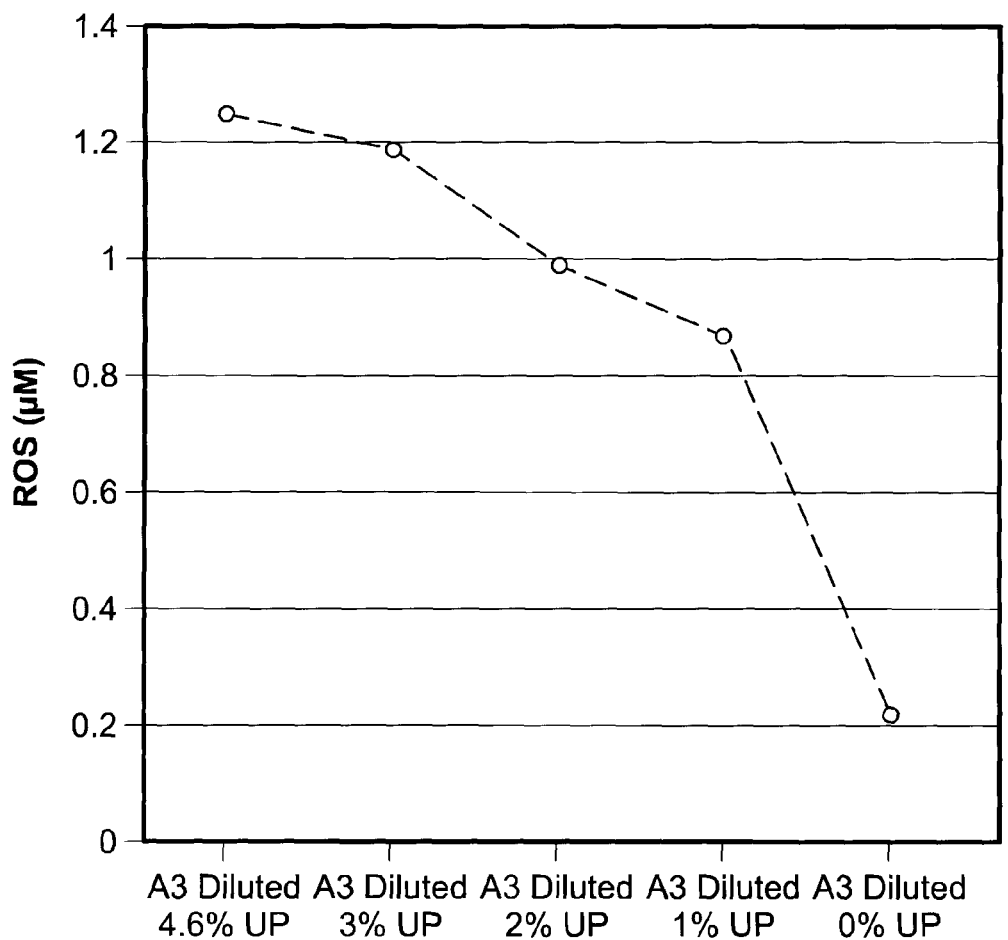
FIGS. 4A and 4B depict reactive oxygen species (ROS) production in a urea peroxide (UP) dilution assay with gel A3 (FIG. 4A) and gel A (FIG. 4B) (Example 2).
Figure 4B:
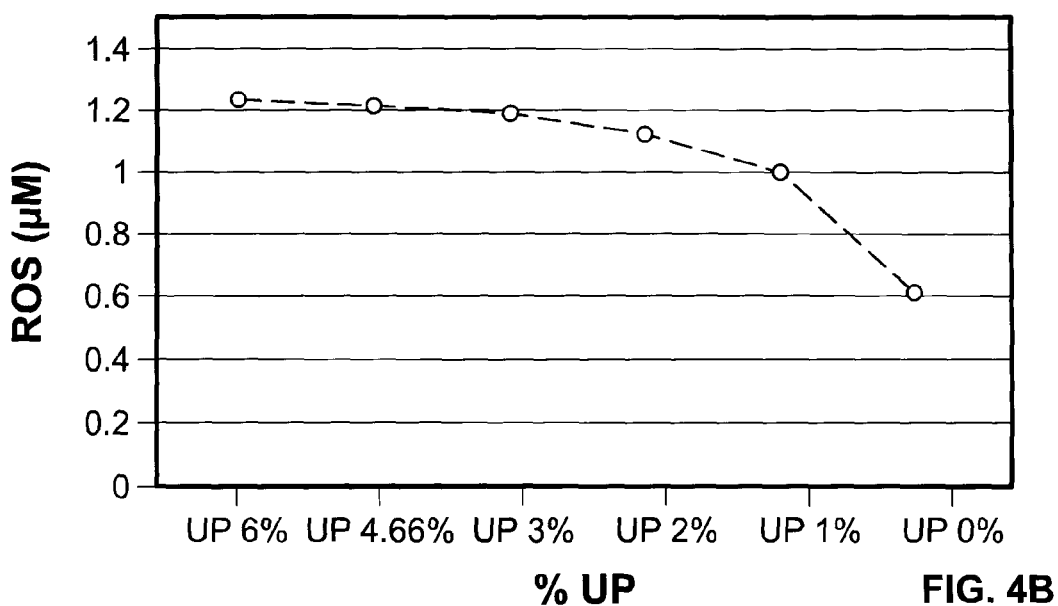

For the second round of testing, a series of gel samples were prepared as listed in Table 3 below; in order to first establish the sensitivity of the assay, the samples comprised the A3 gel (i.e., the A1 gel, but lacking UP unless such was specifically added) alone (lacking the presence of any chromophore) to which the indicated amount of urea peroxide was added (on a % weight basis) or not. Samples of the prepared gel were diluted 1000-fold, and the samples were illuminated for a period of 5 minutes each using the KLOX blue lamp (THERA™) at a distance of 5 cm from the sample, after which the samples (300 µL each) were tested for the presence of ROS. The results are presented below in Table 3 and FIG. 4.

TABLE 3

Testing for ROS production using the dilution assay

| Samples | Average Fluorescence | | Total Fluorescence | ROS µm |
|---|---|---|---|---|
| | With Probe | Without Probe | | |
| Gel A3 (4.6% UP) | 17346 | 5.4 | 16280.6 | 1.26 |
| Gel A3 (3% UP) | 16562 | 7.2 | 15494.8 | 1.20 |
| Gel A3 (2% UP) | 13953 | 8.4 | 12884.6 | 0.99 |
| Gel A3 (1% UP) | 12325 | 10 | 11255 | 0.87 |
| Gel A3 (0% UP) | 4026 | 10.8 | 2955.2 | 0.23 |

As can be seen from Table 3, the sensitivity of the dilution assay enabled a clear distinction to be made as to the level of ROS being produced in the tested gel samples, with a level of ROS being produced progressively increasing with the increase in amount of UP added to the samples of gel A3. As well, as can be seen from FIG. 4A, the impact of adding UP on the amount of ROS produced was evident, and even without the presence of a chromophore in the gel sample, there was still ROS generated upon the gel sample being illuminated.

In a further round of testing, gel A3 samples were prepared as per the second round of testing, however, in this third round of testing, after the liposomes were added to the samples, the samples were left to stand for a period of 5 minutes without being illuminated. Upon completion of the 5 minute incubation period, each of the samples was measured for the amount of ROS produced, and the results and the results are presented below in Table 4.

TABLE 4

Testing for ROS production with dilution assay - no illumination

| Assay Result | Samples | | | | |
|---|---|---|---|---|---|
| | Gel A3 0% UP | Gel A3 1% UP | Gel A3 2% UP | Gel A3 3% UP | Gel A3 4.6% UP |
| Liposome + Probe | 1775.6 | 2301.6 | 2457.2 | 2723.1 | 2496 |
| Liposome | 15.8 | 17.4 | 18.2 | 19.5 | 19.4 |
| Total Fluorescence | 119.8 | 644.2 | 799 | 1063.6 | 836.6 |
| ROS ($\mu$M) | 0.008 | 0.044 | 0.055 | 0.073 | 0.057 |

The results from the third round of testing indicated that increasing the amount of UP in the sample gel resulted in an increase yield of ROS despite the lack of illumination of the gel samples; however, the yield of ROS in the non-illuminated gel samples was considerably less than that which occurred when the gel samples were subject to illumination.

In a fourth round of testing, samples of gel A bearing various amounts of UP were prepared as listed in Table 5 below. Samples were diluted 1000-fold, and after being illuminated for a period of 5 minutes with the KLOX Thera™ light, a 300 µL aliquot of the test gel sample was assayed for the presence of ROS. The results of the testing are presented below in Table 5, and graphically represented in FIG. 4B.

TABLE 5

Testing for ROS production in Gel A

| Assay Result | Gel A (with % UP) | | | | | |
|---|---|---|---|---|---|---|
| | 6% UP | 4.66% UP | 3% UP | 2% UP | 1% UP | 0% UP |
| Liposome + Probe | 17621 | 17995.2 | 17735.9 | 16896.1 | 15414.5 | 10404.9 |
| Liposome | 353.8 | 461.8 | 475.1 | 517 | 579.8 | 644 |
| Total Fluorescence | 15867.2 | 15593.4 | 15320.8 | 14439.1 | 12894.7 | 7820.9 |
| ROS ($\mu$M) | 1.23 | 1.21 | 1.19 | 1.12 | 1.00 | 0.61 |

As can be seen from the results of the fourth round of testing, in comparison to the second round of testing wherein the gel samples lacked the presence of the chromophore, for the fourth round testing sample that had no (0%) UP, there was a substantial difference in the amount of ROS produced compared to the similar sample of the second round testing. The result indicates that having the chromophore present in the gel could affect the amount of ROS that the gel would be capable of producing, and thus, the amount of chromophore would be a factor to be considered in further developing a oxidant-less gel that would be capable of producing a level of ROS at least comparable to that of gel A. Furthermore, it was apparent that there was a plateau effect with respect to the amount of ROS generated versus the concentration of UP in the gel samples tested; for those in this fourth round of testing the plateau level was reached with a range of about 3% to about 6% UP (weight concentration in the gel).

Example 3

Chromophore Concentration for ROS

Figure 5A:
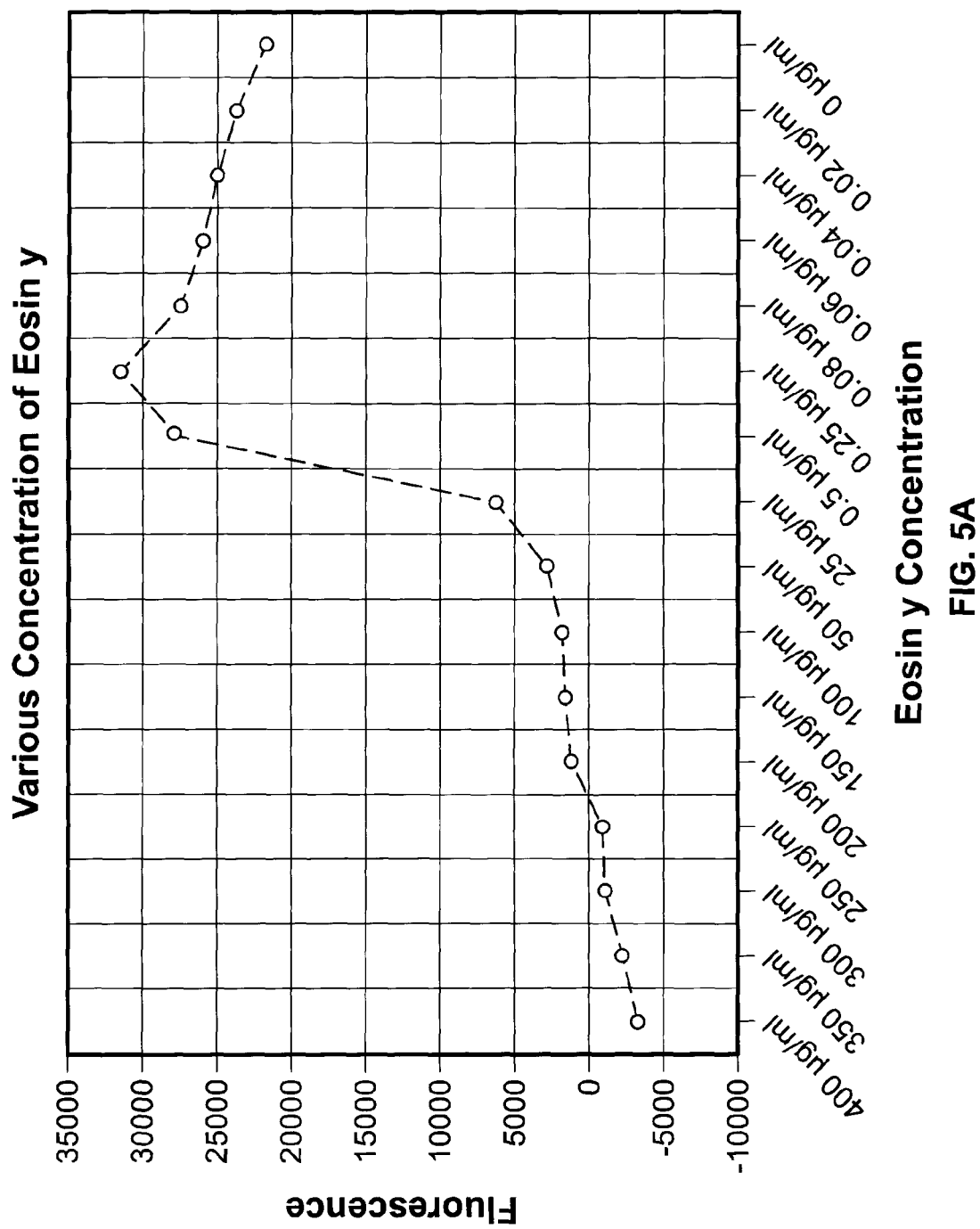
FIGS. 5A, 5B and 5C depict changes in fluorescence with decreasing concentration of Eosin Y in gel A3 (FIGS. 5A and 5B) and the effect of Eosin Y concentration (20×=2,180 µg/g Eosin Y, 10×=1,090 µg/g Eosin Y, and 5×=545 µg/g Eosin Y) on ROS production (FIG. 5C) (Example 3).
Figure 5B:
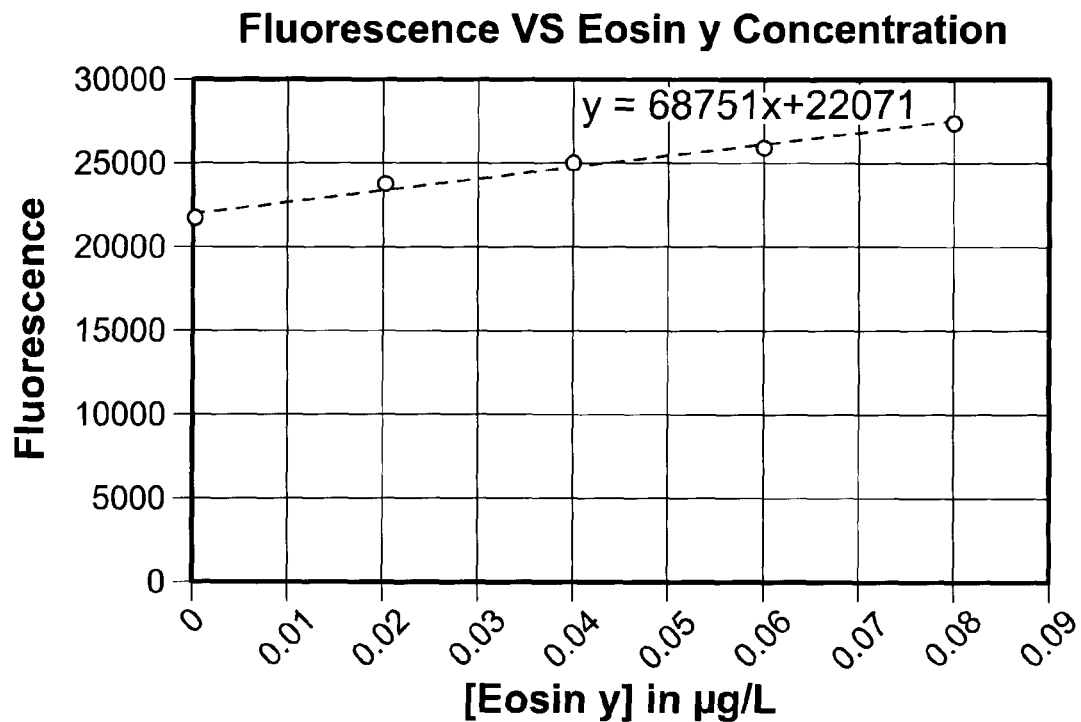
Figure 5C:
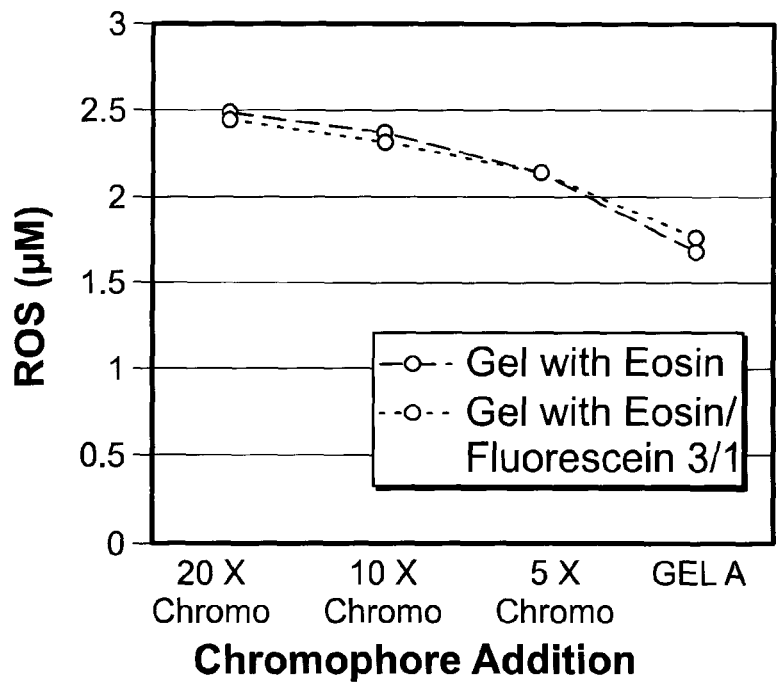

A series of experiments were performed in order to evaluate the effect of altering the amount of a chromophore in a gel composition would have on the ability of the given gel to produce ROS upon being illuminated with the KLOX blue light (THERA™) for a 5 minute illumination time. In a first round of testing, the dilution assay method as described in Example 1 was utilized to assess the level of ROS production: a sample of gel A3 was diluted 10-fold in a PBS solution containing 6% UP, following which, various amounts of a chromophore (either Eosin Y or a combination of Eosin Y and Fluorescein in a 3:1 ratio) ranging from 0 to 400 µg/mL were added. After addition of the chromophore, the gel sample was illuminated with the KLOX blue light (THERA™) at a distance of 5 cm and for a period of 5 minutes. The results are presented below in Table 6 and in FIG. 5.

TABLE 6

Chromophore concentration for ROS production in 10X diluted gel A3 + 6% UP

| [Eosin Y] | Liposome + Probe | Liposome | Total Fluorescence | ROS µM |
|---|---|---|---|---|
| 400 µg/mL | 22706.3 | 24030.5 | neg 3264.2 | BDL |
| 350 µg/mL | 24076.9 | 24402.3 | neg 2265.4 | BDL |
| 300 µg/mL | 24797.3 | 24438.5 | neg 1041.2 | BDL |
| 250 µg/mL | 24594 | 24127.5 | neg 933.5 | BDL |
| 200 µg/mL | 24609 | 21986.7 | 1222.3 | 0.10 |
| 150 µg/mL | 20113.5 | 17059.2 | 1654.3 | 0.13 |

TABLE 6-continued

Chromophore concentration for ROS production in 10X diluted gel A3 + 6% UP

| [Eosin Y] | Liposome + Probe | Liposome | Total Fluorescence | ROS μM |
|---|---|---|---|---|
| 100 μg/mL | 18311.7 | 15123 | 1788.7 | 0.14 |
| 50 μg/mL | 19562.5 | 14873.5 | 2749 | 0.21 |
| 25 μg/mL | 21444.1 | 13195.4 | 6308.7 | 0.49 |
| 0.5 μg/mL | 33375.4 | 3758 | 27677.4 | 2.15 |
| 0.25 μg/mL | 35622 | 2138 | 31544 | 2.45 |
| 0.08 μg/mL | 29150.6 | 250.3 | 27500.3 | 2.14 |
| 0.06 μg/mL | 27610.6 | 193.7 | 26016.9 | 2.02 |
| 0.04 μg/mL | 26605.2 | 140.3 | 25064.9 | 1.95 |
| 0.02 μg/mL | 25254.3 | 77.9 | 23776.4 | 1.85 |
| 0 μg/mL | 23161 | 15.5 | 21745.5 | 1.69 |

BDL = Below Detection Limit (0.01 μM) of the instrument

From the results presented in Table 6, it was apparent that at a concentration of chromophore above 0.5 μg/mL, diminishing amounts of ROS were being produced in the illuminated gel samples. The diminished output of ROS at the higher concentration levels of the chromophore were indicative of a fluorescence quenching (due to the elevated level of the chromophore). Furthermore, from a range of 50 μg/mL to 0.25 μg/mL of the chromophore, the fluorescence increased with the decreasing the concentration of chromophore, and thereafter decreased with a decreasing chromophore concentration from 0.08 μg/mL to the no chromophore containing test sample. The results are also represented graphically in FIG. 5A, and also in FIG. 5B where a linear relationship can be observed between 0.08 μg/mL and 0 μg/mL. The results from this first round of testing thus indicated that while adding a chromophore to the gel mixture could aid in increasing the level of ROS production, only a limited amount of a chromophore could be added before a negative impact on ROS production would occur.

Further testing, again utilizing the dilution assay methodology, of the chromophore concentration for ROS production was done utilizing a series of PBS-diluted gels (diluted over a range of concentrations as seen in Table 7 below) bearing various amounts of either a single chromophore (Eosin Y) or a mixture of chromophores (a 3:1 mixture of Eosin Y and Fluorescein). The results are presented below in Table 7, and also in FIG. 5C.

TABLE 7

ROS production with varying the level of chromophore in a gel A composition

| Sample | Dilution Factor | Liposome + Probe | Liposome | Total Fluorescence | ROS (μM) |
|---|---|---|---|---|---|
| Gel A - 20X EY | 1600X | 41254.3 | 3510.8 | 35743.5 | 2.10 |
| Gel A - 10X EY | 1600X | 43321 | 1962.8 | 41358.2 | 2.43 |
| Gel A - 20X EY | 2400X | 42197.8 | 2685 | 39512.8 | 2.32 |
| Gel A - 10X EY | 2400X | 43109.5 | 1387.5 | 41722 | 2.45 |
| Gel A - 20X EY | 4000X | 44248.6 | 1921.2 | 42327.4 | 2.49 |
| Gel A - 10X EY | 4000X | 41332.6 | 941.2 | 40391.4 | 2.38 |
| Gel A - 5X EY | 4000X | 37090.4 | 606.3 | 36484.1 | 2.15 |
| Gel A | 4000X | 28989.5 | 279.8 | 28709.7 | 1.69 |
| Gel A - 20X EY/F | 4000X | 42967.3 | 1304.1 | 41663.2 | 2.45 |
| Gel A - 10X EY/F | 4000X | 40325 | 788.8 | 39536.2 | 2.33 |
| Gel A - 5X EY/F | 4000 x | 36902.6 | 491.1 | 36411.5 | 2.14 |
| Gel A - 1X EY/F | 4000X | 30355.6 | 281.6 | 30074 | 1.77 |

As observed from the results, while a greater amount of ROS was generated at chromophore concentrations of over 5-times the chromophore concentration present in gel A, it was unnecessary to go beyond 5-times the chromophore concentration, in either the single chromophore sample gel or in the chromophore mixture sample gel, in order to obtain a comparable level of ROS production to gel A.

Example 4

Illumination Effect on ROS Production

To test the effect that altering the length of the illumination period may have on the production of ROS in a given gel composition, a sample of gel B having 18.1 mg/g of carbopol in the mixture was prepared. For comparative testing to evaluate the effect of having a chromophore present in the gel mixture along with altering the illumination period, a chromophore (Eosin Y) was also added to the sample gel to be tested, as listed below:

Sample 1: Gel B, 2 cm high, 2 minutes illumination, no UP

Sample 2: Gel B, 2 cm high, 5 minutes illumination, no UP

Sample 3: Gel B, 2 cm high, 10 minutes illumination, no UP

Sample 4: Gel B+EY @ 20 μg/mL, 2 cm high, 2 minutes illumination, no UP

Sample 5: Gel B+EY @ 20 μg/mL, 2 cm high, 5 minutes illumination, no UP

Sample 6: Gel B+EY @ 20 μg/mL, 2 cm high, 10 minutes illumination, no UP

The samples were tested using the dilution assay described in Example 1. Results from the testing of the gel samples are presented in Table 8 below.

TABLE 8

ROS production in Gel B-varying illumination time

| Sample | Liposome + Probe | Liposome | Total Fluorescence | ROS (μM) |
|---|---|---|---|---|
| S1 | 2542.7 | 40.2 | 1302.5 | 0.08 |
| S2 | 7634.6 | 22.7 | 6411.9 | 0.39 |
| S3 | 10153.3 | 15.8 | 8937.5 | 0.54 |
| S4 | 17625.7 | 3393 | 13032.7 | 0.79 |
| S5 | 39817.8 | 2344 | 36273.8 | 2.20 |
| S6 | 40285.6 | 1272.2 | 37813.4 | 2.29 |

As can be seen in comparing sample 1 to sample 6, the production of ROS was proportional to the illumination time, and could be enhanced by having a chromophore present in the gel mixture.

In a second round of testing, again using the dilution assay described in Example 1, the following samples were evaluated for their ability to produce ROS upon being illuminated for the noted time period with the light source place consistently at 5 cm distance from the tested sample to be illuminated. Samples were prepared as listed below, and those samples denoted with an "n1" and "n2" are replicate samples, and the gel sample numbered 5 to 11 were diluted 1000-fold in PBS prior to testing:

Sample 1: Gel A, 12% UP, 5 minutes illumination

Sample 2: Light alone, 9 minutes illumination (n1)

Sample 3: Light alone, 9 minutes illumination (n2)

Sample 4: Mix of Gel A3+Gel A4, 9 minutes illumination (n1)

Sample 5: Mix of Gel A3+Gel A4, 9 minutes illumination (n2)

Sample 6: Mix of Gel A2+Gel A3, 9 minutes illumination (n1)

Sample 7: Mix of Gel A2+Gel A3, 9 minutes illumination (n2)
Sample 8: Gel A4, 9 minutes illumination (n1)
Sample 9: Gel A4, 9 minutes illumination (n2)
Sample 10: Gel A2 (12% UP), 9 minutes illumination (n1)
Sample 11: Gel A2 (12% UP), 9 minutes illumination (n2)

Results from the testing of the gel samples are presented below in Table 9.

TABLE 9

Illumination of various gel compositions - ROS yield

| Sample | Liposome + Probe | Liposome | Total Fluorescence | ROS (μM) |
|---|---|---|---|---|
| S 1 | 28118.6 | 951.5 | 26197.1 | 1.52 |
| S 2 | 7529.6 | 10.3 | 6549.3 | 0.38 |
| S 3 | 7203.2 | 11.8 | 6221.4 | 0.36 |
| S 4 | 8022.3 | 15.5 | 7036.8 | 0.41 |
| S 5 | 7836.6 | 14.5 | 6852.1 | 0.40 |
| S 6 | 25668.1 | 871 | 23827.1 | 1.38 |
| S 7 | 24538.9 | 838.1 | 22730.8 | 1.32 |
| S 8 | 21582 | 9 | 20603 | 1.19 |
| S 9 | 20864.2 | 32.9 | 19861.3 | 1.15 |
| S 10 | 31774.4 | 290.7 | 30513.7 | 1.77 |
| S 11 | 30539.7 | 314.5 | 29255.2 | 1.70 |

Regarding samples 2 and 3, illumination of the liposome-containing solution alone (without any gel added) provided a base number of ROS production, and addition of gel lacking any added chromophore or UP only resulted in a marginal increase in the amount of ROS generated (see samples 4 and 5). Addition of chromophore to the gel composition (having other components added as well) resulted in an increase in ROS production (see samples 6 and 7) when compared to an equivalent gel composition lacking the chromophores (see samples 8 and 9), and this effect was magnified with the addition of the oxidant to the gel composition (see samples 10 and 11), such levels of ROS production being comparable to the level of ROS production of gel A.

Example 5

Component Testing

In a next phase of testing, a series of experiments were performed, utilizing the dilution assay described in Example 1, to evaluate whether various components of a gel A composition (as described in Example 1), or other various possible chemical additives, may affect the ability of a gel composition to produce ROS and to what level, upon the given gel composition being illuminated for a specific period of time (e.g. either 5 or 9 minutes). Given that gel B, comprising water plus 18.1 mg/g of carbopol had the fewest constituent components, gel B was utilized as the denominator gel to which various chemical compounds were added (e.g., gel B+chemical compound A (plus, optionally, chemical compound "a", "b", "c", etc.)) in order to individually evaluate the particular candidate chemical. For the addition of glycerin, when added, the amount was 44.2 g (for a 100 g weight of gel) and for propylene glycol (PG), the amount added was 15.4 g (for a 100 g weight of gel). As well, for comparative purposes, the tested samples also included those to which various amounts of UP and/or a chromophore were added either as a single chromophore or in combination with another chromophore. For most gel samples, testing was performed in replicate for the given sample.

In a first round of testing, the following gel samples with the noted additional chemical compound or compounds tested for the ability of the given gel composition to produce ROS:
Sample 1: Gel B+5% Sodium Bicarbonate (SB), 5 minutes illumination (20× dilution)
Sample 2: Gel A2+5% Sodium Bicarbonate, 5 minutes illumination (20× dilution)
Sample 3: Gel A2, 5 minutes illumination (20× dilution)
Sample 4: Gel B+1× Eosin Y, 5 minutes illumination (1000× dilution)
Sample 5: Gel B+Glycerin+1× Eosin Y, 5 minutes illumination (1000× dilution)
Sample 6: Gel B+Propylene Glycol (PG)+1× Eosin Y, 5 minutes illumination
Sample 7: Gel B+Glycerin+PG+1× Eosin Y, 5 minutes illumination
Sample 8: Gel A3+A4+1% UP, 9 minutes illumination
Sample 9: Gel A3+A4+3% UP 9 minutes illumination
Sample 10: Gel A3+A4+6% UP, 9 minutes illumination
Sample 11: Gel A3+A4+12% UP, 9 minutes illumination
Sample 12: Gel A3+A4, 2× Eosin Y, 9 minutes illumination (n1)
Sample 13: Gel A3+A4, 2× Eosin Y, 9 minutes illumination (n2)
Sample 14: Gel A3+A4+12% UP) 2× Eosin Y, 9 minutes illumination (n1)
Sample 15: Gel A3+A4+12% UP) 2× Eosin Y, 9 minutes illumination (n2)
Sample 16: Gel A3+A4+1% UP) 2× Eosin Y, 9 minutes illumination (n1)
Sample 17: Gel A3+A4+3% UP) 2× Eosin Y, 9 minutes illumination (n1)
Sample 18: Gel A3+A4+6% UP) 2× Eosin Y, 9 minutes illumination (n1)
Sample 19: Gel A3+A4+9% UP, 2× Eosin Y, 9 minutes illumination (n1)
Sample 20: Light+1% UP, 9 minutes illumination (n1)
Sample 21: Light+1% UP, 9 minutes illumination (n2)
Sample 22: Light+3% UP, 9 minutes illumination (n1)
Sample 23: Light+3% UP, 9 minutes illumination (n2)
Sample 24: Light+6% UP, 9 minutes illumination (n1)
Sample 25: Light+6% UP, 9 minutes illumination (n2)
Sample 26: Light+8% UP, 9 minutes illumination (n1)
Sample 27: Light+8% UP, 9 minutes illumination (n2)
Sample 28: Light+12% UP, 9 minutes illumination (n1)
Sample 29: Light+12% UP, 9 minutes illumination (n2)

Results from the aforementioned round of testing are presented below in Table 10.

TABLE 10

ROS production - testing of gel samples having added components

| Sample | Liposome + Probe | Liposome | Total Fluorescence | ROS (μM) |
|---|---|---|---|---|
| S 1 | 3538.2 | 69 | 1069.2 | 0.06 |
| S 2 | 14121.1 | 48 | 11673.1 | 0.61 |
| S 3 | 7091.7 | 41.4 | 4650.3 | 0.25 |
| S 4 | 10471.2 | 1185.3 | 6885.9 | 0.36 |
| S 5 | 11295.1 | 1248.8 | 7646.3 | 0.40 |
| S 6 | 10547.9 | 1237.8 | 6910.1 | 0.36 |
| S 7 | 9992.2 | 1200.1 | 6392.1 | 0.34 |
| S 8 | 11497.3 | 13 | 9084.3 | 0.48 |
| S 9 | 17668.3 | 11.2 | 15257.1 | 0.80 |
| S 10 | 25620.6 | 7.2 | 23213.4 | 1.22 |
| S 11 | 28344.2 | 9.3 | 25934.9 | 1.37 |
| S 12 | 31459 | 2442.6 | 26616.4 | 1.40 |

TABLE 10-continued

ROS production - testing of gel samples having added components

| Sample | Liposome + Probe | Liposome | Total Fluorescence | ROS (µM) |
|---|---|---|---|---|
| S 13 | 32793.1 | 2274.9 | 28118.2 | 1.48 |
| S 14 | 24402.1 | 1289.2 | 20712.9 | 1.09 |
| S 15 | 23484.9 | 1309.4 | 19775.5 | 1.04 |
| S 16 | 31638.6 | 1757.5 | 27481.1 | 1.45 |
| S 17 | 29763.1 | 1707.7 | 25655.4 | 1.35 |
| S 18 | 25703.2 | 1583.3 | 21719.9 | 1.14 |
| S 19 | 27288.9 | 701.7 | 24187.2 | 1.27 |
| S 20 | 9492.6 | 654.5 | 6438.1 | 0.34 |
| S 21 | 9806.6 | 9.8 | 7396.8 | 0.39 |
| S 22 | 11624.4 | 8.2 | 9216.2 | 0.49 |
| S 23 | 11137.3 | 10.1 | 8727.2 | 0.46 |
| S 24 | 12036.9 | 9 | 9627.9 | 0.51 |
| S 25 | 12976.1 | 7.1 | 10569 | 0.56 |
| S 26 | 16170.2 | 8.5 | 13761.7 | 0.72 |
| S 27 | 16654.8 | 8.3 | 14246.5 | 0.75 |
| S 28 | 18911.1 | 8.7 | 16502.4 | 0.87 |
| S 29 | 18668.3 | 10.2 | 16258.1 | 0.86 |

The results from the first round of testing were inconclusive, though with respect to an addition of 5% sodium bicarbonate (SB) (and an illumination time of 5 minutes), comparing the result for samples 1, 2 and 4, there was a difference between the samples that may have been due to having additional factors other than the presence of having a chromophore in the gel composition when the sodium bicarbonate was present in the composition. When added alone or in combination to gel B, glycerin and PG did not appear to have any effect (see samples 4 to 7) even though the chromophore was added to the gel as well. When increased amounts of UP alone were added to gel B, the yield of ROS also increased (see samples 8 to 11 and samples 20 to 29), with a similar effect occurring when a greater amount of chromophore was also present in the gel B (see samples 14 to 19).

In a second round of testing, the following samples tested for the ability of the given gel composition to produce ROS:

Sample 1: Gel B+5× Eosin Y, 10 minutes illumination

Sample 2: Gel B, 10 minutes illumination

Sample 3: Gel B+10% Sodium Bicarbonate, 10 minutes illumination (i.e. a Gel C).

Sample 4: Gel B+Glucosamine, 10 minutes illumination

Sample 5: Gel B+Propyl paraben, 10 minutes illumination

Sample 6: Gel A, 2× Eosin Y, 9 minutes illumination (n1) (2000× dilution)

Sample 7: Gel A, 2× Eosin Y, 9 minutes illumination (n2) (2000× dilution)

Sample 8: Gel A, 2× Eosin Y, 9 minutes illumination (2000× dilution)

Sample 9: Gel A, 6% UP, 2× Eosin Y, 9 minutes illumination (2000× dilution)

Sample 10: Gel A, 1% UP, 2× Eosin Y, 9 minutes illumination (2000× dilution)

Sample 11: Gel A1+A4, 12% UP, 9 minutes illumination

Sample 12: Gel A1+A4, 12% UP, 9 minutes illumination

Sample 13: PBS+Liposome-Probe standing for 9 minutes, no illumination (n1)

Sample 14: PBS+Liposome-Probe standing for 9 minutes, no illumination (n2)

Results from the testing of this second round of gel samples are presented below in Table 11.

TABLE 11

ROS production testing of gel samples having added components

| Sample | Liposome + Probe | Liposome | Total Fluorescence | ROS (µM) |
|---|---|---|---|---|
| S 1 | 17150.2 | 245.8 | 15204.4 | 0.94 |
| S 2 | 7229.9 | 17.2 | 5512.7 | 0.34 |
| S 3 | 29272.3 | 20.7 | 27551.6 | 1.70 |
| S 4 | 7758.5 | 15.7 | 6042.8 | 0.37 |
| S 5 | 10776.8 | 16.2 | 9060.6 | 0.56 |
| S 6 | 24989.2 | 145.5 | 23143.7 | 1.42 |
| S 7 | 24463.2 | 143.7 | 22619.5 | 1.39 |
| S 8 | 24028.6 | 181.6 | 22147 | 1.36 |
| S 9 | 20629.6 | 218 | 18711.6 | 1.15 |
| S 10 | 16597.5 | 432.4 | 14465.1 | 0.89 |
| S 11 | 27567 | 11.3 | 25855.7 | 1.59 |
| S 12 | 25200.5 | 13.4 | 23487.1 | 1.45 |
| S 13 | 1915.8 | 31.1 | 184.7 | 0.01 |
| S 14 | 1999.1 | 34.5 | 264.6 | 0.02 |

From the second round of testing, wherein a longer illumination period was utilized than in the first round of testing, adding 5× extra chromophore to the gel B composition resulted, not surprisingly, to a yield of ROS that was higher than with only 1× chromophore (see samples 1 and 2, and compare to the round 1 testing). Quite surprising, however, was the amount of ROS produced when the 10% sodium bicarbonate alone was added to the gel B composition and the composition (gel C) thereafter illuminated for the 10 minute period (see sample 3). Addition of glucosamine or propyl parabens alone did not have an effect (see samples 6 and 7, compared to sample 2). The result obtained with the addition of the 10% sodium bicarbonate was even greater than that obtained when the gel A was tested with twice the amount of chromophore present in the gel A composition (see sample 3 compared to samples 6 to 8 (and 9 and 10 with lower levels of UP)) or a composition comprising gels A1+A4 with 12% UP in the mixture.

In a third round of testing, an effect of having several components concomitantly in a gel B composition was tested, in comparison to a diluted gel A composition and a gel composition comprising gel A2+A3 to which a chromophore was added. The gels tested are noted below:

Sample 1: Gel A, 1000 time dilution, 5 minutes illumination

Sample 2: Gel A2+A3, 1000 times diluted, 5 minutes illumination

Sample 3: Gel B+Glycerin, 3× Eosin Y+1% Sodium Bicarbonate, 10 minutes illumination Results from the testing of this third round of gel samples are presented below in Table 12.

TABLE 12

ROS production testing of gel samples having added components

| Sample | Liposome + Probe | Liposome | Total Fluorescence | ROS (µM) |
|---|---|---|---|---|
| S 1 | 20315 | 557.8 | 16757.2 | 1.22 |
| S 2 | 17439 | 1253.2 | 12185.8 | 0.86 |
| S 3 | 25330.4 | 1303.4 | 20227 | 1.42 |

As observed from the results, the ROS produced by the 10 minute-illuminated gel composition of sample 3, was greater than that of the gel A, although the sample 3 gel was illuminated for a longer period of time than the sample 1 gel.

In a fourth round of testing, similar to the third round of testing, an effect of having several components concomitantly in a gel B composition was tested, in comparison to a diluted gel A composition or gel composition similar to gel A but lacking UP. The tested gel compositions are noted below:

Sample 1: Gel A2+A3, 1000× dilution, 5 minutes illumination

Sample 2: Gel A (12% UP), 1000× dilution, 5 minutes illumination

Sample 3: Gel A3+A4, 1× Fluorescein, 5 minutes illumination

Sample 4: Gel B+Glycerin+3× Eosin Y, 10 minutes illumination

Sample 5: Gel B+Glycerin+SOD (1 mg/ml)+3× Eosin Y, 10 minutes illumination

Sample 6: Gel B+Glycerin (which thus forms a Gel D1)+1% Sodium Bicarbonate+3× Eosin Y, 10 minutes illumination Sample 7: Gel A3+SOD (1 mg/ml)+3× Eosin Y, 10 minutes illumination Sample 8: Gel A3+1% Sodium Bicarbonate+3× Eosin Y, 10 minutes illumination Sample 9: Gel A3+3% Sodium Bicarbonate+3× Eosin Y, 10 minutes illumination Sample 10: Gel A4+SOD (1 mg/ml)+3× Eosin Y, 10 minutes illumination Sample 11: Gel A4+1% Sodium Bicarbonate+3× Eosin Y, 10 minutes illumination Results from the testing of this fourth round of gel samples are presented below in Table 13.

TABLE 13

ROS production testing of gel samples having added components

| Sample | Liposome + Probe | Liposome | Total Fluorescence | ROS (μM) |
|---|---|---|---|---|
| S 1 | 18848.7 | 2017.2 | 14611.5 | 0.94 |
| S 2 | 26492.8 | 443 | 23829.8 | 1.54 |
| S 3 | 17067 | 1048.3 | 13798.7 | 0.89 |
| S 4 | 26795.3 | 1317.4 | 23257.9 | 1.50 |
| S 5 | 24534.5 | 572.5 | 21742 | 1.40 |
| S 6 | 29503.6 | 1610 | 25673.6 | 1.66 |
| S 7 | 17158.1 | 492.8 | 14445.3 | 0.93 |
| S 8 | 34519.1 | 3273.9 | 29025.2 | 1.87 |
| S 9 | 33136.5 | 3371.7 | 27544.8 | 1.78 |
| S 10 | 14407.2 | 738.7 | 11448.5 | 0.74 |
| S 11 | 33464.1 | 2869.1 | 28375 | 1.83 |

As observed from the result with respect to sample 4, an addition of glycerin along with having an elevated amount of chromophore in the gel B composition yielded an ROS production level similar to that of the gel A composition that contained chromophore plus the oxidant; this comparative difference was also observed in the third round of sample testing. As well, with the presence of an amount of sodium bicarbonate in the gel B composition along with the glycerin and elevated chromophore amount, a greater ROS production level was reached (see sample 6). Regarding samples 8 and 9, a higher ROS level was also achieved with these gels compositions in comparison to the gel composition of sample 2. Addition of an $O_2^-$ metabolizing enzyme, superoxide dismutase (SOD), in the gel compositions tested in this fourth round of testing, did not appear to have an impact on an amount of ROS that the given gel sample could produce.

Example 6

Scaling of Bicarbonate

As the results indicated that addition of bicarbonate to gel composition could positively impact an amount of ROS produced by an illuminated gel, a further set of experiments were carried out in order to evaluate concentrations of sodium bicarbonate added in the D1 gel that would result in a creation of hydrogen peroxide in the gel over the 10 minute course of the gel being illuminated. The objective was that of determining the range of bicarbonate concentrations that could be used in order to minimize hydrogen peroxide production while providing for an adequate level of production of oxygen/oxygen-species from the illuminated gel. Gel compositions akin to those of Example 5, third round sample gel 3 and fourth round 6, were evaluated when having an added sodium bicarbonate amount that ranged from 1% to 20% (per weight of the gel composition).

Gel D1 samples were prepared having 3× chromophore, and after being illuminated for the above-noted time period, aliquots of the test gel sample were assayed for their hydrogen peroxide content using a Pierce Quantitative Peroxide Assay Kit (Product No. 23280, Pierce Biotechnology, Rockford, Ill., USA). Briefly, the methodology for the Pierce assay kit allows for a detection of peroxide based on oxidation of ferrous to ferric ion in the presence of xylenol orange; the sensitivity of the detection procedure is enhanced through the use of an aqueous-compatible formulation that includes sorbitol. In the assay, hydroperoxides convert the $Fe^{2+}$ to $Fe^{3+}$ at acidic pH, and with the aqueous-compatible formulation, peroxide first reacts with sorbitol, converting it to a peroxyl radical, which in turn initiates $Fe^{2+}$ oxidation to $Fe^{3+}$. In a sulfuric acid solution (supplied as part of the kit), the $Fe^{3+}$ complexes with the xylenol orange dye to yield a purple product with a maximum absorbance at 560 nm. Based on a standard curve from the absorbance measurement of a standardized reaction utilizing a dilution series from a 1000 μM $H_2O_2$ solution, the amount of hydrogen peroxide in a test solution(s) can be plotted utilizing the absorbance readings from the test samples, and the amount of $H_2O_2$ in the test sample quantitatively determined.

To perform the Pierce assay, a working reagent (WR) is prepared by mixing 1 volume of the kit-supplied Reagent A (a 1 mL composition: 25 mM ammonium ferrous (II) sulfate, 2.5 M $H_2SO_4$) with 100 volumes of the kit-supplied Reagent B (2×50 mL composition: 100 mM sorbitol, 125 μM xylenol orange in water). At least 1 mL of WR is prepared for each sample to be tested. For preparation of the peroxide standard, a 30% (8.8 M) hydrogen peroxide stock solution is serially diluted in ultrapure water to obtain 8-10 standards in a concentration range of 1-1000 μM. Upon completion of the test sample's treatment procedure (this being the illumination of the given gel sample), 10 volumes of WR are added to 1 volume of the sample, and the assay sample contents are mixed and incubated for 15-20 minutes at room temperature (the incubation step is necessary for the reaction to reach an endpoint and form a stable complex). The absorbance of assay samples were taken at 560 nm in a spectrophotometer, and the concentration of peroxide in each of the assay samples was calculated by reference to its assay absorbance compared to the standard curve from the peroxide standard. The results from the experiment are described below.

The tested samples were first evaluated visually, and for the test sample gels having the 1% to 4% sodium bicarbonate range, upon mixing with the WR, the respective solutions changed color either not at all to only very slightly, to a yellowish-to-brownish color. The test sample gel having a 5% sodium bicarbonate the solution turned a deep blue, while the test sample gel having the 7.5% sodium bicarbonate was violet, and the for test gel samples that were in the 10% to 20% sodium bicarbonate amount range, these turned a deep purple color on being mixed with the WR solution. Given that the indicator dye is supposed to change from a yellow color to a purple color in the presence of hydrogen peroxide it was clear that 7.5% (and higher) sodium bicarbonate test samples had hydrogen peroxide present in them.

Figure 6A:
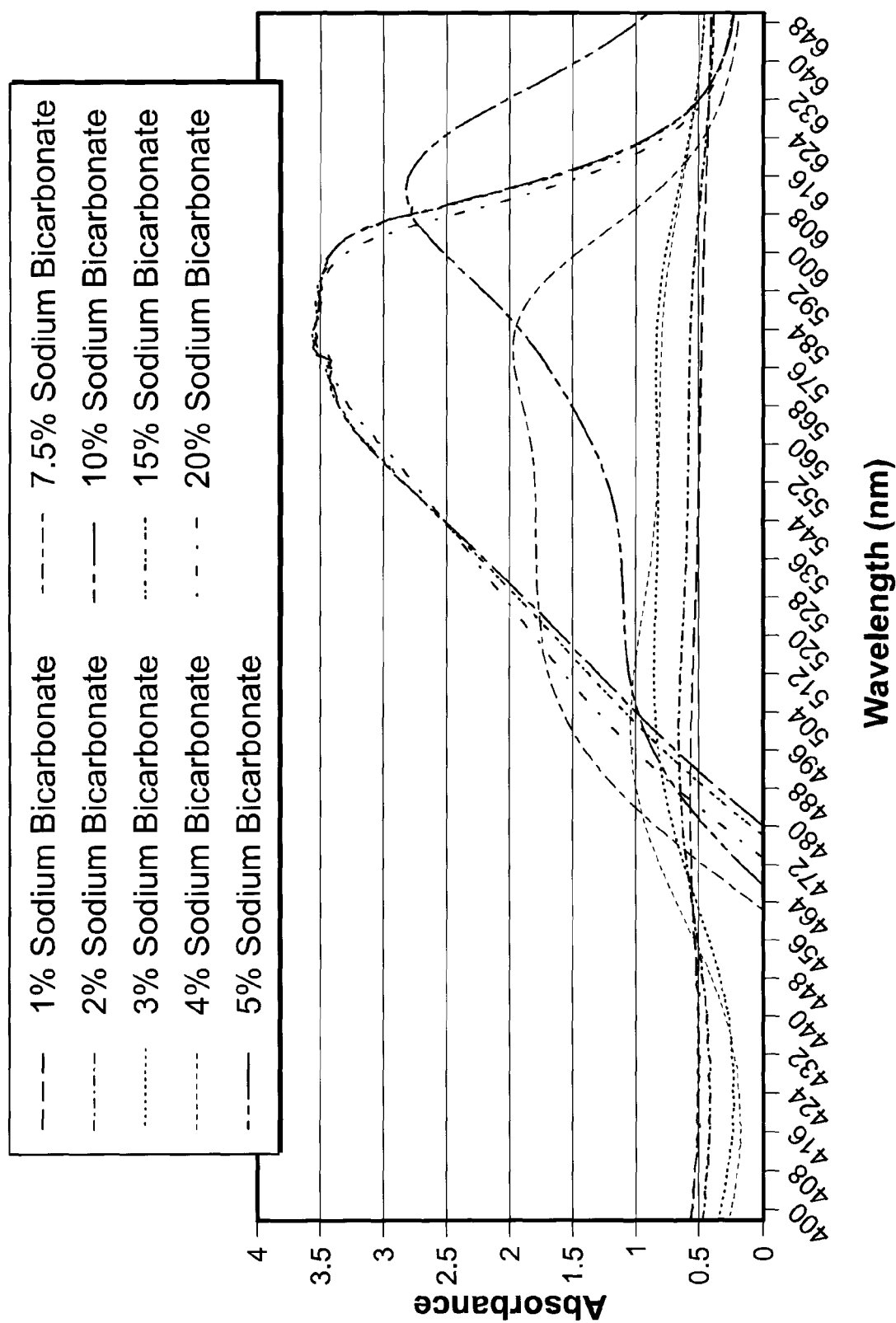
FIGS. 6A and 6B depict the production of hydrogen peroxide in gel D1 in the presence of varying concentrations of sodium bicarbonate (Example 6). 109, 327, 545, and 763 µg/g of Eosin Y (labelled as 1×, 3×, 5×, and 7× respectively)
Figure 6B:
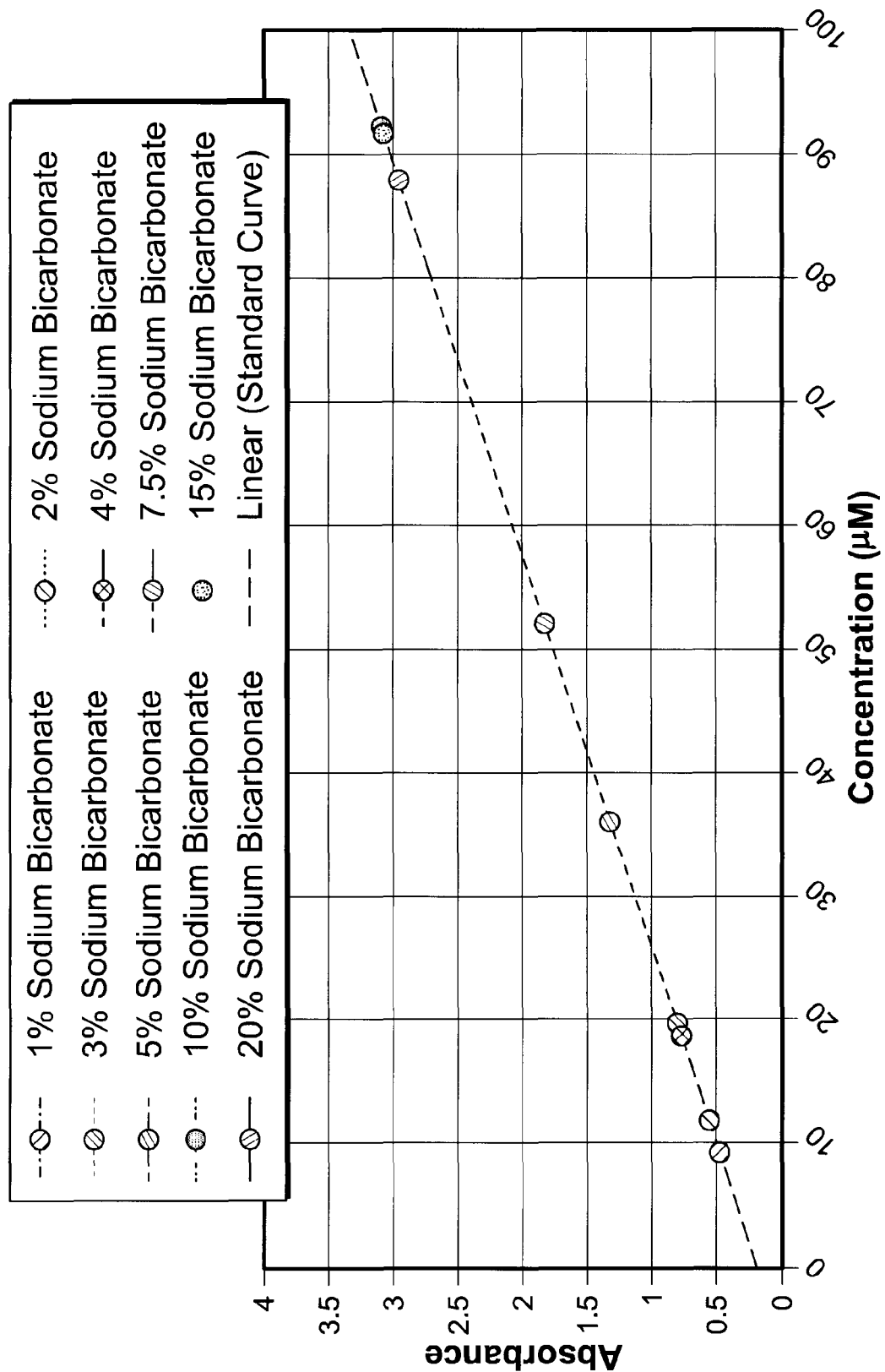

Upon completion of the visual inspection, the test sample solutions were then measured for their absorbance at 560 nm (see FIG. 6A) and the absorbance reading converted into a concentration value (see FIG. 6B and Table 14). From this data, it was evident that an addition of an amount of sodium bicarbonate in the range of about 1% to about 4% resulted in less than 20 µM hydrogen peroxide production in the illuminated gel. At 5% sodium bicarbonate, there was about 36 µM hydrogen peroxide produced, and at 7.5% sodium bicarbonate resulted in a 52 µM amount of hydrogen peroxide. With 10% sodium bicarbonate or more, the hydrogen peroxide level values exceeded the standard curve, however, by using the scan data to extrapolate an approximate amount of hydrogen peroxide production (at 10% sodium bicarbonate addition) a value of about 90 µM hydrogen peroxide resulted.

TABLE 14

Scaling of Bicarbonate to detect $H_2O_2$ presence

| % Sodium Bicarbonate in D1 gel | Absorbance @560 nm | Dilution factor | $[H_2O_2]$ (µM) | Absorbance @560 nm Recalculated | $[H_2O_2]$ (µM) Recalculated |
|---|---|---|---|---|---|
| 1% | 0.4753 | | 9.12 | | |
| 2% | 0.5604 | | 11.83 | | |
| 3% | 0.8054 | | 19.63 | | |
| 4% | 0.7776 | | 18.75 | | |
| 5% | 1.3208 | | 36.04 | | |
| 7.50% | 1.8241 | | 52.07 | | |
| 10% | 3.0845 | | 92.21 | | |
| 15% | 3.0675 | | 91.67 | | |
| 20% | 2.9518 | | 87.98 | | |
| 7.5% (diluted) | 0.129 | 5 | | 1.8241 | 52.07 |
| 10% (diluted) | 0.3732 | 5 | | 5.277163721 | 162.04 |
| 15% (diluted) | 0.4097 | 5 | | 5.793285039 | 178.48 |
| 20% (diluted) | 0.3826 | 5 | | 5.410082636 | 166.28 |

To conclude, until at least an amount about 5% sodium bicarbonate (w/w) was added, an addition of sodium bicarbonate did not result in any significant production of hydrogen peroxide from the illuminated D1 gel. Moving up to an amount of 10% sodium bicarbonate greatly increased the amount of hydrogen peroxide.

PART B. Fluorescence Determination

Example 7

Bicarbonate and Glycerin (Glycerol) Effect

Results from the experiments directed towards evaluating the effect that individual ingredients, when added alone or in combination, may have on the ability of the gel to produce ROS when illuminated with an actinic light source (the KLOX multi-LED lamp emitting blue light) indicated that the addition of sodium bicarbonate, and glycerin in the presence of an elevated amount of chromophore, could result in an ROS level comparable or above an oxidant-containing biophotonic gel composition such as that of gel A.

To evaluate the effect of particular components on the ability of the oxidant-less gel composition to yield an adequate fluorescence spectrum production (both in terms of an overall amount of fluorescence and a spectrum of colors in the visible light range), when the given oxidant-less gel either has or lacked a bicarbonate (such as sodium bicarbonate), further tests were conducted in solution to see if ingredients would have a amplifying or synergistic effect to the added sodium bicarbonate.

Using gel B with 3× eosin Y and 1% sodium bicarbonate (i.e. gel C), having either a blank (no glycerin added) versus a glycerin-added (i.e. to form a gel D1) aliquot samples were tested for their fluorescence. To test the samples for their fluorescence yield, an aliquot of the given gel sample was taken (approximately 2 mL) and placed in a circular well device that has a 2 mm depth inscribed thereupon (the gel is loaded into the well in order to completely fill (with no air pockets remaining) the well up to the 2 mm depth line) and the device is placed upon a glass slide mounted above a SP-100 photodetector (CSA Group/ORB Optronix (Washington state, USA, Kirkland, 98033); once prepared, the gel was illuminated using the KLOX multi-LED blue light (THERA™), positioned at 5 cm from the gel sample, for a pre-set time (typically either 5 or 10 minutes). Light passing through and being emitted from the gel was captured by the photodetector.

Figure 7:
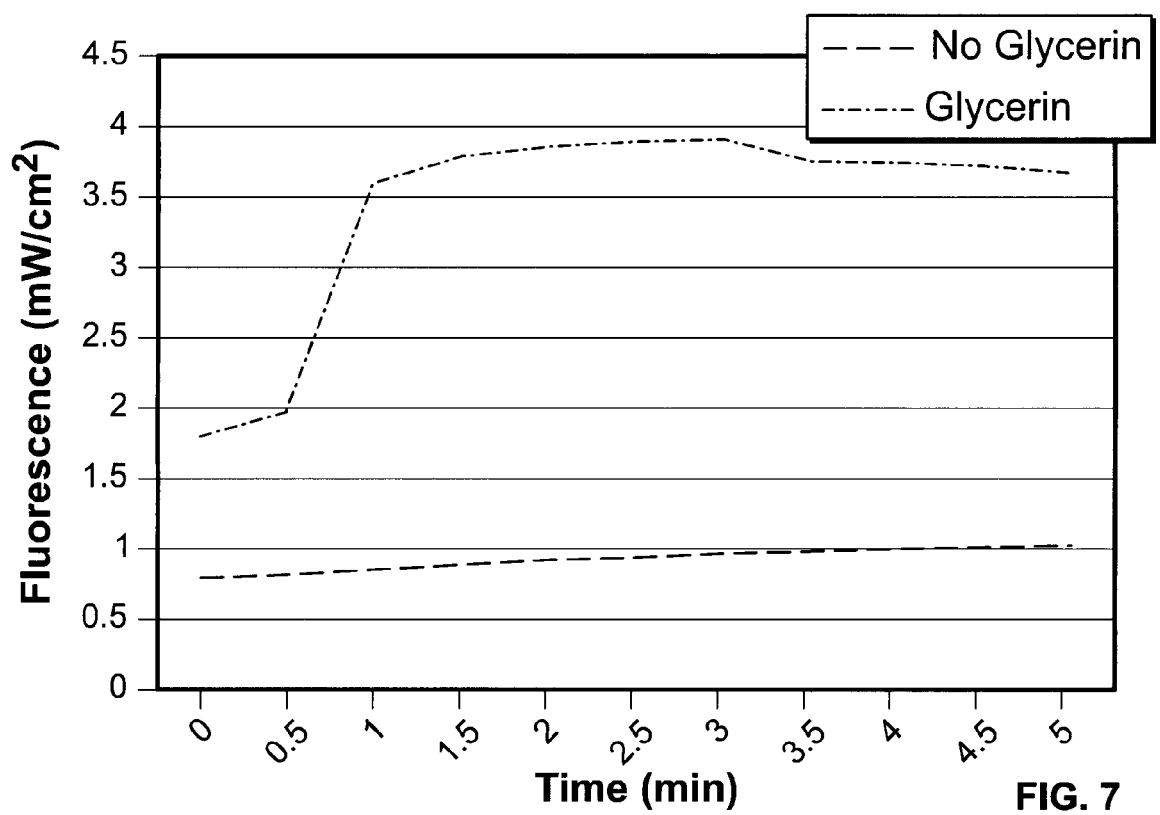
FIG. 7 depicts a comparison of the fluorescence of gel C (no glycerin) with the fluorescence of gel D (with glycerin) in the presence of 1% sodium bicarbonate (Example 7).

The results from this initial test are presented in FIG. 7; while the gel C sample had an adequate level of fluorescence yield, being in the range of about 0.75 to 1 mW/cm$^2$ over the course of the illumination period (which is a yield level that is comparable to or greater than that of gel A), the gel D1 sample had a comparably significantly greater fluorescence yield from the outset of the illumination period. Also, after about 30 seconds of being illuminated, the fluorescence yield of the gel D1 sample rose steeply over the course of the following 30 seconds and plateaued at level that was about 2× greater than its yield level at the commencement of the illumination period (and about 4× greater than that of the gel C sample). As a result from this preliminary round of in-solution testing, it was determined that glycerin (glycerol) could be a candidate compound for addition to a gel along with a bicarbonate so as to provide for a gel that would have an adequate or even enhanced level of fluorescence.

Example 8

Initial Scaling of Bicarbonate

As addition of glycerin (in order to produce a gel D1) had a positive impact on the amount of fluorescence that a gel composition could yield, a subsequent test, was performed utilizing a % range of sodium bicarbonate added to a D1 gel to test whether increasing the sodium bicarbonate would affect fluorescence of the D1 gel. To prepare the D1 gel samples, all of the ingredients (along with 3× of the chromophore Eosin Y) were combined and mixed together. Thereafter, the given amount of sodium bicarbonate (SB) powder (based on a % weight for a 100 gram amount of gel) was added to the mixed gel. The SB levels that were tested from 0.1% to 10%.

Figure 8:
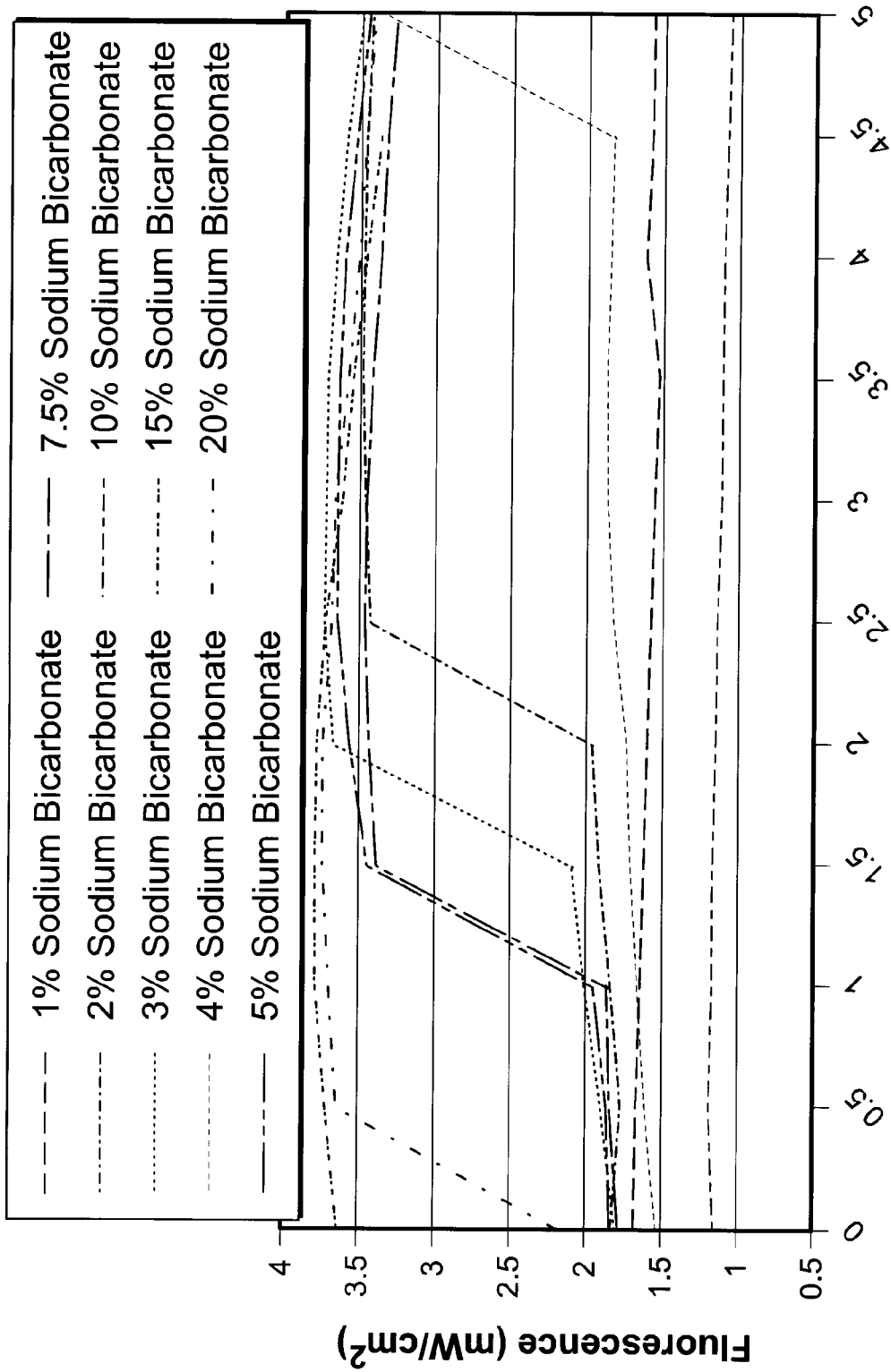
FIG. 8 depicts the effect of the presence of varying concentrations of sodium bicarbonate on the fluorescence of gel D1 (Example 8).

Referring to FIG. 8, the results indicated that addition of sodium bicarbonate could, depending on the percent amount added and after having a post-addition incubation period run its course, could have a positive influence on the fluorescence yield of D1 gel. With the addition of the sodium bicarbonate, upon the gel being illuminated with the multi-LED blue light, the tested D1 gels changed their physical texture, becoming less gel-like and noticeably more swollen.

Example 9

Scaling of Glycerol

In a further series of experiments, samples of the D1 gel having various amounts of glycerin were tested for their fluorescence yield capacity and, also, to evaluate the contribution that the added glycerin may make to changing the texture of the gel during the illumination period given that the inclusion of glycerin in the gel was observed as being required in order to have the gel swell and become less viscous (which would facilitate its removal from a patient after completion of a round of treatment). Prior observations made in Example 7 indicated that in an absence of glycerin, the gel did not undergo a textural change upon the gel being illuminated. As such, D1 gel samples were prepared having either a lowered glycerin content (218 mg/g), a medium glycerin content (436 mg/g) or a high glycerin content (654 mg/g), and subsequently tested for their fluorescence capacity.

To test the samples for their fluorescence yield, an 0.63 mL aliquot of the given gel sample is placed in a circular well device that has a 2 mm depth inscribed thereupon (the gel is loaded into the well in order to completely fill (with no air pockets remaining) the well up to the 2 mm depth line, a cover slip/slide is placed on top the ensure that the 2 mm depth of gel is maintained) and the device is placed upon a glass slide mounted above a SP-100 photodetector (CSA Group/ORB Optronix (Washington state, USA, Kirkland, 98033)); once readied, the gel is illuminated using the KLOX multi-LED blue light (THERA™) for a pre-set time (typically either 5 or 10 minutes, in the present Example 8, this time being a 5 minute illumination period for the high and medium glycerin content D1 gel samples, and 10 minutes for the lower glycerin content D1 gel sample), while the light passing through and being emitted from the gel is captured by the photodetector.

Figure 9A:
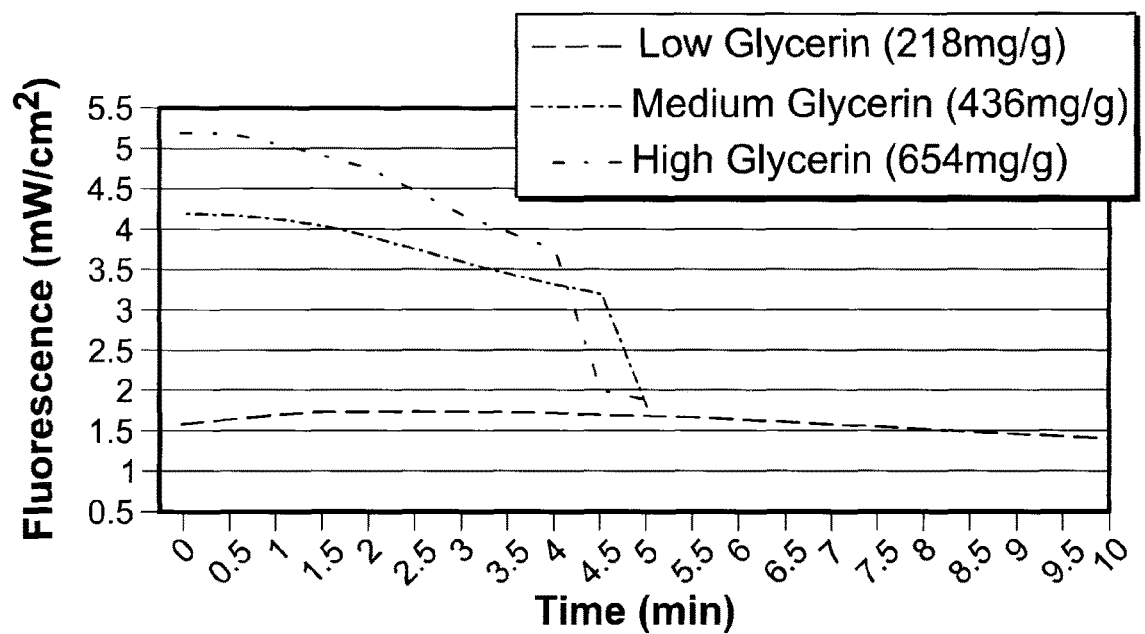
FIGS. 9A, 9B and 9C depict the effects of low glycerin (218 mg/g), medium glycerin 436 mg/g), and high glycerin (654 mg/g) on the fluorescence colors output of gel D1 (Example 9).
Figure 9B:
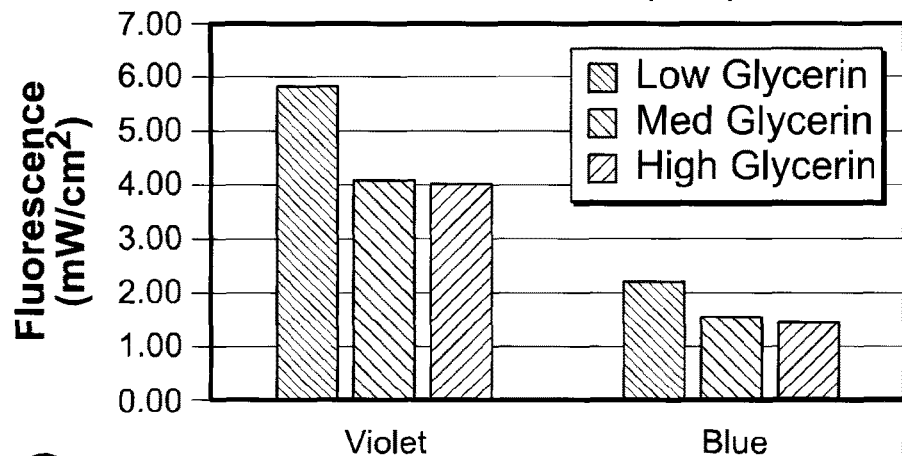
Figure 9C:
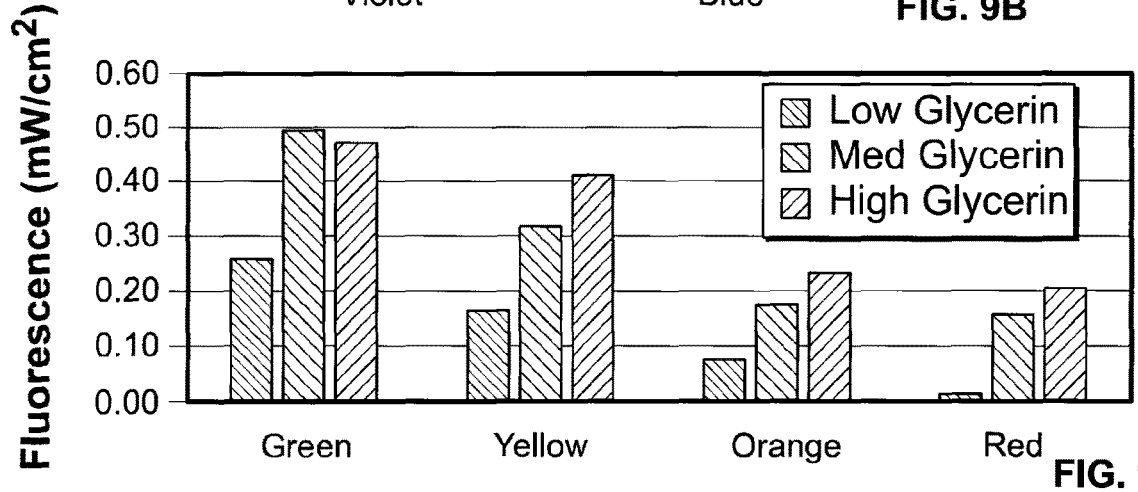

The results of the fluorescence testing are presented in FIGS. 9A-9C and Table 15 below. Visual observations were also made of the D1 gel samples during the preparation process and while being illuminated; the high glycerin content D1 gel mixture was very sticky, and the low glycerin content D1 gel mixture was only slightly sticky, and while being illuminated (along with having sodium bicarbonate is added to the mixtures) there was a much greater degree of swelling and reduction of the viscous nature of the high glycerin content D1 gel. As shown in FIG. 9A, the fluorescence yield from both the high and medium glycerin content gels was significantly elevated over that of the lower glycerin amount D1 gel test sample (which itself was higher than that of a gel A). With respect to the fluorescence color spectrum emitted from the illuminated gels, as can be seen from the results shown in FIG. 9B and FIG. 9C, both the high and medium glycerin content gels emitted elevated levels of green and yellow fluorescence, along with greater amounts of orange and red.

TABLE 15

Gel D1 fluorescence colors output - scalling of glycerol

| Color | Low Glycerin | Med Glycerin | High Glycerin |
| --- | --- | --- | --- |
| Violet | 5.82 | 4.08 | 4.02 |
| Blue | 2.21 | 1.56 | 1.45 |
| Green | 0.26 | 0.49 | 0.47 |
| Yellow | 0.16 | 0.32 | 0.41 |

TABLE 15-continued

Gel D1 fluorescence colors output - scalling of glycerol

| Color | Low Glycerin | Med Glycerin | High Glycerin |
| --- | --- | --- | --- |
| Orange | 0.07 | 0.17 | 0.23 |
| Red | 0.01 | 0.16 | 0.20 |

As a result of the Example 9 experiments, for utilization of the D1 gel in further testing, samples having the medium amount of glycerin added to them (436 mg/g) were utilised, given the high level of fluorescence output and the ability of such a gel to have a change in its physical texture occur during the illumination period.

Example 10

Scaling of Chromophore with Bicarbonate Added

As addition of sodium bicarbonate (to form a gel C composition) and glycerin (to form a D1 gel composition) gave positive results, further series of experiments were conducted in order to evaluate a range of chromophore (in present disclosure, this being Eosin Y) concentrations that would result in a gel composition with adequate fluorescence. For these Example 10 experiments, samples of the D1 gel with 5% sodium bicarbonate was used, with the amounts of chromophore added as 109, 327, 545, and 763 µg/g of Eosin Y (labelled as 1x, 3x, 5x, and 7x respectively). Sample placement, lamp distance and illumination times were as per those described in Example 9 of the present disclosure.

Figure 10A:
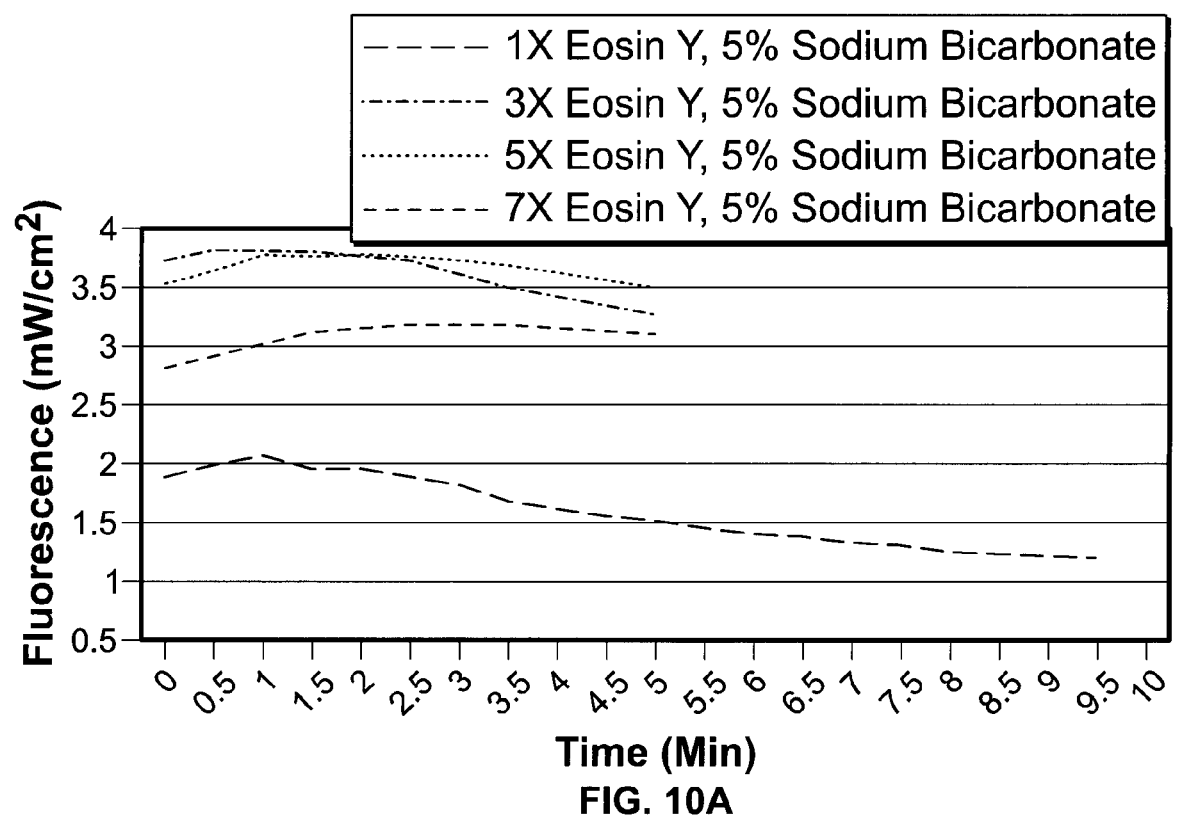
FIGS. 10A, 10B and 10C depict the effect of increased amounts of eosin Y (109, 327, 545, and 763 µg/g of Eosin Y (labelled as 1×, 3×, 5×, and 7× respectively)) on the fluorescence colors output of gel D1 (Example 10).
Figure 10B:
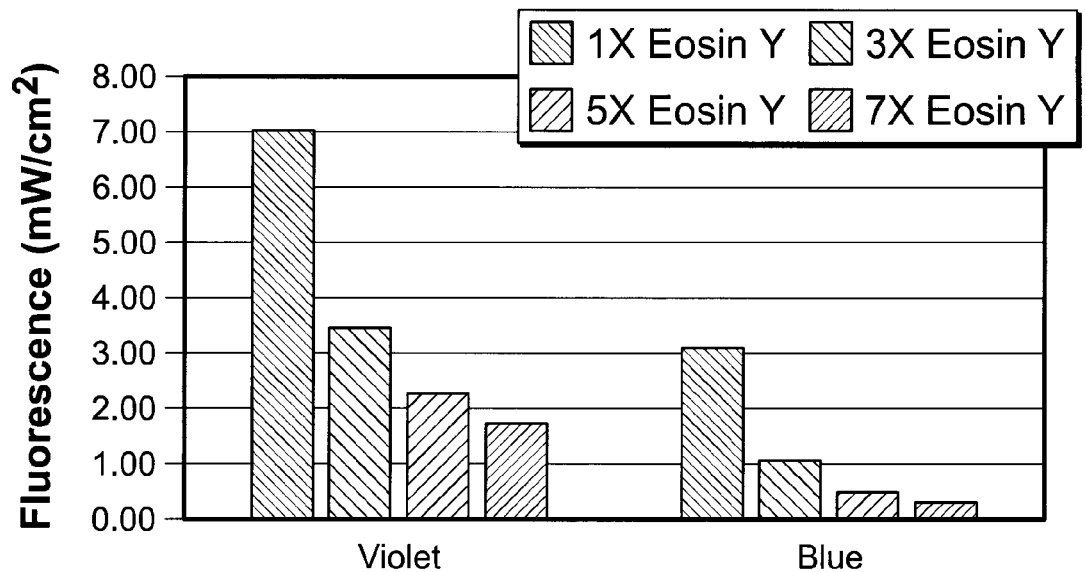
Figure 10C:
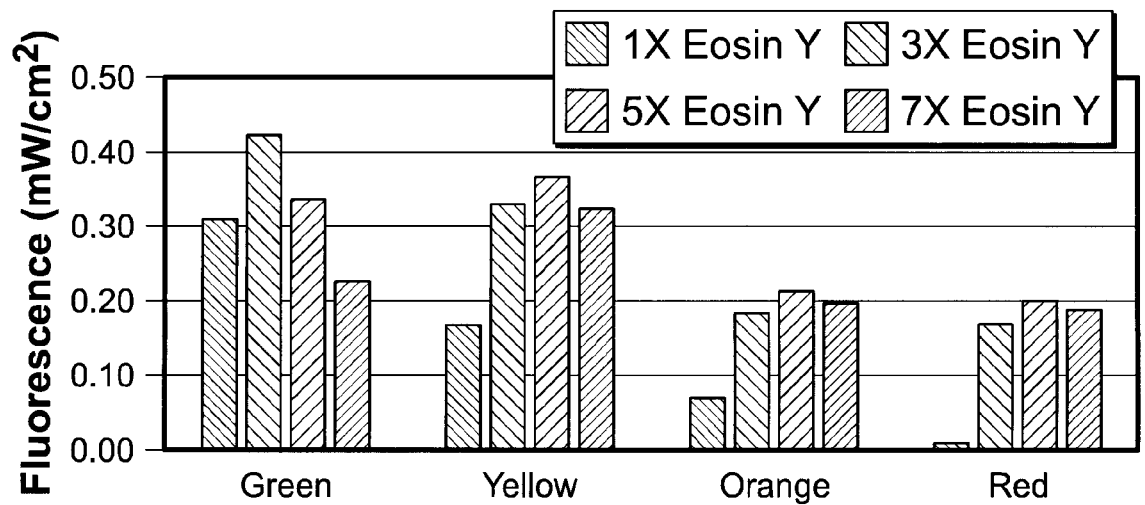

Results from the experiment are presented in FIGS. 10A-10C and Table 16 below. As can be seen from FIG. 10A, the D1 gel samples that had the elevated amount of the chromophore beyond 1x yielded an elevated level of fluorescence, with the 3x and 5x chromophore D1 gels having the greatest fluorescence but with the 7x chromophore D1 gel having less (compared to the 3x and 5x chromophore D1 gels) overall fluorescence and significantly less blue and green emitted wavelengths, suggesting that a level above 5x chromophore, the D1 gel did not function as well.

TABLE 16

Gel D1 fluorescene colors output-scaling of chromophore

| Color | 1X Eosin Y | 3X Eosin Y | 5X Eosin Y | 7X Eosin |
| --- | --- | --- | --- | --- |
| Violet | 7.06 | 3.48 | 2.29 | 1.75 |
| Blue | 3.11 | 1.08 | 0.51 | 0.32 |
| Green | 0.31 | 0.42 | 0.34 | 0.23 |
| Yellow | 0.17 | 0.33 | 0.37 | 0.32 |
| Orange | 0.07 | 0.18 | 0.21 | 0.20 |
| Red | 0.01 | 0.17 | 0.20 | 0.19 |

The results from the Example 10 experiments indicated that elevating the chromophore (Eosin Y) content, but not over-elevating it, would produce a D1 gel with an enhanced fluorescence profile, and thus, for further experiments levels of either 3x or 5x Eosin Y contents for D1 gel testing were to be used in further rounds of testing.

Example 11

Bicarbonate Alternative Salts

As the addition of bicarbonate, in the form of sodium bicarbonate, to form gel C, and additionally as an additive to the D1 gel, could positively influence the fluorescence output from a gel composition, other salts of a similar nature to sodium bicarbonate were evaluated, by adding them in powder form to a given gel composition. In a first round of experiments, tests were performed with potassium bicarbonate, calcium carbonate, sodium acetate and sodium biphosphate to test their on the fluorescence output from a D1 gel having a 3× level of chromophore Eosin Y. Test samples comprising the various salts were evaluated in comparison to the D1 gel (with 3× Eosin Y) containing 1% sodium bicarbonate and to the D1 gel (with 3× Eosin Y) lacking any added salt. Gels were prepared as per the procedure described in Example 9, with the illumination time being 10 minutes. Results from the first round of testing the alternative salts are presented in FIGS. 11A and 11B, and in Table 17 below.

Figure 11A:
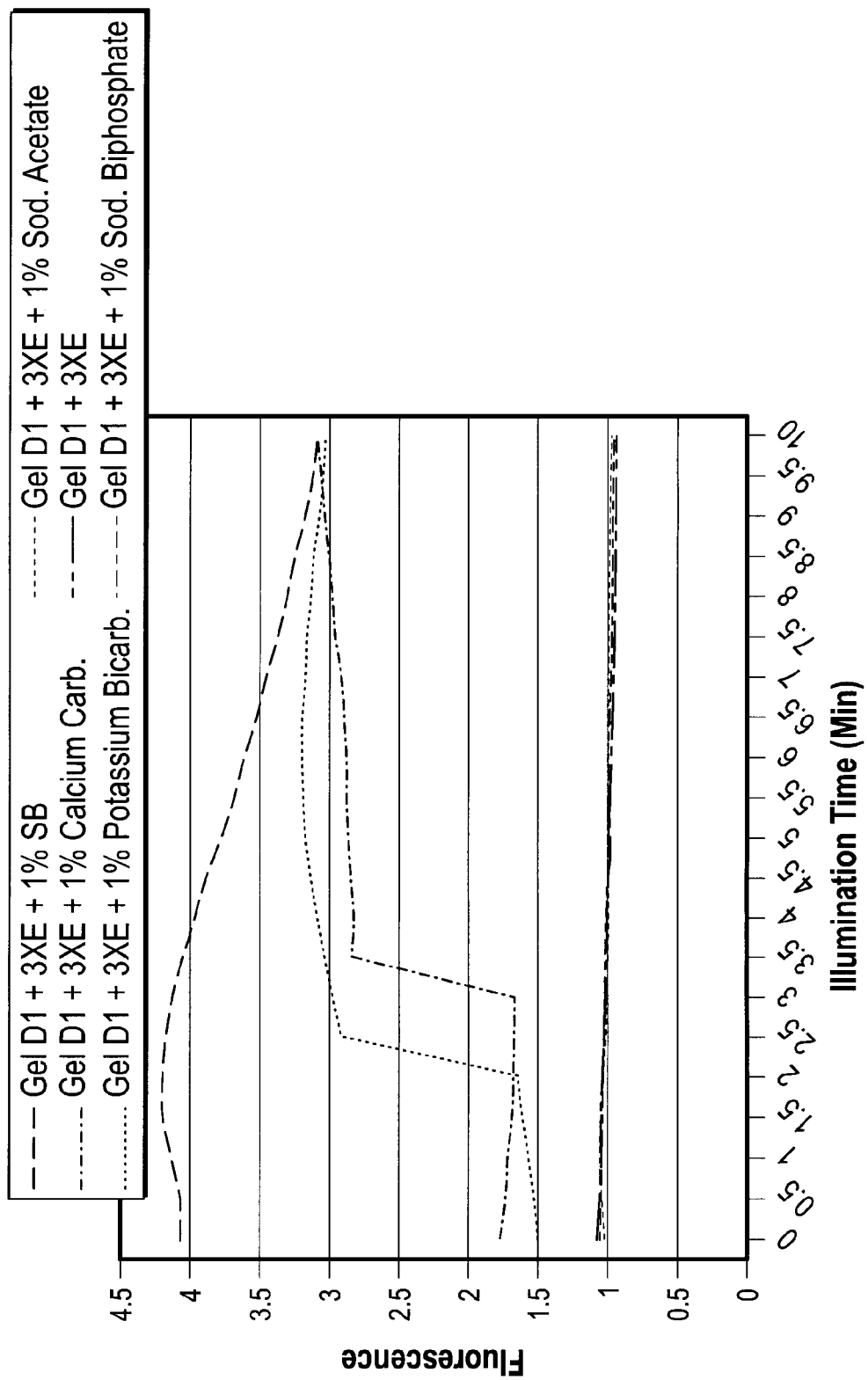
FIGS. 11A, 11B and 11C depict the impact of various salts, such as sodium bicarbonate (SB), calcium carbonate (Calcium Carb), potassium bicarbonate (Potassium Bicarb), sodium acetate (Sod. Acetate), sodium biphosphate (Sod. Biphosphate) on the fluorescence of gel D1 with 327 µg/g (3XE) Eosin Y (Example 11).
Figure 11B:
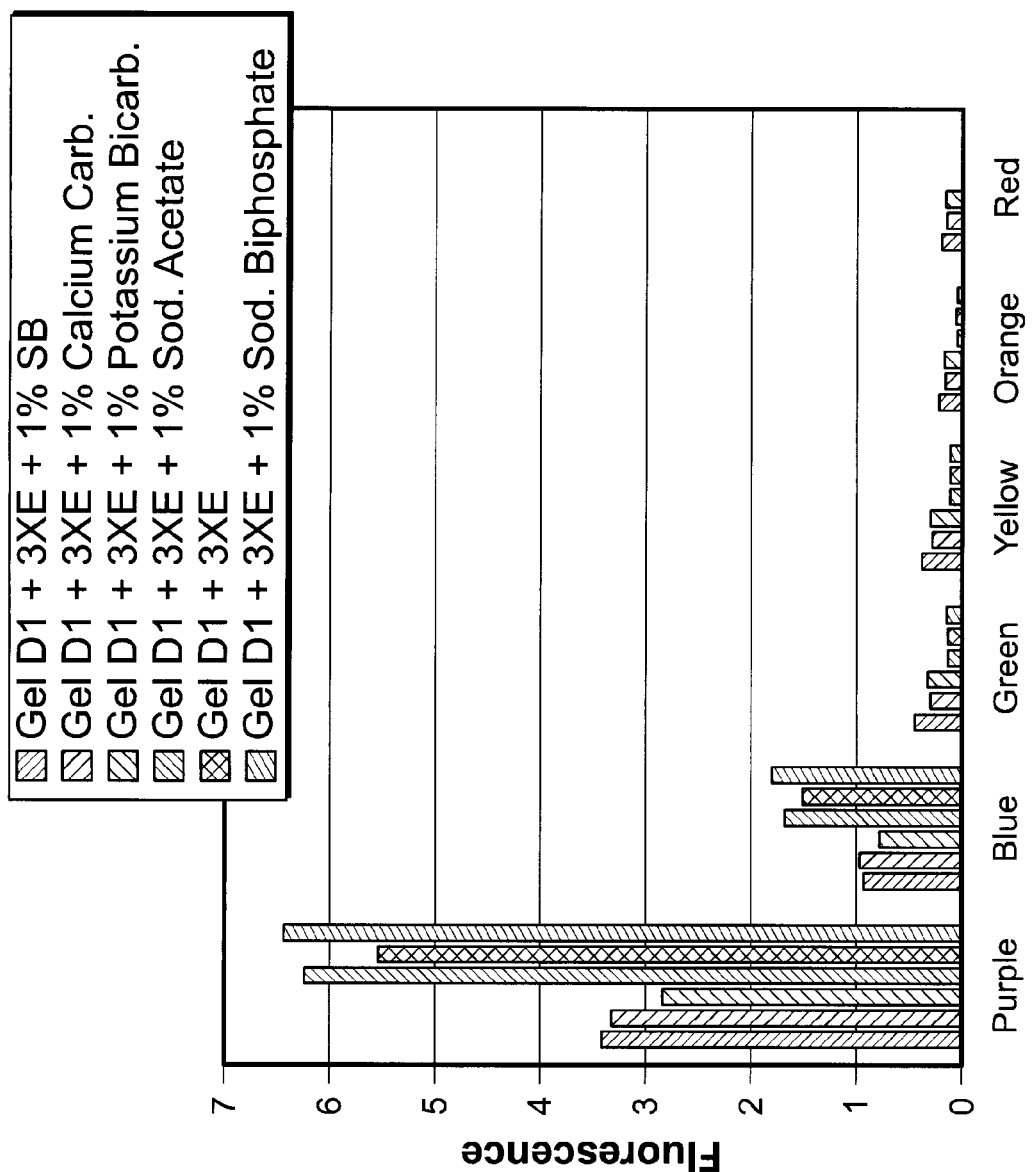

As can be seen from FIG. 11A, while the sodium acetate and sodium biphosphate salts did not appear to cause any enhancement of the D1 gel fluorescence given that these gel samples yielded the same fluorescence profile as the D1 gel itself, addition of the potassium bicarbonate and calcium carbonate salts, respectively, to the D1 gel resulted in an enhanced fluorescence level after several minutes of the gels being illuminated, and the fluorescence level output from the D1 gels bearing either of these two salts was similar to the sodium bicarbonate salt by the end of the illumination period. The D1 gel bearing each of these salts potassium bicarbonate give a close result to we had with the sodium bicarbonate, but it seems that the reaction occur is slower with those two new powders. With respect to the fluorescence color profile, referring to FIG. 11B and Table 17, the D1 gel containing the 1% potassium bicarbonate was most similar (albeit with lower output levels) to the D1 gel bearing the sodium bicarbonate both from a color emission profile and a textural perspective. Similarly, the D1 gel having the 1% calcium carbonate added had color emission profile similar to the two bicarbonate salt D1 gels (elevated output of green, yellow, orange and red light), however, its texture remained unchanged over the course of the illumination period.

ate (1%); calcium carbonate (1% and 5%); and magnesium carbonate (1% and 5%). Each gel with its respective added salt powder was then mixed for 1 minute, and then measured for its fluorescent properties in accordance with the procedure described in Example 9. The results from this round of testing are presented in FIG. 11C.

Figure 11C:
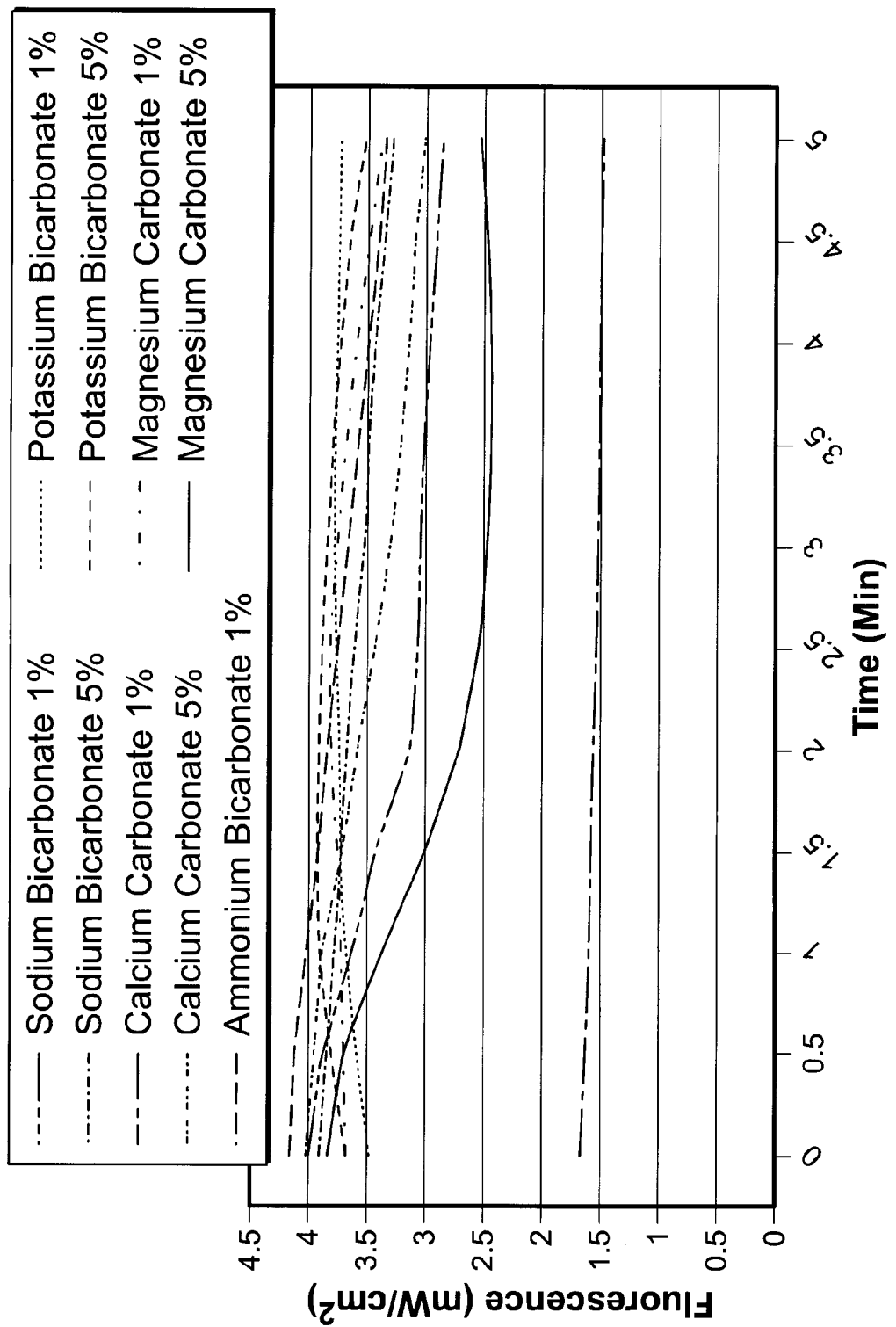

As can be seen from FIG. 11C, all of the bicarbonate and carbonate salts that were tested resulted in a D1 gel compositions that yielded elevated levels of fluorescence, and although the D1 gel comprising the 1% calcium carbonate salt had the lowest fluorescence level of the group, its level of fluorescence was still well beyond that of a gel A composition. As such, it would be possible to use any of these tested bicarbonate or carbonate salts in a gel composition for enhancing a level of fluorescence output from the given gel.

Example 12

Superoxide Dismutase (SOD) with/without Bicarbonate
SOD—Fluorescence

In a first set of experiments to test the effect of adding super oxide dismutase (SOD) to the gel composition, an experiment was conducted to determine whether an addition of SOD to a D1 gel composition could have an impact on a fluorescence output of the D1 gel. As such, 0.1%, 0.2%, 0.5%, and 1% SOD were added to a 1 gram mixture of a D1 gel, followed by an addition of 327 µg/g of the chromophore Eosin Y, and the resulting mixture was analyzed spectrophotometrically for fluorescence in accordance with the procedure described in Example 9.

Figure 12A:
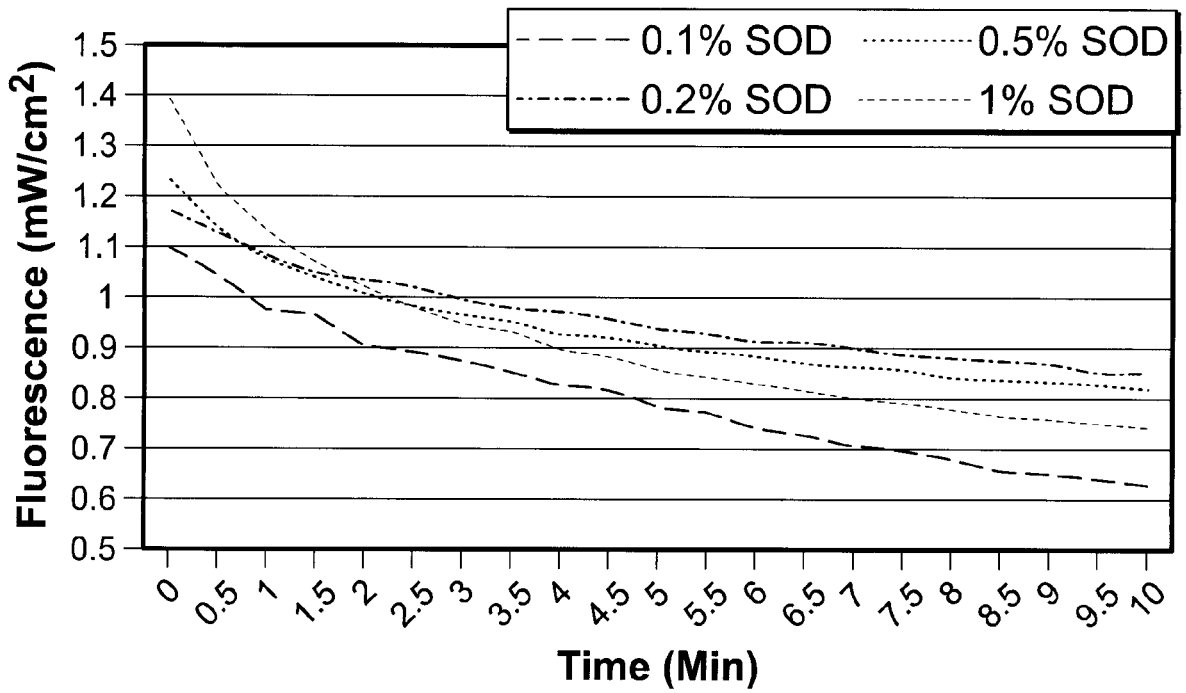
FIGS. 12A, 12B, 12C, 12D and 12E depict the impact of varying concentrations of superoxide dismutase (SOD) on the fluorescence and ROS production of gel D1 in the absence of sodium bicarbonate (FIGS. 12A, 12B, and 12C) and in the presence of sodium bicarbonate (FIGS. 12D and 12E) (Example 12).
Figure 12B:
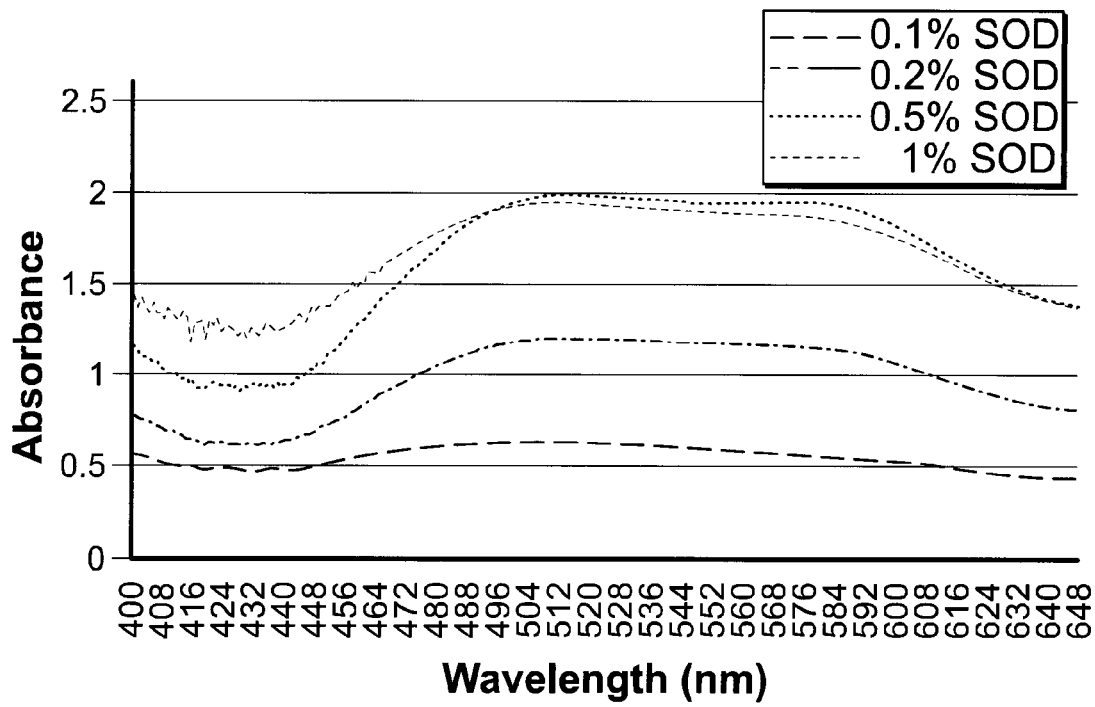

Referring to FIG. 12A and FIG. 12B, the results indicated that with these percentages of added SOD, there was only a

TABLE 17

Gel D1 Fluoresence output and structure with various salts added

| D1 Gel type | Gel acidity (pH) | Gel structure (Bubble) | Fluorescence color output | | | | | |
|---|---|---|---|---|---|---|---|---|
| | | | Purple | Blue | Green | Yellow | Orange | Red |
| Gel D1 | 4.8 | N/A | N/A | N/A | N/A | N/A | N/A | N/A |
| Gel D1 + 3XE | 4.8 | Low | 5.54 | 1.51 | 0.13 | 0.11 | 0.06 | 0.01 |
| Gel D1 + 3XE + 1% NaBicarb | 5.65 | High | 3.41 | 0.93 | 0.44 | 0.38 | 0.22 | 0.2 |
| Gel D1 + 3XE + 1% CalCarb | 4.86 | N/A | 3.32 | 0.97 | 0.3 | 0.28 | 0.16 | 0.15 |
| Gel D1 + 3XE + 1% PotBicarb. | 5.8 | High | 2.84 | 0.78 | 0.32 | 0.3 | 0.17 | 0.16 |
| Gel D1 + 3XE + 1% SodAcetate | 5.02 | Low | 6.24 | 1.68 | 0.13 | 0.11 | 0.05 | 0.01 |
| Gel D1 + 3XE + 1% NaBiphosphate | 5.5 | N/A | 6.43 | 1.8 | 0.14 | 0.11 | 0.05 | 0.01 |

A further round of experiments was conducted to determine what, if any, difference would occur when different sources of bicarbonate (or carbonate) were used in conjunction with the D1 gel.

To perform this experiment, a D1 gel composition with 327 µg/g of Eosin Y was prepared. Thereafter, an amount (in powder form) of each respective bicarbonate (or carbonate) salt was added to the given D1 gel sample. The bicarbonate and carbonate salts that were tested, denoted in the final weight percentage that was added to the given D1 gel composition, included: sodium bicarbonate (1% and 5%); potassium bicarbonate (1% and 5%), ammonium bicarbonminor effect on a fluorescence output from the given D1 gels. While the D1 gels that contained the relatively higher amounts of SOD had relatively higher levels of fluorescence output to those D1 gels with lower amounts of SOD, no direct correlation was observed as between the presence of SOD in the gel and the gel's fluorescence output. In addition, without sodium bicarbonate the gel will not "transform", and thus its fluorescence is reduced.

SOD—ROS Production

This experiment was conducted to determine how SOD at various concentrations affects the fluorescence output from a D1 gel. An evaluation was also performed as to whether the addition of SOD to a D1 gel composition may affect the D1 gel vis-à-vis its ROS production capacity. To measure for such an effect, the total hydrogen peroxide content in a D1 gel comprising an addition of SOD ranging from concentration of 0.1%, 0.2%, 0.5% to 1% SOD were tested to establish an amount of SOD that could be added to a D1 gel to maximize hydrogen peroxide content.

To perform the experiment, 0.1 grams of D1 gel were mixed with various SOD concentrations, with 1 mL of working reagent. The solution was mixed, and allowed to sit at room temperature for 30 minutes, after which time, the absorbance was measured for each solution at 560 nm using the Pierce assay described in Example 6.

One result, not from the spectrophotometer, to be assayed for by visual inspection was the color of the solutions. A high concentration of hydrogen peroxide should turn the yellow solution to a purple solution. All 4 solutions tested turned the solution to a brown.

Figure 12C:
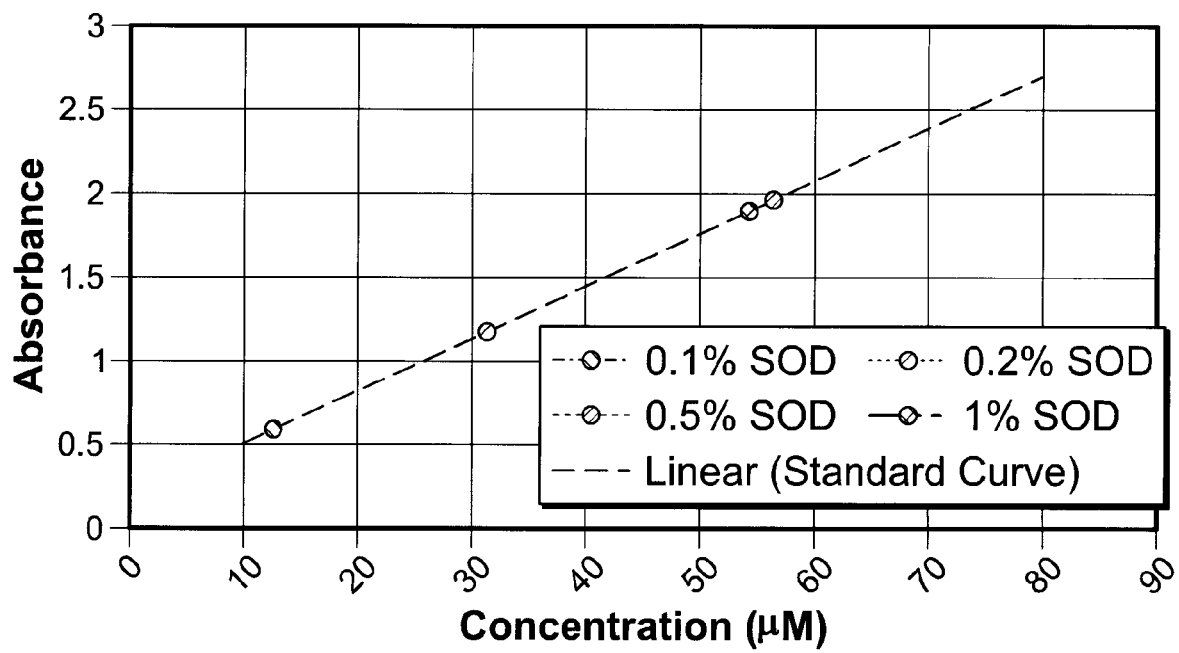

At the completion of the 30 minute incubation period, all four D1 gel test solutions were analyzed, first of all, visually, and all 4 solutions were observed to have turned the test solution brown, indicating a level of hydrogen peroxide production in each of test solutions. With reference to FIG. 12C, the spectrophotometric measurements indicated that with increasing the amount of SOD added to the D1 gel composition, an increase in the hydrogen peroxide content was observed.

From the above-noted data, it was concluded that increasing SOD content could result in an increase hydrogen peroxide content in the D1 gel, with very little difference between adding SOD to a final amount 0.5% versus 1% per weight of gel, with the 0.5% SOD being the more effective amount.

SOD—with Glycerine and Bicarbonate—Fluorescence Effect

As the prior experiments described above indicated the addition of SOD to a D1 gel could stimulate ROS production in the D1 with the addition of 0.5% SOD (per weight of gel), tests were thus performed to assess whether a combined addition of SOD and sodium bicarbonate might result in a D1 gel with an elevated fluorescence profile of a D1 gel.

Figure 12D:
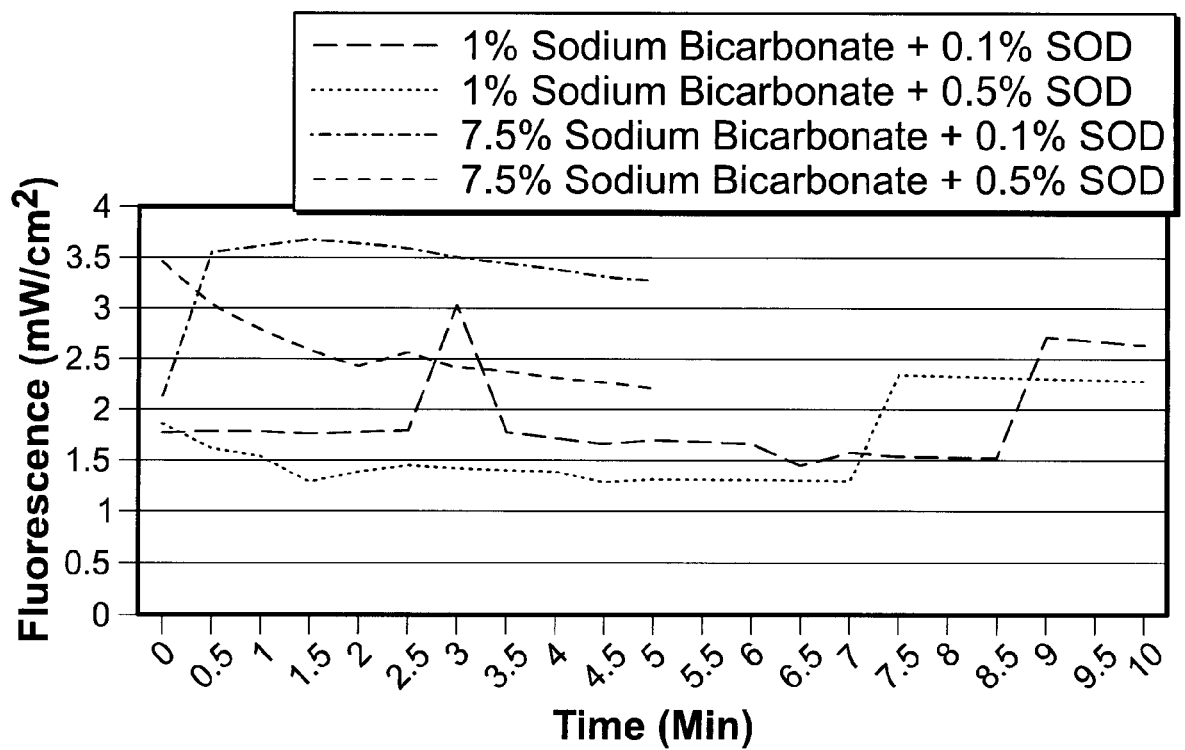

D1 gel samples were prepared with 0.1% SOD and 0.5% SOD (as these SOD concentrations were the lowest and highest concentrations that had previous effects on the gel) to which 1% sodium bicarbonate and 7.5% sodium bicarbonate were added (likewise, these % concentrations were chosen for the same reasons). As such, using these ingredients, the following four D1 gels were made:
  0.1% SOD with 1% sodium bicarbonate
  0.5% SOD with 1% sodium bicarbonate
  0.1% SOD with 7.5% sodium bicarbonate
  0.5% SOD with 7.5% sodium bicarbonate The gels were measured for their fluorescence output in accordance with the procedure described in Example 9, and the results of this experiment are presented in FIG. 12D. Looking at the results presented in FIG. 12D, an addition of SOD may have had an effect on fluorescence when added at the lower concentration amounts in combination with an addition of sodium bicarbonate.

With respect to an addition of glycerin having an effect on the amount of ROS being produced in a D1 gel composition that also had SOD and sodium bicarbonate added, the protocol described above regarding the preparation of the gel compositions was utilized, and the amount of ROS generated from each of the gels was assayed using the Pierce assay methodology.

Figure 12E:
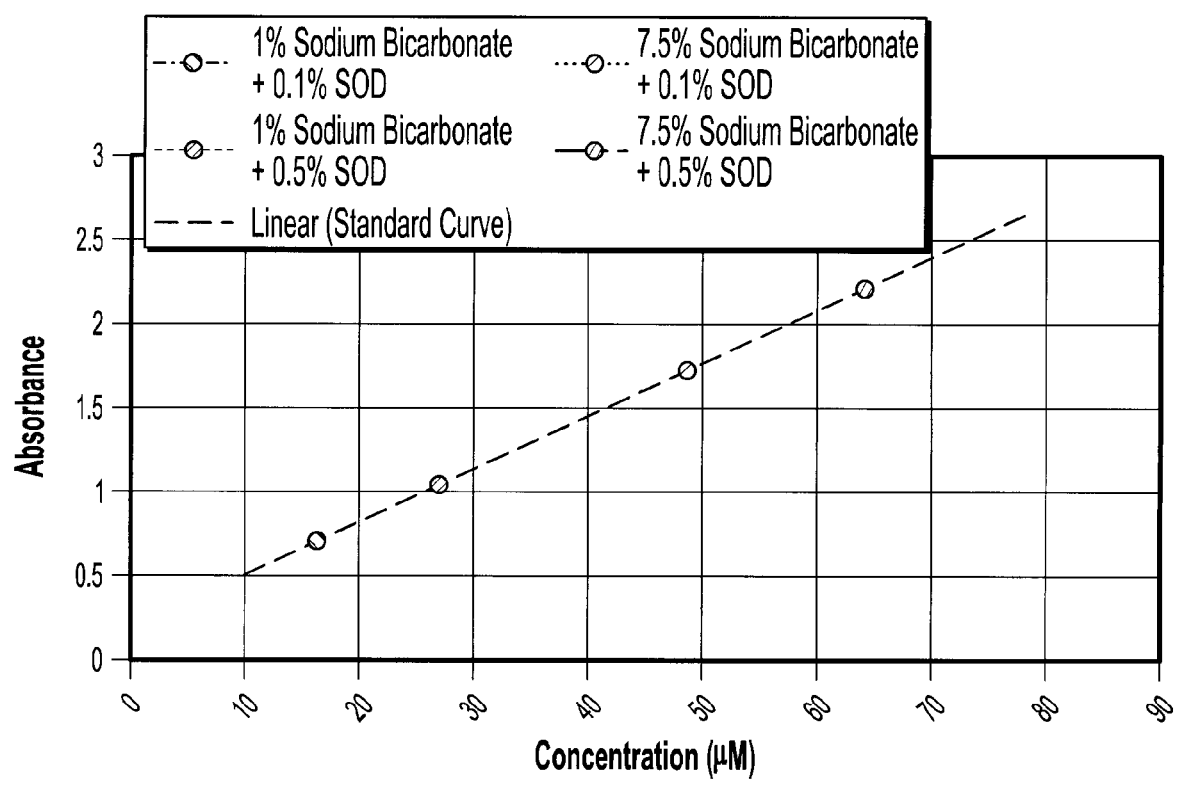

The results of ROS measurement experiment are shown in FIG. 12E. Firstly, the results indicated that the presence of the sodium bicarbonate has a larger impact than SOD alone on generation of ROS production (at the concentrations used). Secondly, the results also indicated that the two ingredients could be used in combination to increase ROS production even further than either ingredient alone.

Example 13

Optimizing the Bicarbonate Concentration

A further experiment was conducted in order to investigate a more refined percentage gradient of bicarbonate (in the form of sodium bicarbonate) that could be added to a D1 gel composition in order to generate a maximal amount of fluorescence while concomitantly maintaining at least a neutral pH and a ROS output of between 1.5-2.0 μM (based on prior experimental results—see Part A of the Examples). As such D1 gel compositions were prepared, to which were added various amounts of sodium bicarbonate powder in order to provide D1 gel samples with the following % sodium bicarbonate: 0.1%, 0.4%, 0.5%, 0.75%, 1%, 2%, 3%, 4%, and 5%. Gel samples were tested for their overall fluorescence output and with respect to their fluorescence output for colors in the visible range; the set-up, illumination and analysis was that as described in Example 9. The results from the experiment are presented in FIG. 13A regarding the overall fluorescence output and FIG. 13B and Table 18 with respect to the fluorescence of the individual colors in the visible range.

Figure 13A:
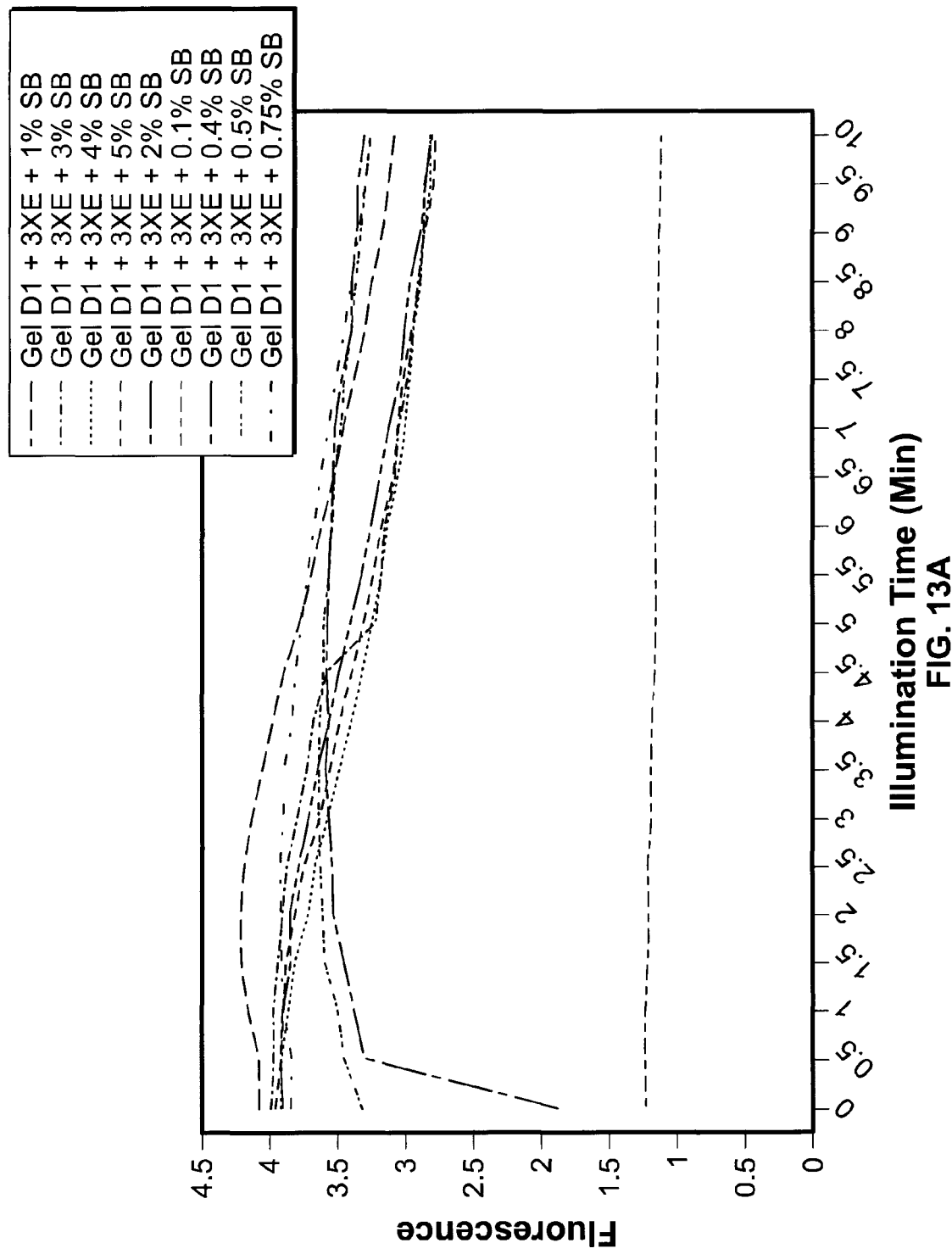
FIGS. 13A and 13B depict the impact of varying concentrations of sodium bicarbonate (SB) on the fluorescence of gel D1 with 327 µg/g (3XE) Eosin Y (Example 13).
Figure 13B:
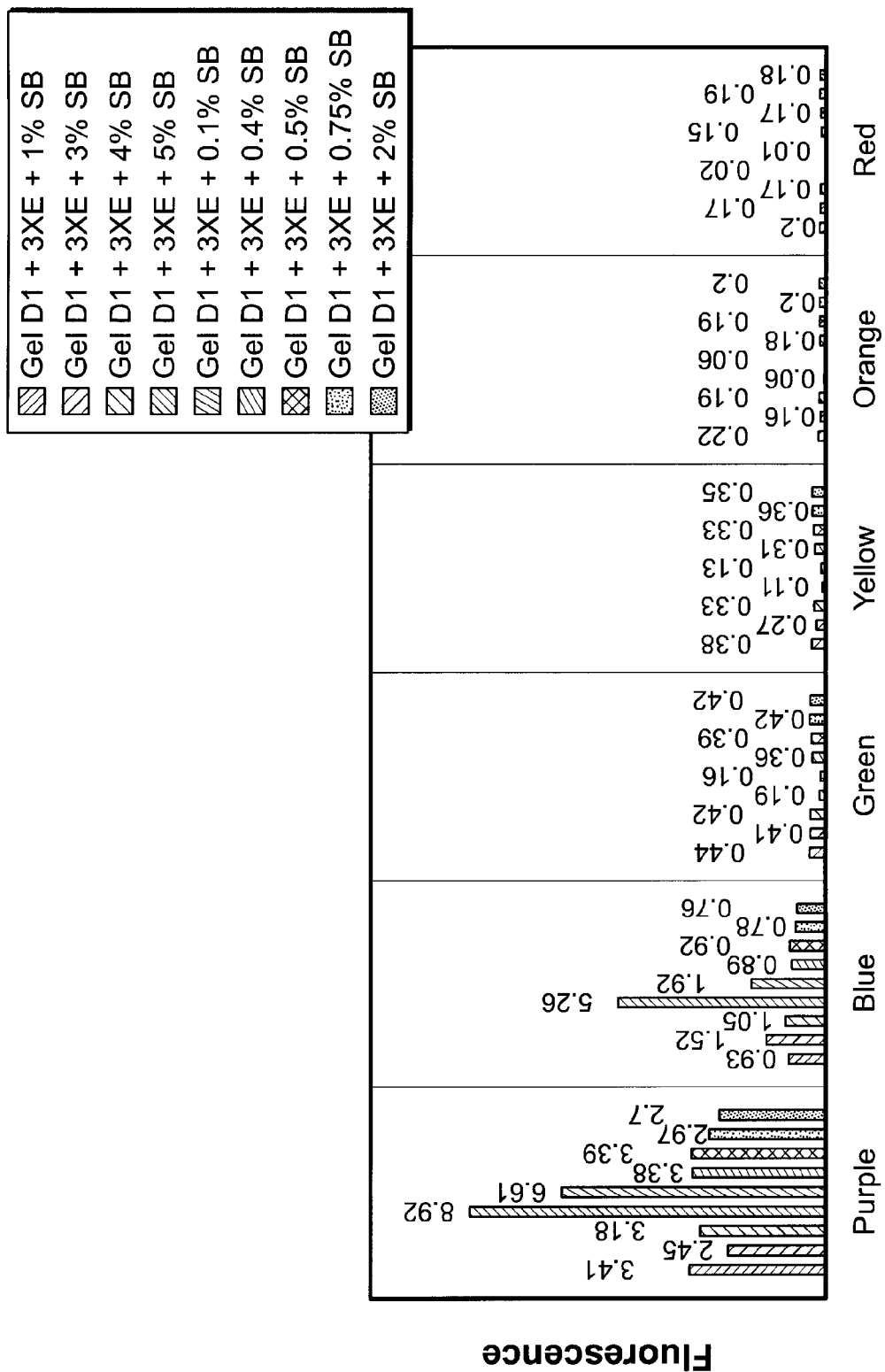

Looking at FIG. 13A, it can be observed that with the exception of the lowest and highest salt % concentrations, all of the % sodium bicarbonate concentrations incorporated into a D1 gel resulted in a gel having elevated fluorescence output. For the 2% sodium bicarbonate test gel, this gel appeared to have a minor lag time before its fluorescence level increased, however, its overall level ultimately was like the other % concentrations tested (with the exception of the 0.1% and the 5% test sample gels). Regarding the individual fluorescence color profiles for each of the sample D1 gels tested, looking at FIG. 13B and Table 18, it is clear that, with the exception of the 0.1% and 5% sodium bicarbonate sample D1 gels, the test gels with the added bicarbonate salt % yielded fluorescence evenly across the entire range of visible colors.

TABLE 18

| | Gel D1 fluorescence - scaling of bicarbonate (SB) | | | | | | | |
|---|---|---|---|---|---|---|---|---|
| D1 Gel type | Acidity (pH) | Gel structure (Bubble) | Fluorescence color output | | | | | |
| | | | Purple | Blue | Green | Yellow | Orange | Red |
| 3XE + 0.1% SB | 5.38 | Low | 6.61 | 1.92 | 0.16 | 0.13 | 0.06 | 0.01 |
| 3XE + 0.4% SB | 5.61 | Low-Average | 3.38 | 0.89 | 0.36 | 0.31 | 0.18 | 0.15 |
| 3XE + 0.5% SB | 5.7 | Average | 3.39 | 0.92 | 0.39 | 0.33 | 0.19 | 0.17 |
| 3XE + 0.75% SB | 5.95 | High | 2.97 | 0.78 | 0.42 | 0.36 | 0.2 | 0.19 |
| 3XE + 1% SB | 6.15 | High | 3.41 | 0.93 | 0.44 | 0.38 | 0.22 | 0.2 |
| 3XE + 2% SB | 6.38 | High | 2.7 | 0.76 | 0.42 | 0.35 | 0.2 | 0.18 |
| 3XE + 3% SB | 6.69 | High | 2.45 | 1.52 | 0.41 | 0.27 | 0.16 | 0.17 |

TABLE 18-continued

| | | Gel | | | | | | |
|---|---|---|---|---|---|---|---|---|
| | Acidity | structure | Fluorescence color output | | | | | |
| D1 Gel type | (pH) | (Bubble) | Purple | Blue | Green | Yellow | Orange | Red |
| 3XE + 4% SB | 7.3 | High | 3.18 | 1.05 | 0.42 | 0.33 | 0.19 | 0.17 |
| 3XE + 5% SB | 7.6 | High | 8.92 | 5.26 | 0.19 | 0.11 | 0.06 | 0.02 |

Gel D1 fluorescence - scaling of bicarbonate (SB)

Example 14

Propylene Glycol (Separately or in Combination with Glycerol)

Further testing was performed in order to evaluate whether an addition of propylene glycol (PG) along with the presence of glycerin in a D1 gel could alter the fluorescence output of such a gel.

Firstly, the effect of combining PG and glycerol was evaluated in solution; an aqueous solution was prepared containing 3× Eosin Y, to which only glycerin, or only PG, or both glycerin and PG were added. The water-only solution served as the control. Each solution was then measured for its fluorescence using the KLOX multi-LED blue lamp with an illumination period for 5 minutes to determine their fluorescence properties of the given solutions. The results are presented in FIG. 14 along with Table 19 and Table 20.

TABLE 19

Glycerin and propylene glycol fluoresence

| | Time (min) - Fluorescence | | | | | | | | | | | |
|---|---|---|---|---|---|---|---|---|---|---|---|---|
| Sample | 0 | 0.5 | 1 | 1.5 | 2 | 2.5 | 3 | 3.5 | 4 | 4.5 | 5 | AVG |
| Glycerin | 1.62 | 1.57 | 1.54 | 1.50 | 1.47 | 1.44 | 1.39 | 1.36 | 1.32 | 1.29 | 1.24 | 1.43 |
| Propylene Glycol | 2.19 | 2.14 | 2.12 | 2.10 | 2.08 | 2.06 | 2.05 | 2.02 | 1.99 | 1.98 | 1.96 | 2.06 |
| Both | 2.17 | 2.06 | 2.04 | 2.00 | 1.99 | 1.99 | 1.96 | 1.95 | 1.94 | 1.91 | 1.91 | 1.99 |
| Water | 0.87 | 0.84 | 0.81 | 0.81 | 0.80 | 0.80 | 0.79 | 0.78 | 0.78 | 0.78 | 0.77 | 0.80 |

TABLE 20

Glycerin and propylene glycol fluorescence - color output

| Color | Water | Glycerin | Both | PG |
|---|---|---|---|---|
| Violet | 6.80 | 7.56 | 7.88 | 9.41 |
| Blue | 2.06 | 2.65 | 2.75 | 3.59 |
| Green | 0.12 | 0.16 | 0.22 | 0.24 |
| Yellow | 0.07 | 0.16 | 0.22 | 0.23 |
| Orange | 0.04 | 0.09 | 0.13 | 0.12 |
| Red | 0.01 | 0.03 | 0.04 | 0.03 |

Figure 14:
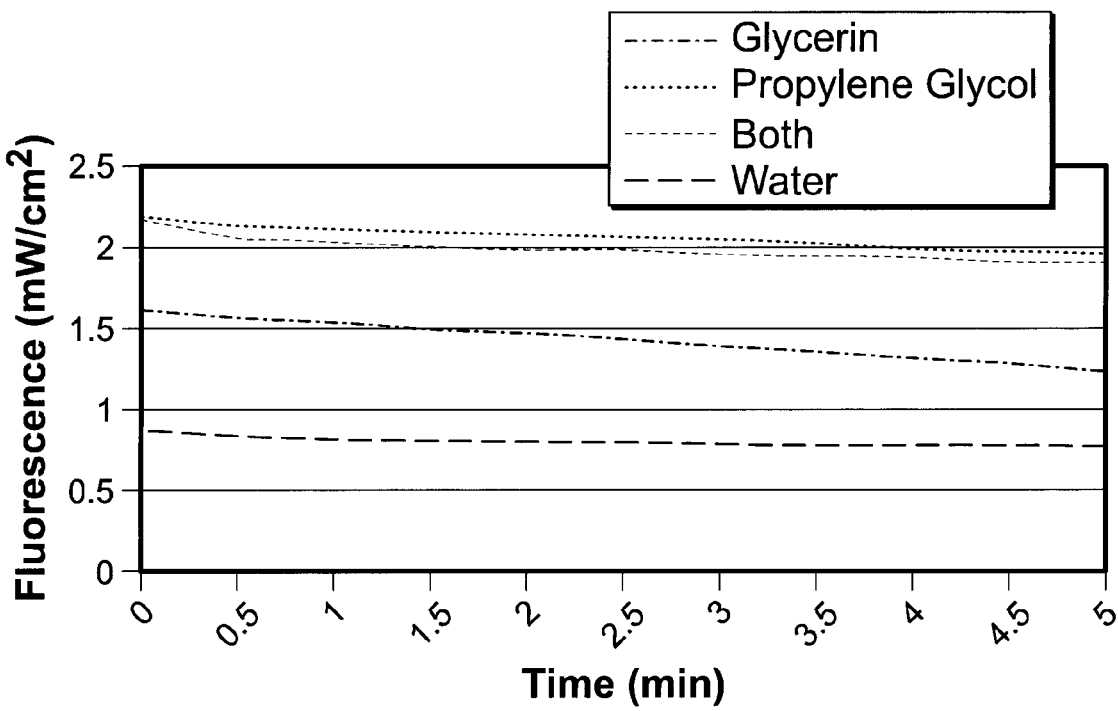
FIG. 14 depicts the impact of glycerin, propylene glycol, and the combination of glycerin and propylene glycol on the fluorescence of gel D1 (Example 14).

As can be seen from FIG. 14 and Table 19, adding both glycerin and PG had a very significant effect on the fluorescence of chromophore solutions. While the solution of 3× Eosin Y only had a fluorescence level of 0.8, with an addition of glycerin the fluorescence increased by 79% (to 1.4). When the 3× Eosin Y was placed in solution with both glycerin and PG, the fluorescence increased by 149% (to 2.0), and a similar effect was observed with adding PG itself—the fluorescence increased 158% (to 2.1). In addition to this, the blue light from the KLOX lamp also increased in this same manner, though not as significant as for fluorescence. Regarding the color spectrum of emitted fluorescence, as shown in Table 20, it was evident that the addition of glycerin resulted in an increase output of the green to red color range, and this effect was increased with the addition of the glycerin-PG combination. As such, it was concluded that the fluorescence level could be modulated by adding either a single additive such as the glycerin, or a combination such as the glycerin with PG.

Example 15

Scaling of Propylene Glycol

As an addition of PG to a glycerin-containing chromophore solution resulted in a positive impact on the fluorescence generating properties of the solution, a further evaluation was performed with respect to adding PG to a D1 gel formulation; aspects that were considered included an impact on fluorescence output from the D1 gel and whether a D1 gel with PG added to it could transmit/emit light, and also the physical characteristics of the D1 gel with the PG added; if the gel with the PG were to have an increased viscosity and tackiness (or stickiness) to it upon being illuminated with the KLOX multi-LED blue light, such would be considered as a detrimental additional quality as it would make the gel more difficult to remove.

In a first round of testing in order to establish a scale of mg/g PG that could possibly be added to a D1 gel, testing was performed on aqueous solutions with combinations of propylene glycol, glycerin and water. Ratios of these ingredients were tested to see how much of each component may be required to maximize fluorescence. Test solutions were made as follows: 1) 0 mg/g Propylene Glycol and 0 mg/g Glycerin, 2) 600 mg/g Propylene Glycol and 200 mg/g Glycerin, 3) 400 mg/g Propylene Glycol and 100 mg/g Glycerin, and 4) 400 mg/g Propylene Glycol and 400 mg/g Glycerin. To each solution, 327 µg/g Eosin Y was added. Each solution was then illuminated with the KLOX multi-LED blue light (THERA™) for a period of 5 minutes, and the fluorescence data captured as described in Example 9.

Figure 15A:
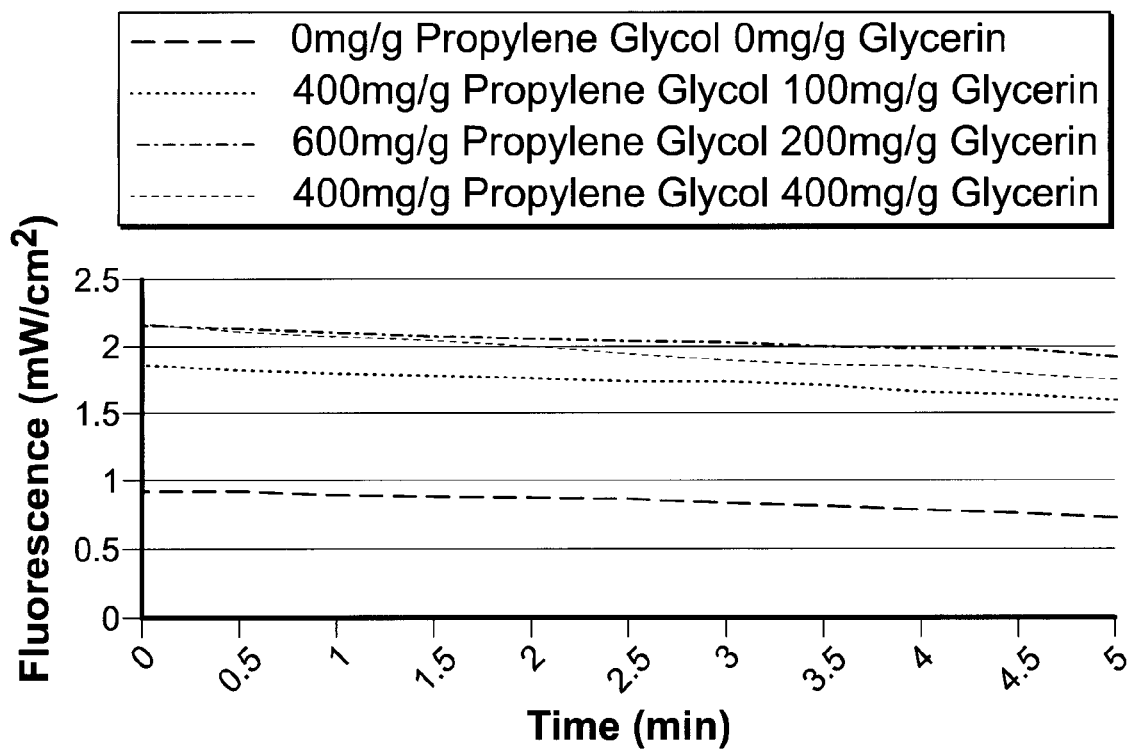
FIGS. 15A, 15B, 15C, 15D, 15E and 15F depicts the impact of glycerin, propylene glycol, and the combination of glycerin and propylene glycol on the fluorescence color output of gel D2 (Example 15).
Figure 15B:
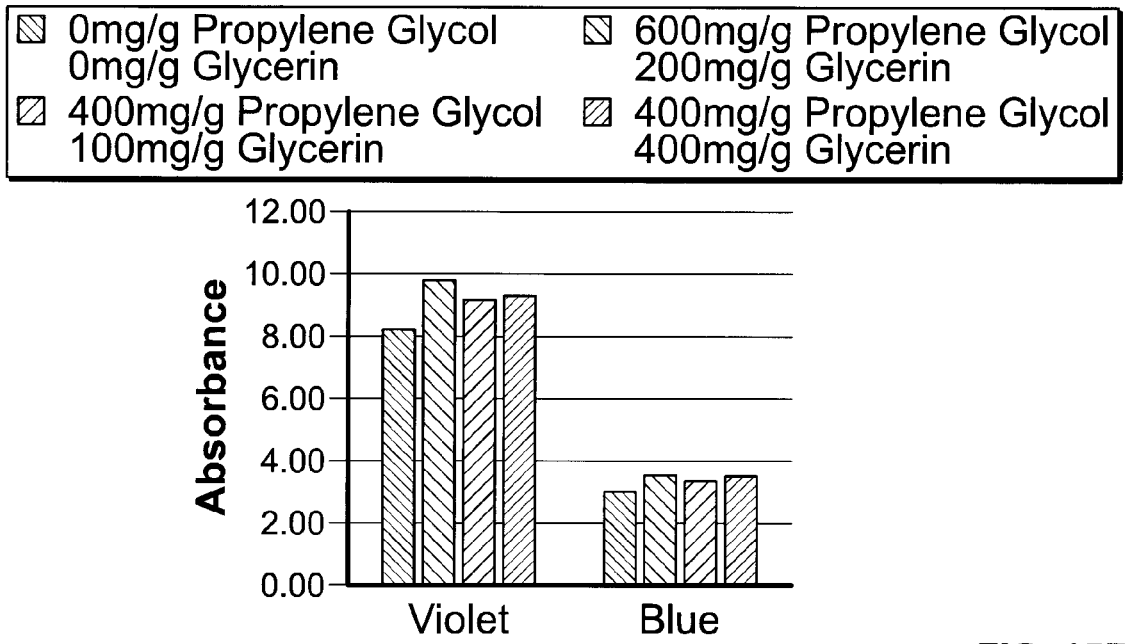
Figure 15C:
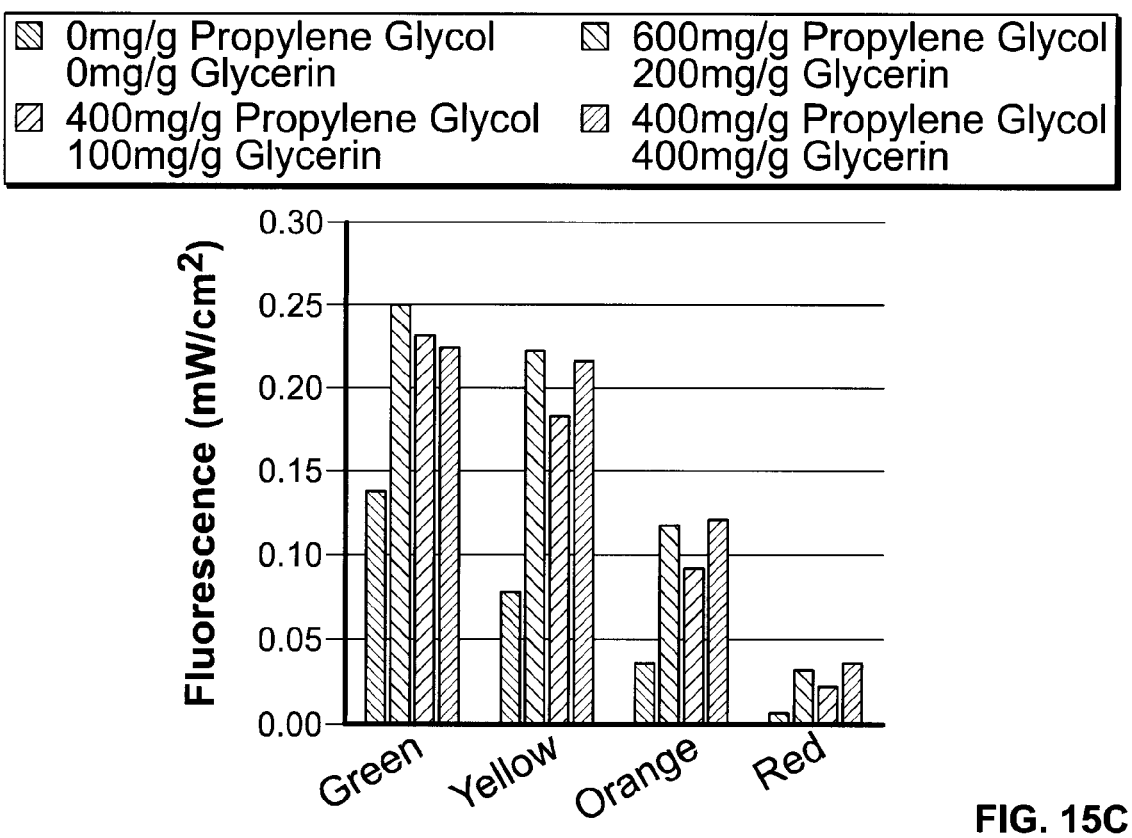

The results from the in-solution testing are presented in FIG. 15A and Table 21 with respect to the overall fluorescence output of the illuminated test solutions, while the color output information from the illuminated test solutions is presented in FIG. 15B and FIG. 15C together with Table 22.

TABLE 21

Fluorescence of Gel D2 - scaling of propylene glycol (PG) and glycerin - in solution

| Gel D2 Sample | Time/Fluorescence | | | | | | | | | | | |
|---|---|---|---|---|---|---|---|---|---|---|---|---|
| | 0.00 | 0.50 | 1.00 | 1.50 | 2.00 | 2.50 | 3.00 | 3.50 | 4.00 | 4.50 | 5.00 | Avg |
| 0 mg/g PG 0 mg/g Glycerin | 0.92 | 0.92 | 0.89 | 0.88 | 0.88 | 0.86 | 0.83 | 0.82 | 0.78 | 0.76 | 0.73 | 0.84 |
| 600 mg/g PG 200 mg/g Glycerin | 2.16 | 2.13 | 2.10 | 2.08 | 2.06 | 2.04 | 2.03 | 2.00 | 1.98 | 1.98 | 1.92 | 2.04 |
| 400 mg/g PG 100 mg/g Glycerin | 1.86 | 1.82 | 1.80 | 1.78 | 1.76 | 1.74 | 1.74 | 1.71 | 1.66 | 1.64 | 1.60 | 1.74 |
| 400 mg/g PG 400 mg/g Glycerin | 2.17 | 2.11 | 2.07 | 2.04 | 2.00 | 1.95 | 1.90 | 1.86 | 1.85 | 1.80 | 1.75 | 1.96 |

TABLE 22

Fluorescence of Gel D2 - scaling, in solution, of propylene glycol (PG) and glycerin - color output

| Color | 0 mg/g PG 0 mg/g Glycerin | 600 mg/g PG 200 mg/g Glycerin | 400 mg/g PG 100 mg/g Glycerin | 400 mg/g PG 400 mg/g Glycerin |
|---|---|---|---|---|
| violet | 8.21 | 9.78 | 9.16 | 9.30 |
| blue | 3.02 | 3.54 | 3.35 | 3.51 |
| green | 0.14 | 0.25 | 0.23 | 0.22 |
| yellow | 0.08 | 0.22 | 0.18 | 0.22 |
| orange | 0.04 | 0.12 | 0.09 | 0.12 |
| red | 0.01 | 0.03 | 0.02 | 0.04 |

The results from the in-solution PG scaling indicated that with adding an increased level of PG (600 mg versus 400 mg), an increase in the overall fluorescence could be obtained, and a similar effect could also be achieved with adding an increased level of glycerin (although the effect was not a dramatic). Regarding the color output from the illuminated PG-glycerin chromophore-contain solutions, each solution produced a significant larger amount of green, yellow, orange and red fluorescence compared to the solution lacking any added PG or glycerin. Differences, however, in the fluorescence color output profile as between the test solutions was noticeable, for example, the test solution containing the 400 mg/g PG:100 mg/g glycerin added combination produced a lower amount of yellow, orange and red relative to the other additive-containing test solutions.

Given the results from the first round of PG scaling in-solution testing, testing for scaling of PG in a gel composition was undertaken. First, a gel B was prepared by mixing 18.1 mg/g carbopol into water for 3 hours, and adding base to the solution (to pH 5.0). A sample of D1 gel was also prepared using the same procedure and adding 436 mg/g glycerin as well. The remaining three gels, A) 600 mg/g Propylene Glycol and 200 mg/g Glycerin, B) 400 mg/g Propylene Glycol and 100 mg/g Glycerin, and C) 400 mg/g Propylene Glycol and 400 mg/g Glycerin were prepared by adding the appropriate amounts of glycerin and PG to the gel B and mixing thoroughly. To each of gel sample, 327 µg/g of Eosin Y was added, and prior to the gels being illuminated, 1% sodium bicarbonate was added to the gel mixture.

Figure 15D:
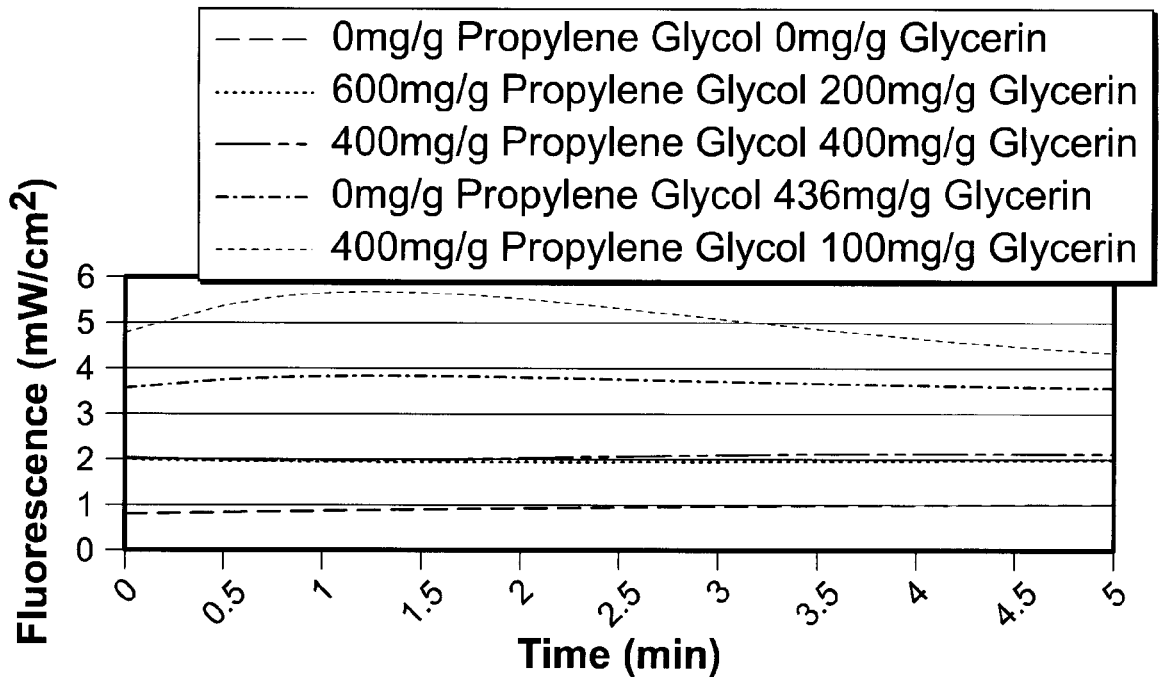
Figure 15E:
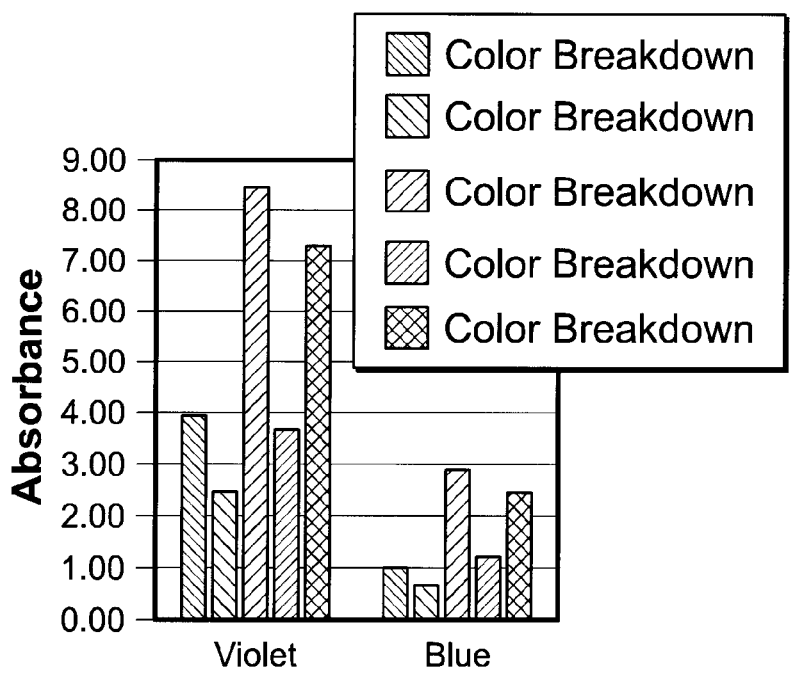
Figure 15F:
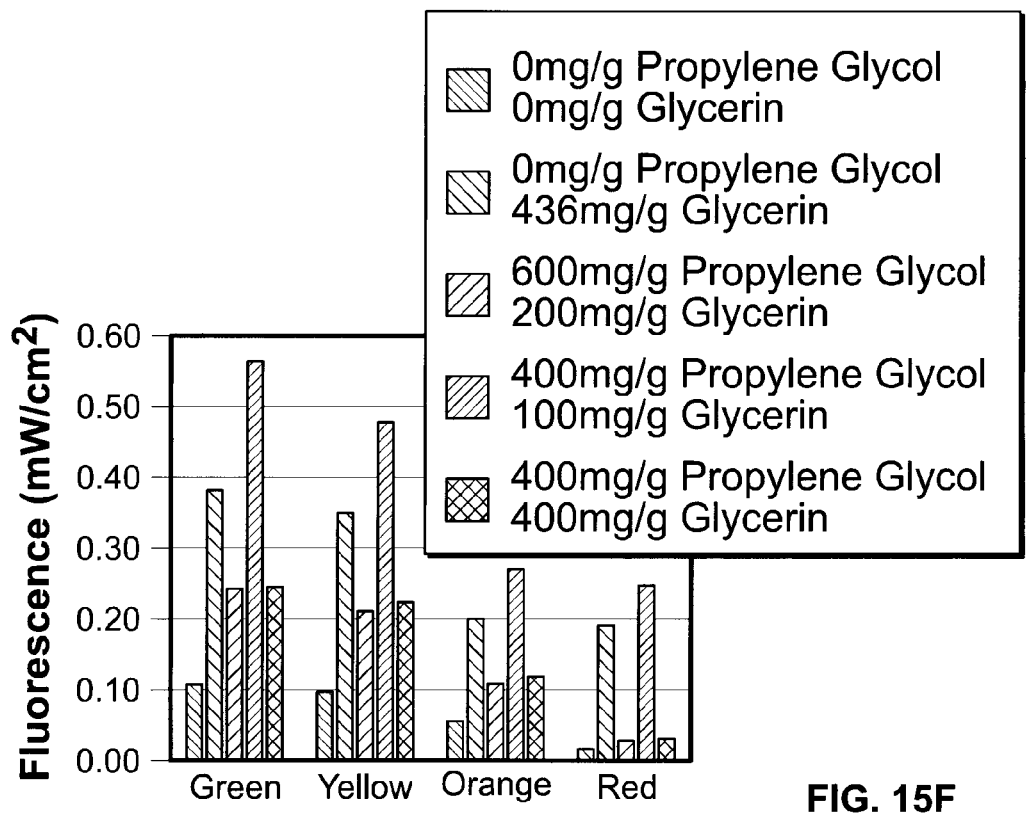

Each of the gel samples were illuminated as per the procedure described in Example 9, with the illumination period lasting for 5 minutes for each sample. The results from the in-gel testing are presented in FIG. 15D and Table 23 with respect to the overall fluorescence output of the illuminated test gels, while the color output information from the illuminated test gels is presented in FIG. 15E and FIG. 15F together with Table 24.

TABLE 23

Fluorescence of Gel D2 - scaling of propylene glycol (PG) and glycerin - in gel

| Gel D2 Sample | Time/Fluorescence | | | | | | | | | | | |
|---|---|---|---|---|---|---|---|---|---|---|---|---|
| | 0.00 | 0.50 | 1.00 | 1.50 | 2.00 | 2.50 | 3.00 | 3.50 | 4.00 | 4.50 | 5.00 | Avg |
| 0 mg/g PG 0 mg/g Glycerin | 0.79 | 0.84 | 0.86 | 0.88 | 0.92 | 0.94 | 0.95 | 0.97 | 0.98 | 0.99 | 1.00 | 0.92 |
| 0 mg/g PG 436 mg/g Glycerin | 3.57 | 3.76 | 3.83 | 3.83 | 3.79 | 3.75 | 3.72 | 3.68 | 3.64 | 3.57 | 3.54 | 3.70 |
| 600 mg/g PG 200 mg/g Glycerin | 1.98 | 1.96 | 1.94 | 1.95 | 1.94 | 1.95 | 1.94 | 1.96 | 1.97 | 1.99 | 2.01 | 1.96 |
| 400 mg/g PG 100 mg/g Glycerin | 4.79 | 5.40 | 5.69 | 5.68 | 5.55 | 5.34 | 5.11 | 4.89 | 4.67 | 4.51 | 4.35 | 5.09 |
| 400 mg/g PG 400 mg/g Glycerin | 2.02 | 1.98 | 1.97 | 2.00 | 2.04 | 2.05 | 2.08 | 2.11 | 2.12 | 2.13 | 2.12 | 2.06 |

TABLE 24

Fluorescence of Gel D2- scaling, in gel, of propylene glycol (PG) and glycerin - color output

| Color | 0 mg/g PG 0 mg/g Glycerin | 0 mg/g PG 436 mg/g Glycerin | 600 mg/g PG 200 mg/g Glycerin | 400 mg/g PG 100 mg/g Glycerin | 400 mg/g PG 400 mg/g Glycerin |
|---|---|---|---|---|---|
| violet | 3.39 | 2.47 | 8.44 | 3.67 | 7.29 |
| blue | 1.00 | 0.65 | 2.90 | 1.21 | 2.47 |
| green | 0.11 | 0.38 | 0.24 | 0.56 | 0.25 |
| yellow | 0.10 | 0.35 | 0.21 | 0.48 | 0.22 |
| orange | 0.06 | 0.20 | 0.11 | 0.27 | 0.12 |
| red | 0.02 | 0.19 | 0.03 | 0.25 | 0.03 |

The results from the in-gel testing indicated that the sample (B) having 400 mg/g Propylene Glycol and 100 mg/g Glycerin performed the best with respect to an amount of overall fluorescence output (see FIG. 15D) as well as the amount of fluorescence for each of the green, yellow, orange and red colors. Interestingly, the gels that had the increased levels of PG, their output of fluorescence was not as great as the sample (B), even though the results from the in-solution testing implied that the opposite should be the case. Noteworthy was the fact that gel samples with the higher levels of PG content became very liquid-like upon being illuminated, and it was concluded that these high-PG content gels would have too high a PG in order to function effectively as a gel that would retain some degree of its physical stickiness during a treatment process.

In a further experiment to evaluate the physical characteristics of the test gels (A) to (C) described above, a consistent size aliquot of each gel was applied onto a hand and held upside down for 1 minute. Observations of each gel were done to determine their consistency. All of the test gels were found to be easy to spread, and would stick to the hand when held upside down. The gel B had a firm feel, and could be removed with paper towel easily, while the D1 gel was sticky and was harder to remove with a paper towel. Test gels (A) and (C) were both liquid-like, whereas test gel (B) was found to behave similar to the gel B sample and was very easy to remove despite its having a definite gel consistency.

Example 16

Scaling of Bicarbonate in Presence of Glycerol and Propylene Glycol

In a further round of testing, an evaluation was performed with respect to determining an amount of sodium bicarbonate that could be added to a D2 gel that containing 654 mg/g glycerin and 234 mg/g propylene glycol (roughly equivalent to the sample (A) gel test in Example 15, second round).

To perform the experiment, a series of D2 gel samples were prepared, each having a 3× amount of Eosin Y chromophore. To each gel sample, just prior to being illuminated, an amount of sodium bicarbonate was added. The values of sodium bicarbonate were 0%, 0.1%, 0.5%, 1.0%, 2.0%, 5.0%, and 10.0%. The contents of the given gel were mixed for about 1 minute just before illumination began. The gel was then illuminated under the KLOX blue lamp for 5 minutes, and the fluorescence of the gel was measured in accordance with the procedure detailed in Example 9. The results for the overall fluorescence output of the tested gel samples are presented in FIG. 16 and Table 25.

Figure 16:
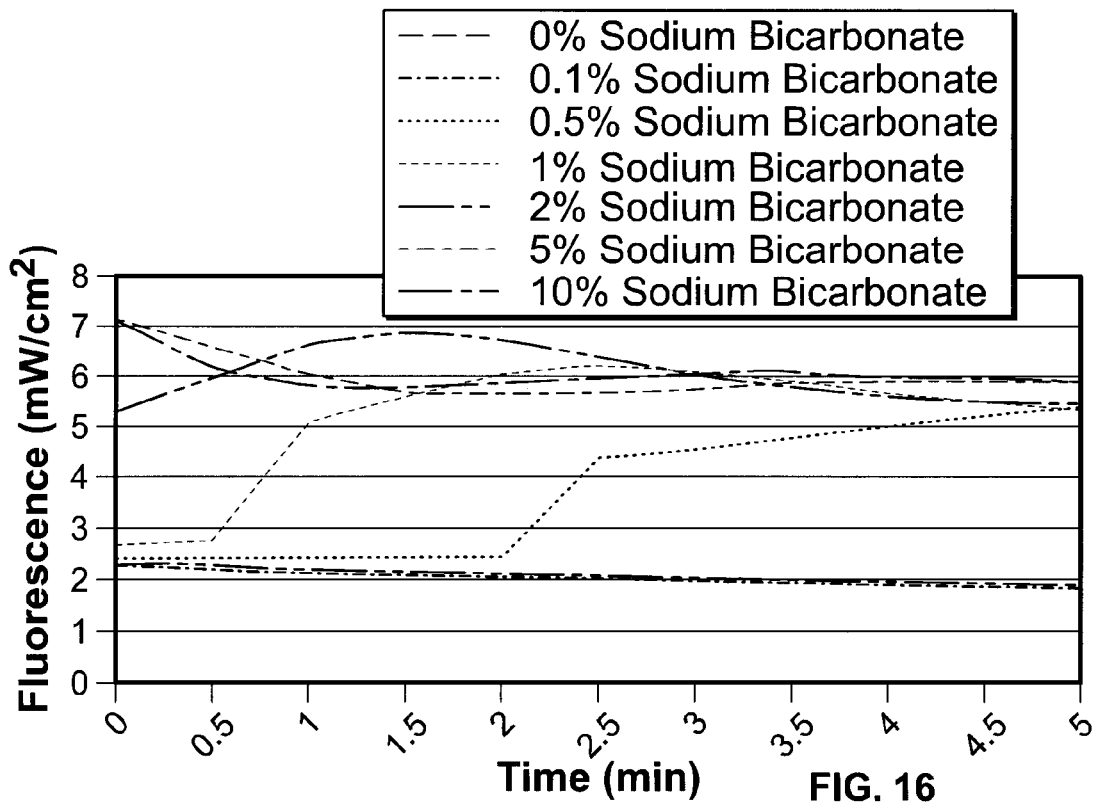
FIG. 16 depicts the impact of varying concentrations of sodium bicarbonate on the fluorescence of gel D2 with 327 µg/g Eosin Y (Example 16).

As can be seen from FIG. 16, addition of the low amounts (0.1% and 0.5%) of sodium bicarbonate either had no or a delayed effect on increasing the level of fluorescence of the D2 gel sample. Overall, as can be seen in Table 25, the results indicated that the more sodium bicarbonate added, the faster the increase in fluorescence occurred, along with the achieving a higher level per se. For increasing the fluorescence level of a D2 gel, without delay, using a bicarbonate salt such as 2% sodium bicarbonate served such a purpose, as adding a higher amount of such a bicarbonate would yield an equivalent result.

Example 17

Ratio of Glycerol:Propylene Glycol, and Addition of Parabens to Increase Fluorescence In a further round of experiments, alterations were introduced into D2 gel compositions with respect to adding different ratios of PG to glycerin and, as well, adding further components to the gel mixture in order to sustain the fluorescence output of the gel at an elevated level. Previously, in the preparation of gel B, an amount (about 2 mL) of 10 N NaOH would be added in order to basify the gel composition, however, doing so often resulted in a lack of gel formation. As such, attempts were made at adding various components of a gel together, ultimately to form a D2 gel composition, followed thereafter by basification. The gel samples that were prepared for testing in this Example all had a 3× amount of Eosin Y added as the chromophore. The gels made, based on previous successful results were as described in Table 26 below.

TABLE 26

Gel D2 mixtures - alternative ratios of PEG to glycerol - parabens

| D2 | D2 with Methyl Paraben and Propyl Paraben (Gel E) |
|---|---|
| D2 with 500 mg/g PG | D2 with 600 mg/g PG |
| D2 with 500 mg/g PG 150 mg/g Glycerin | D2 with 300 mg/g PG 50 mg/g Glycerin |
| D2 with 400 mg/g PG 200 mg/g Glycerin | D2 with 200 mg/g PG 200 mg/g Glycerin |

After the D2 gel samples were prepared, 1% sodium bicarbonate was added (in powder form) and mixed for 1 minute with each gel sample before being illuminated with the KLOX blue lamp for 10 minutes with 5 cm distance between the gel and the lamp (in accordance with the procedure detailed in Example 9).

TABLE 25

Scaling of Sodium Bicarbonate (NaBicarb) in Gel D2 - Fluorescence output

| Sample/ % NaBicarb | Time/Fluorescence | | | | | | | | | | | |
|---|---|---|---|---|---|---|---|---|---|---|---|---|
| | 0 | 0.5 | 1 | 1.5 | 2 | 2.5 | 3 | 3.5 | 4 | 4.5 | 5 | AVERAGE |
| 0% | 2.28 | 2.24 | 2.16 | 2.10 | 2.05 | 2.03 | 1.99 | 1.96 | 1.92 | 1.89 | 1.84 | 2.04 |
| 0.10% | 2.28 | 2.18 | 2.12 | 2.07 | 2.02 | 2.00 | 1.96 | 1.93 | 1.88 | 1.85 | 1.82 | 2.01 |
| 0.50% | 2.42 | 2.39 | 2.38 | 2.39 | 2.44 | 4.37 | 4.52 | 4.78 | 5.00 | 5.22 | 5.37 | 3.75 |
| 1% | 2.64 | 2.76 | 5.08 | 5.62 | 6.04 | 6.20 | 6.09 | 5.90 | 5.63 | 5.51 | 5.33 | 5.16 |
| 2% | 5.29 | 5.94 | 6.63 | 6.87 | 6.72 | 6.37 | 6.03 | 5.77 | 5.60 | 5.49 | 5.45 | 6.01 |
| 5% | 7.13 | 6.59 | 6.03 | 5.67 | 5.64 | 5.67 | 5.70 | 5.87 | 5.91 | 5.92 | 5.88 | 6.00 |
| 10% | 7.11 | 6.17 | 5.79 | 5.75 | 5.85 | 5.98 | 6.02 | 6.11 | 5.99 | 6.00 | 5.88 | 6.06 |

Figure 17A:
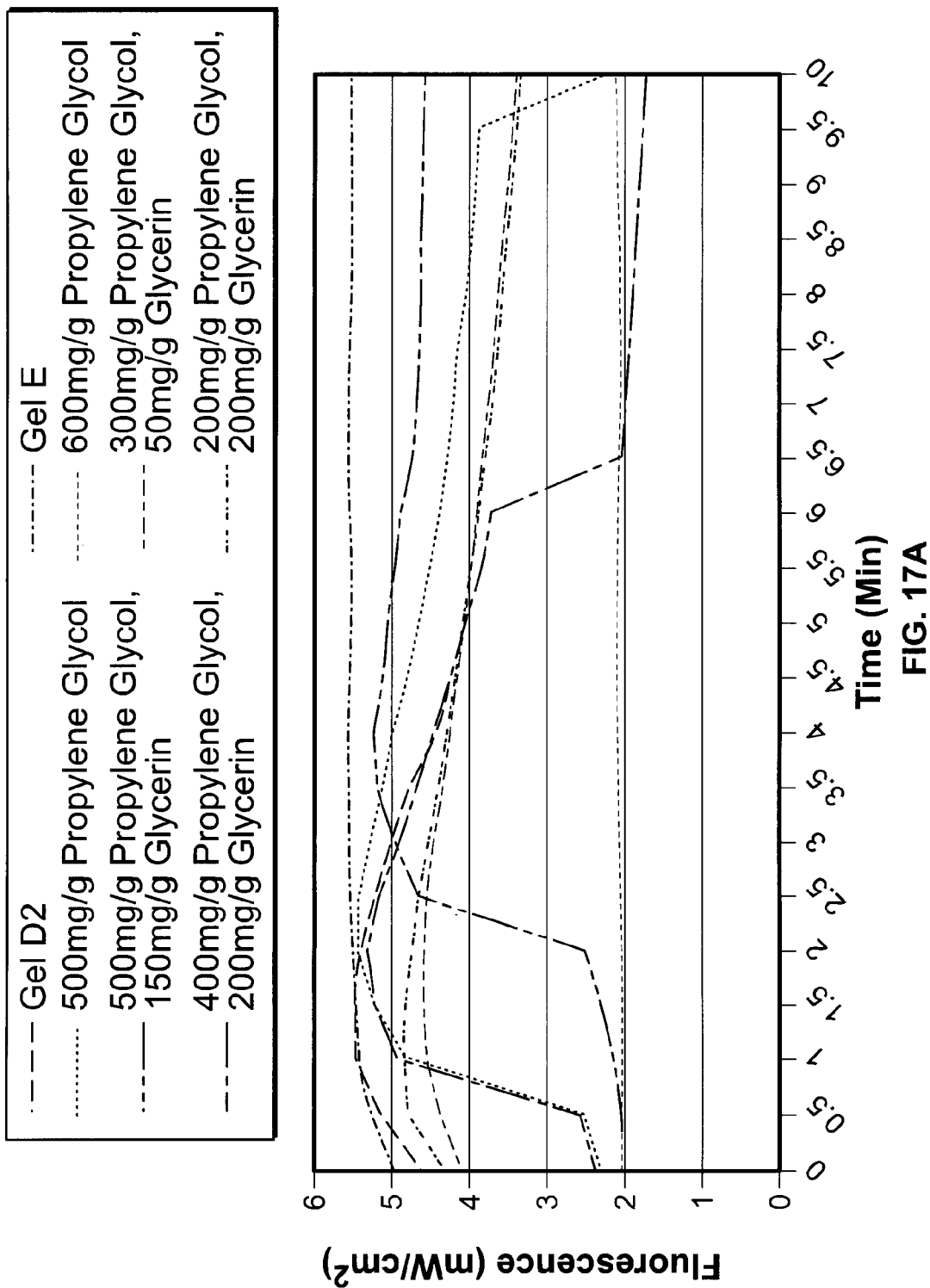
FIGS. 17A, 17B and 17C depict the impact of varying concentrations of propylene glycol and glycerin on the fluorescence of gel D2 and of varying concentrations of propylene glycol, glycerin, and parabens on the fluorescence of gel E. Both gels have 327 µg/g Eosin Y (Example 17).
Figure 17B:
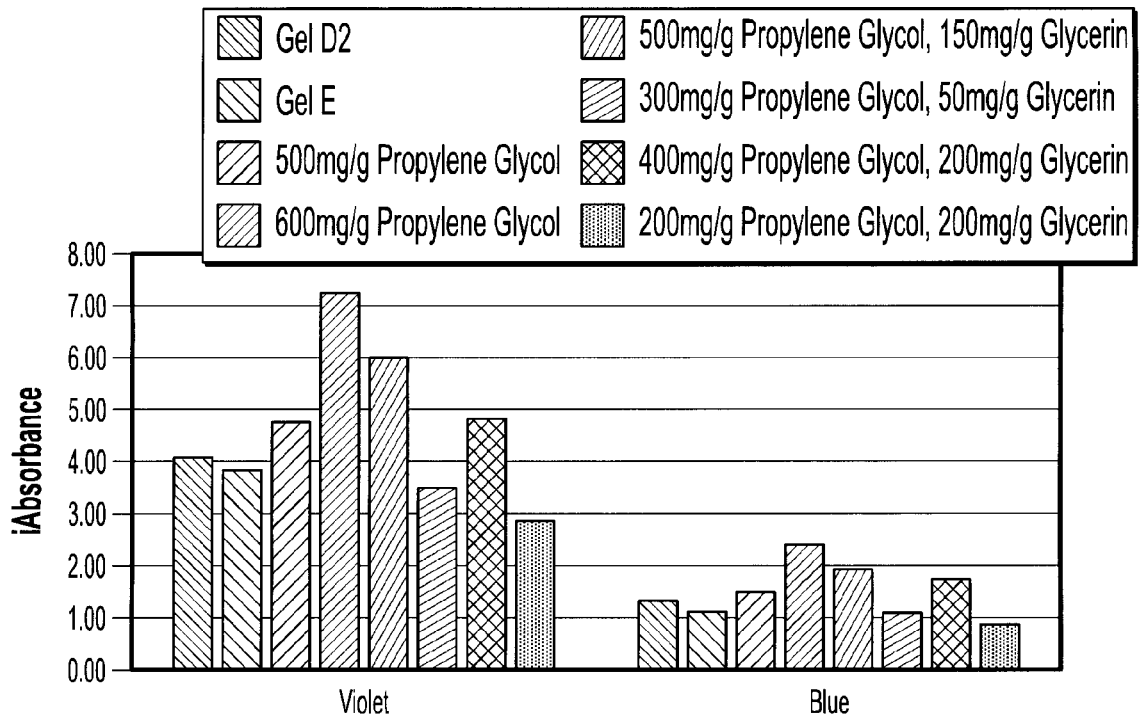
Figure 17C:
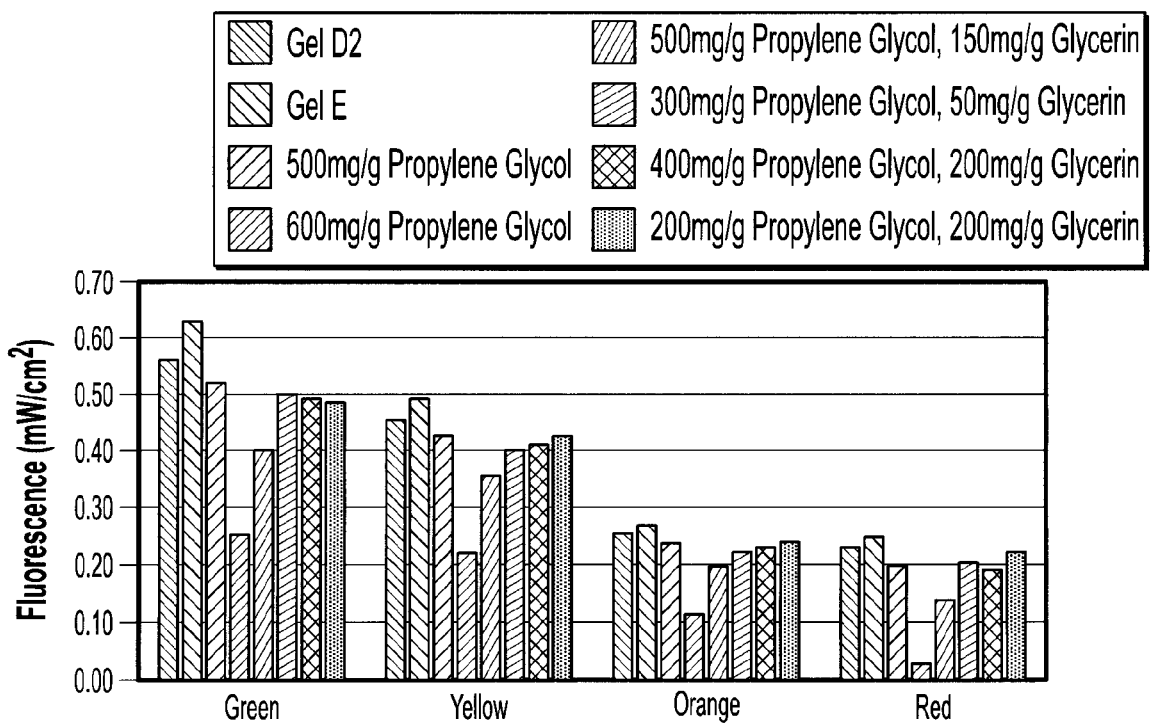

The results from the gel testing are presented in FIG. 17A and Table 27 with respect to the overall fluorescence output of the illuminated test gels, while the color output information from the illuminated test gels is presented in FIG. 17B and FIG. 17C together with Table 28.

TABLE 27

Gel D2 - Fluorescence output - variable ratio of PG to glycerin - parabens

| D2 gel sample | Time/Fluorescence | | | | | | | | | | |
|---|---|---|---|---|---|---|---|---|---|---|---|
| | 0 | 0.5 | 1 | 1.5 | 2 | 2.5 | 3 | 3.5 | 4 | 4.5 | 5 |
| 400 mg/g PG 100 mg/g Glycerin | 4.61 | 5.13 | 5.45 | 5.48 | 5.41 | 5.21 | 5.01 | 4.77 | 4.42 | 4.23 | 4.07 |
| Methyl Paraben Propyl Paraben (Gel E) | 4.98 | 5.22 | 5.41 | 5.44 | 5.51 | 5.55 | 5.54 | 5.55 | 5.57 | 5.54 | 5.52 |
| 500 mg/g PG | 2.30 | 2.52 | 4.81 | 5.21 | 5.43 | 5.42 | 5.28 | 5.11 | 4.98 | 4.79 | 4.64 |
| 600 mg/g PG | 2.03 | 2.00 | 2.01 | 2.00 | 2.03 | 2.04 | 2.05 | 2.06 | 2.07 | 2.08 | 2.08 |
| 500 mg/g PG 150 mg/g Glycerin | 2.03 | 2.01 | 2.12 | 2.28 | 2.49 | 4.65 | 4.96 | 5.19 | 5.22 | 5.11 | 5.05 |
| 300 mg/g PG 50 mg/g Glycerin | 4.09 | 4.37 | 4.54 | 4.59 | 4.58 | 4.54 | 4.46 | 4.34 | 4.27 | 4.16 | 4.06 |
| 400 mg/g PG 200 mg/g Glycerin | 2.36 | 2.56 | 4.92 | 5.21 | 5.31 | 5.17 | 4.89 | 4.68 | 4.46 | 4.24 | 4.03 |
| 200 mg/g PG 200 mg/g Glycerin | 4.31 | 4.78 | 4.84 | 4.82 | 4.73 | 4.66 | 4.52 | 4.40 | 4.28 | 4.18 | 4.07 |

| D2 gel sample | Time/Fluorescence | | | | | | | | | | |
|---|---|---|---|---|---|---|---|---|---|---|---|
| | 5.5 | 6 | 6.5 | 7 | 7.5 | 8 | 8.5 | 9 | 9.5 | 10 | AVG |
| 400 mg/g PG 100 mg/g Glycerin | | | | | | | | | | | 4.89 |
| Methyl Paraben Propyl Paraben (Gel E) | 5.51 | 5.55 | 5.55 | 5.55 | 5.54 | 5.52 | 5.52 | 5.51 | 5.52 | 5.53 | 5.48 |
| 500 mg/g PG | 4.51 | 4.36 | 4.28 | 4.20 | 4.15 | 4.03 | 3.96 | 3.92 | 3.87 | 2.14 | 4.28 |
| 600 mg/g PG | 2.07 | 2.06 | 2.05 | 2.04 | 2.03 | 2.05 | 2.05 | 2.08 | 2.08 | 2.11 | 2.05 |
| 500 mg/g PG 150 mg/g Glycerin | 4.96 | 4.89 | 4.73 | 4.68 | 4.64 | 4.62 | 4.62 | 4.60 | 4.57 | 4.57 | 4.19 |
| 300 mg/g PG 50 mg/g Glycerin | 3.96 | 3.86 | 3.81 | 3.76 | 3.68 | 3.61 | 3.55 | 3.48 | 3.43 | 3.39 | 4.03 |
| 400 mg/g PG 200 mg/g Glycerin | 3.83 | 3.72 | 2.02 | 1.98 | 1.92 | 1.87 | 1.82 | 1.79 | 1.75 | 1.70 | 3.34 |
| 200 mg/g PG 200 mg/g Glycerin | 3.97 | 3.86 | 3.79 | 3.70 | 3.62 | 3.56 | 3.51 | 3.43 | 3.38 | 3.32 | 4.08 |

TABLE 28

Gel D2 - Fluorescence color output - variable ratio of PG to glycerin - parabens

| Color | D2 Gel type | | | | | | | |
|---|---|---|---|---|---|---|---|---|
| | D2 | D2 with Methyl Paraben, Propyl Paraben (Gel E) | D2 with 500 mg/g PG | D2 with 600 mg/g PG | D2 with 500 mg/g PG, 150 mg/g Glycerin | D2 with 300 mg/g PG, 50 mg/g Glycerin | D2 with 400 mg/g PG, 200 mg/g Glycerin | D2 with 200 mg/g PG, 200 mg/g Glycerin |
| violet | 4.08 | 3.83 | 4.76 | 7.25 | 6.00 | 3.48 | 4.82 | 2.84 |
| blue | 1.31 | 1.10 | 1.48 | 2.39 | 1.91 | 1.07 | 1.72 | 0.83 |
| green | 0.56 | 0.63 | 0.52 | 0.25 | 0.40 | 0.50 | 0.49 | 0.49 |
| yellow | 0.45 | 0.49 | 0.43 | 0.22 | 0.35 | 0.40 | 0.41 | 0.43 |
| orange | 0.25 | 0.27 | 0.24 | 0.11 | 0.20 | 0.22 | 0.23 | 0.24 |
| red | 0.23 | 0.25 | 0.20 | 0.03 | 0.14 | 0.20 | 0.19 | 0.22 |

The results indicated that with an insufficient gel amount due to too much PG being added (e.g., 600 mg/g) the gel fluorescence decreased, or would not react with sodium bicarbonate effectively. Additionally, the results also indicated an amount of glycerin was required as opposed to pure propylene glycol, in order to maximize fluorescence. Also, the ratio of gel to additive is very important and it seems that 400-500 mg/g of the PG added to the D2 gel composition provided a better performing D2 gel in terms of overall fluorescence output as well as across the range of the color spectrum. Furthermore, adding a small amount of parabens to the D2 gel allowed the gel to reach the same maximum fluorescence of the other gels, but the gel would not degrade (i.e., lose its structural characteristics), even after 10 minutes of illumination.

Example 18

Further Testing of Parabens

As the addition of parabens to the D2 gel provided an improved and prolonged performance of the gel with respect to the gel's fluorescence output, a further set of tests were performed to evaluate whether an addition of methyl and propyl parabens, either with or without sodium bicarbonate being added to the gel mixture, would have on the D2 gel.

To perform the experiment, 10 grams of D2 gel was made with 3× Eosin Y added. This gel was then divided into two equal batches, one with no further components being added, and the other had 1.01 mg/g methyl paraben and 0.54 mg/g propyl paraben in combination. The first and second batches containing either no parabens or the parabens were then further subdivided into two groups (i.e., a total of four gels) with one member of each group being kept as is, while the other member of the group having 1% sodium bicarbonate added to it. If sodium bicarbonate were added, then the gel was mixed with the sodium bicarbonate for 1 minute before starting the illumination period.

The gels were illuminated for a period of 5 minutes and at a distance of 5 cm from the gel surface and the fluorescence results were captured on a spectrophotometer as per Example 9.

Figure 18A:
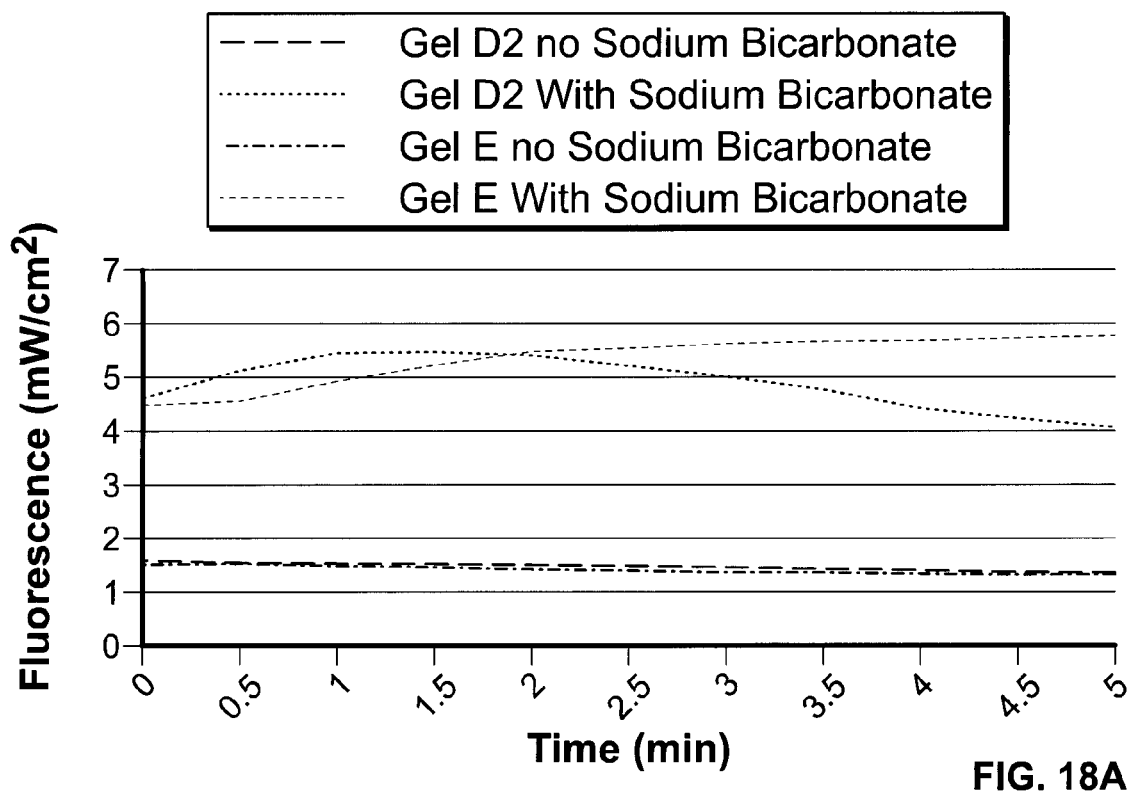
FIGS. 18A, 18B and 18C depict the impact of methyl and propyl parabens on the fluorescence of gel E in the presence and absence of sodium bicarbonate (SB). Gel D2 lacks parabens, but gel E contains parabens. Both gels have 327 µg/g Eosin Y (Example 18).
Figure 18B:
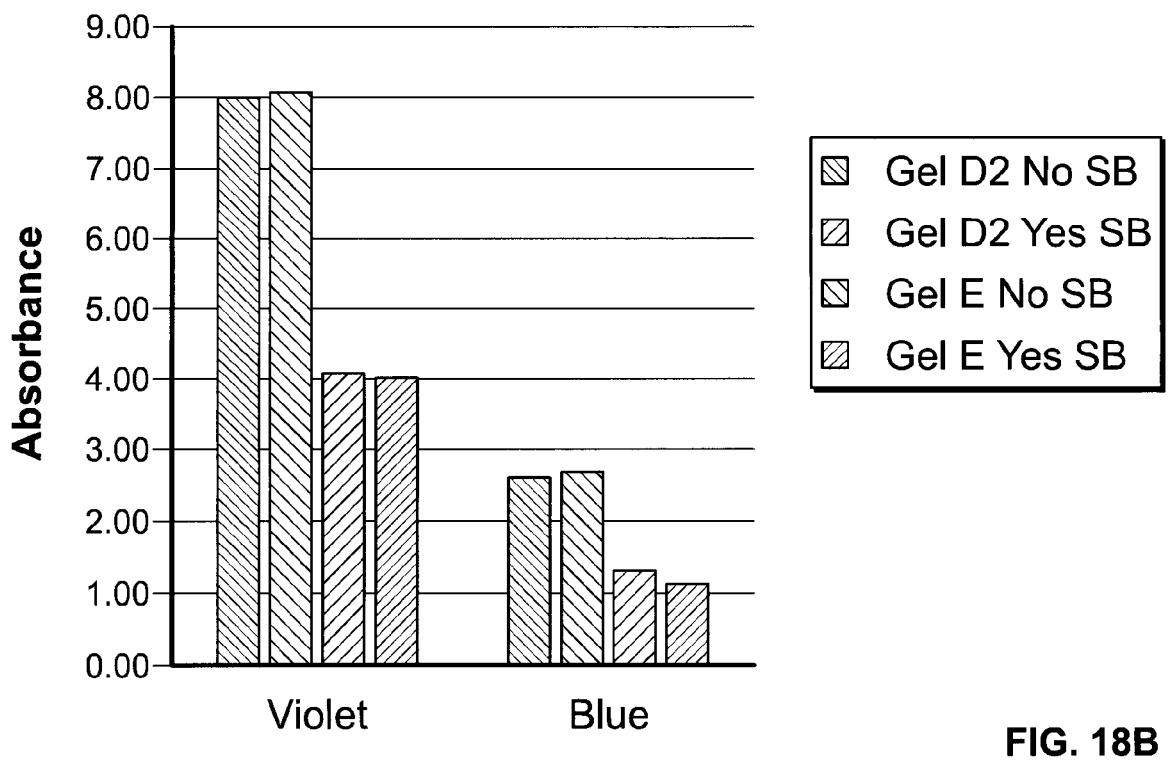
Figure 18C:
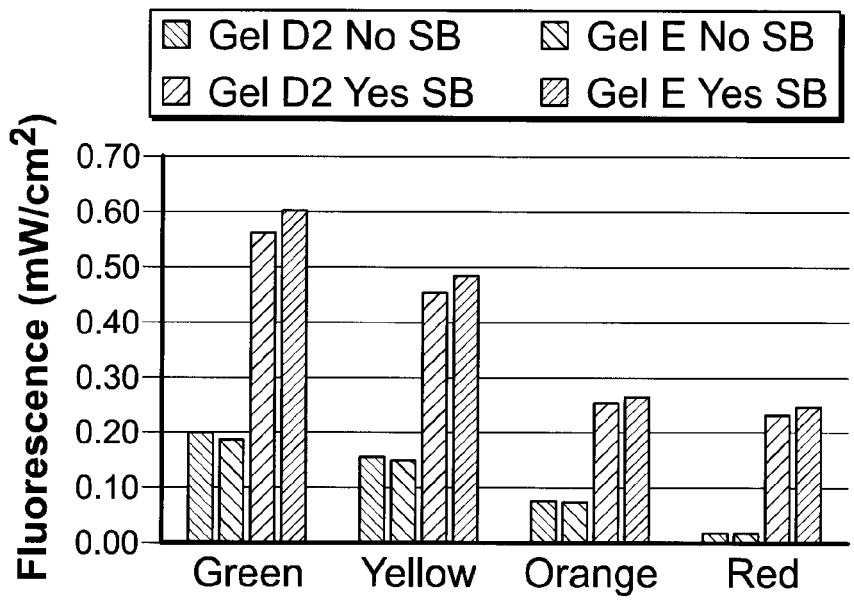

The results from the parabens-containing D2 gel (designated as Gel E) testing are presented in FIG. 18A and Table 29 with respect to the overall fluorescence output of the illuminated test gels, while the color output information from the illuminated test gels is presented in FIG. 18B and FIG. 18C together with Table 30.

TABLE 30

Fluorescence color output of gels D2 and E, +/− sodium bicarbonate (SB)

| Color | Gel type | | | |
|---|---|---|---|---|
| | Gel D2 No SB | Gel E No SB | Gel D2 Yes SB | Gel E Yes SB |
| violet | 8.00 | 8.06 | 4.08 | 4.01 |
| blue | 2.60 | 2.68 | 1.31 | 1.12 |
| green | 0.20 | 0.19 | 0.56 | 0.60 |
| yellow | 0.16 | 0.15 | 0.45 | 0.48 |
| orange | 0.08 | 0.07 | 0.25 | 0.26 |
| red | 0.02 | 0.02 | 0.23 | 0.25 |

The results, as indicated in FIG. 18A and Table 29, regarding the overall fluorescence output of the tested gels indicated that regardless of the presence of parabens in the gels, the fluorescence output level is increased with the addition of the sodium bicarbonate; the parabens had no apparent effect on the level of fluorescence of the D2 gel or the Gel E compositions. Furthermore, comparing the results for the D2 gel versus gel E when both gels either had or lacked an addition of the 1% sodium bicarbonate, parabens did not appear to have any effect on the fluorescence color output spectrum or on the amount of any of the green, yellow, orange or red fluorescence emitted from the illuminated gels. The fluorescence of the gel E samples, containing the parabens, did not, however, degrade over the illumination period, indicating that a prolonged fluorescence exposure could be obtained by utilizing a parabens-containing gel composition such as gel E.

Example 19

Scaling of Chromophore Concentration in Presence of Bicarbonate, Glyercol, Propylene Glycol and Parabens A further evaluation was performed with respect to the performance of the parabens-containing gel E with respect to addressing what amount of chromophore might be added in order to induce a maximum yield of fluorescence from an illuminated gel E.

To perform the experiment, a batch of gel E was prepared, and after mixing, an amount of the chromophore Eosin Y was added, in solution, to each aliquot of the gel E batch so as to result in gel E samples having a final Eosin Y concentration being 2×, 3×, 4×, 5×, and 6× Eosin Y. Each of the gel samples was mixed well, and thereafter 2% sodium bicarbonate was added to the gels approximately 1 minute before the samples were illuminated for 10 minutes using the KLOX multi-LED blue light. Illumination and fluores-

TABLE 29

Fluorescence output of gels D2 and E, with or without sodium bicarbonate (SB)

| Gel type | Time/Fluorescence | | | | | | | | | | | |
|---|---|---|---|---|---|---|---|---|---|---|---|---|
| | 0 | 0.5 | 1 | 1.5 | 2 | 2.5 | 3 | 3.5 | 4 | 4.5 | 5 | AVG |
| D2 no SB | 1.58 | 1.54 | 1.53 | 1.52 | 1.50 | 1.49 | 1.46 | 1.43 | 1.40 | 1.37 | 1.36 | 1.47 |
| E no SB | 1.51 | 1.53 | 1.48 | 1.46 | 1.42 | 1.40 | 1.37 | 1.36 | 1.34 | 1.32 | 1.32 | 1.41 |
| D2 + SB | 4.61 | 5.13 | 5.45 | 5.48 | 5.41 | 5.21 | 5.01 | 4.77 | 4.42 | 4.23 | 4.07 | 4.89 |
| E + SB | 4.48 | 4.56 | 4.93 | 5.23 | 5.48 | 5.54 | 5.62 | 5.67 | 5.68 | 5.72 | 5.76 | 5.33 | cence analysis were performed as described in Example 9. The results from the experiment are presented in FIG. 19A with respect to the fluorescence output per gel over the illumination time period, while FIG. 19B shows the amount of blue light that is transmitted through the illuminated gel sample at time points over the course of the illumination period.

Figure 19A:
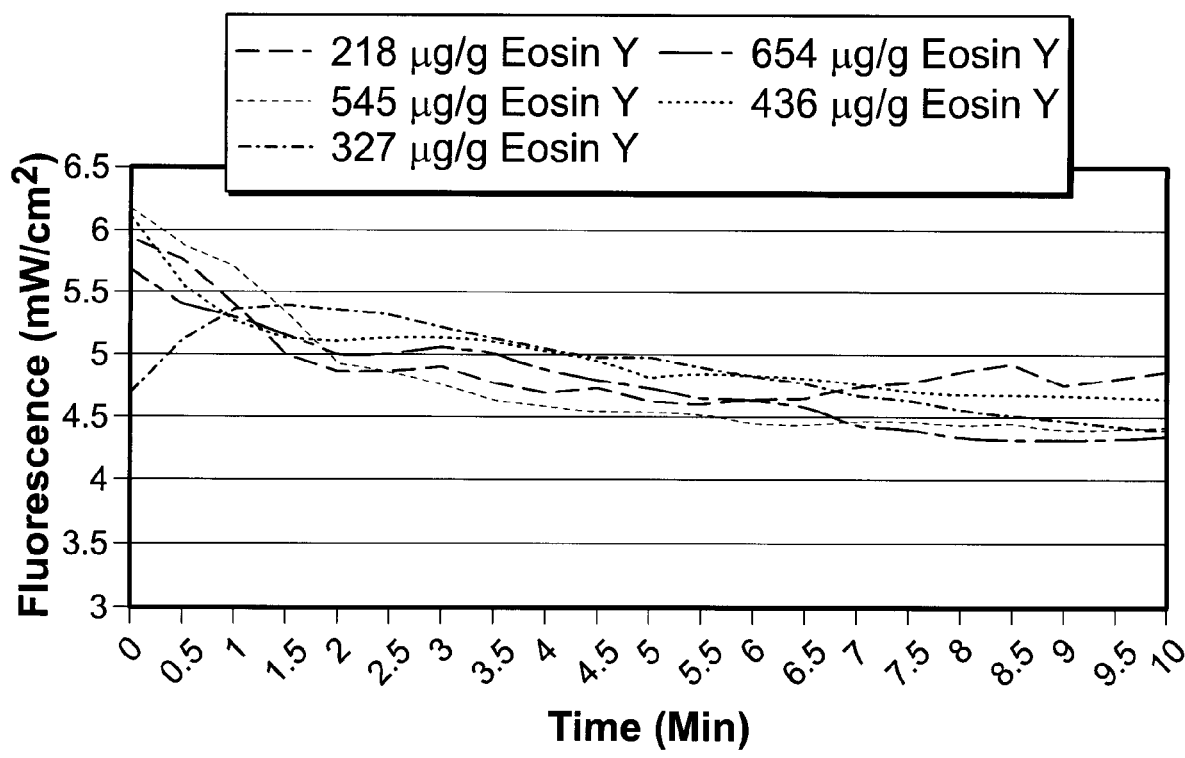
FIGS. 19A, 19B, 19C and 19D depict the impact of varying concentrations of Eosin Y on the fluorescence of gel E. Gel E contains parabens (Example 19).
Figure 19B:
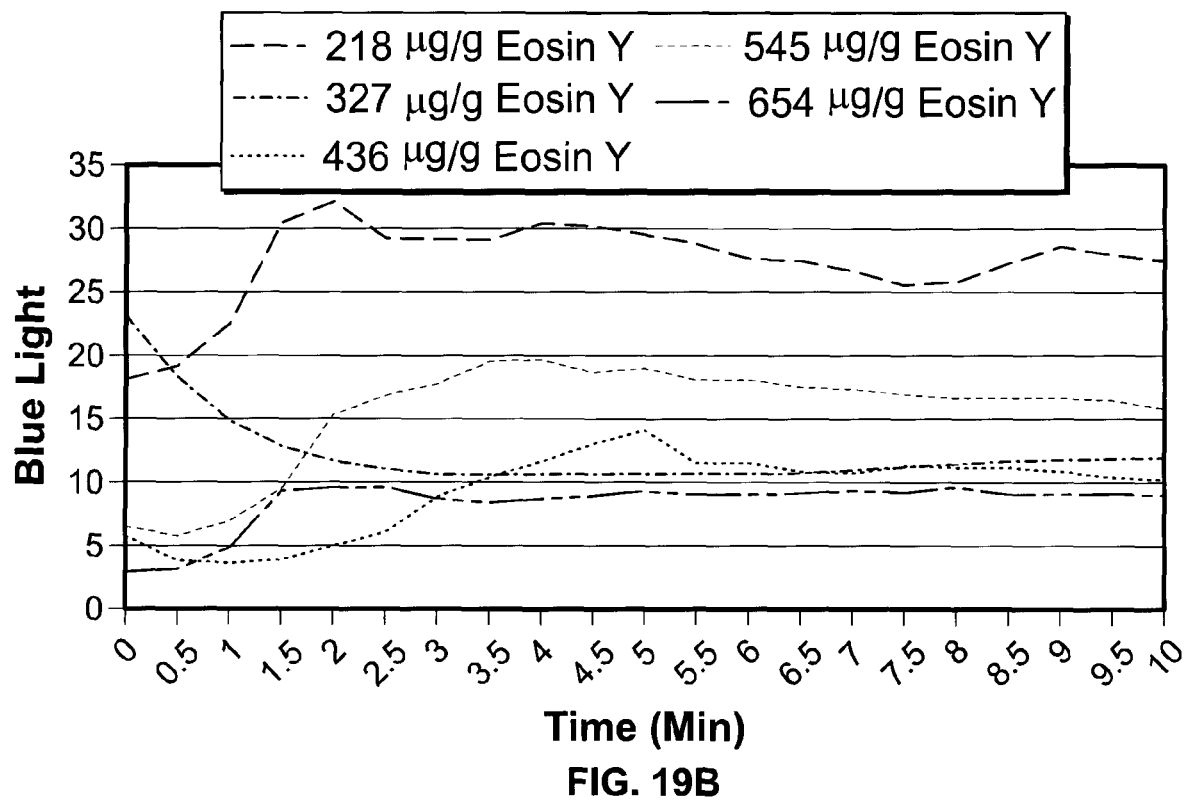

As can been seen from FIG. 19A, the results indicated that altering the Eosin Y concentration in the gel E composition may only have a minor effect on the fluorescence output of the gel E composition given that all of the tested gel samples had a fluorescence yield that stabilized between 4.5 and 5 mW/cm$^2$, in no particular order of concentration. Looking at FIG. 19B, blue light passing through the gel could serve as an indicator of how much of the illuminating light was converted into fluorescence due to the activity of the chromophore in the gel. At added chromophore concentrations of 3× and above, less blue light was transmitted through the given sample gel. However, the degree to which the lack of blue light transmittance at the 4×, 5× and 6× Eosin Y concentrations was simply due to a quenching effect of the chromophore presence was not determined.

A further experimental round was conducted to further determine an appropriate amount of chromophore to add to gel E in order to maximize fluorescence.

To perform the experiment, a gel E mixture was prepared as per the first round experiment, however, for this second round of testing additional Eosin Y chromophore concentrations were also tested, which included 0.5× and 1× Eosin Y. The gels were illuminated and data captured as per the first round experiment, and the results are presented in FIG. 19C with respect to the fluorescence output per gel over the illumination time period, while FIG. 19D shows the amount of blue light that is transmitted through the illuminated gel sample at time points over the course of the illumination period.

Figure 19C:
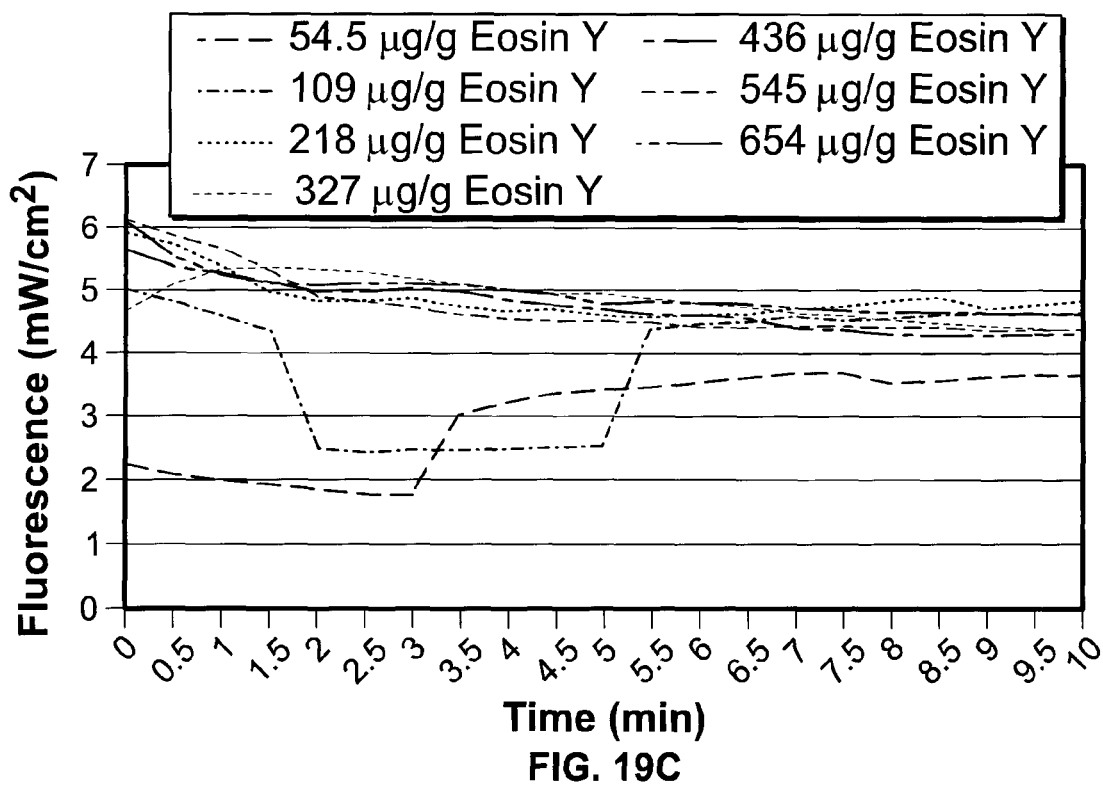
Figure 19D:
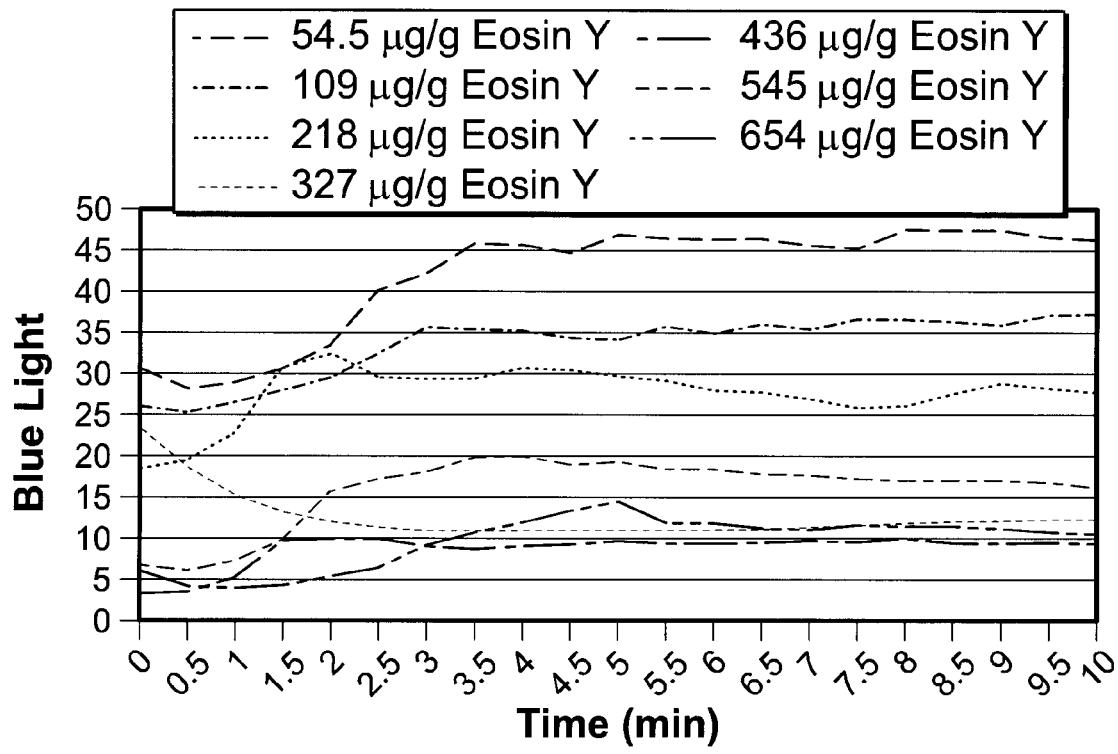

Referring to FIG. 19C, it can be seen that the adjusting the chromophore concentration to below 2× Eosin Y in the gel E resulted in a comparatively significant lower level of fluorescence yield and a higher level of transmittance of the blue light through the illuminated gel E samples. The blue light passing through however is greatly increased by lower Eosin Y concentrations.

Example 20

Components that May Affect Photobleaching Rate

As results from prior experimental rounds, whether in relation to ROS production or in relation to fluorescence generating capacity, indicated that some components may have a beneficial impact, a round of further testing was conducted in order to evaluate the effect that certain added components may have on a rate of photobleaching of the chromophore Eosin Y and fluorescence output in the context of the given gel mixture and illumination time period. The purpose of this experiment was to find out the ingredients responsible for increasing the bleaching time and the components that boost the fluorescence.

To perform the experiment, a gel D1 composition was prepared by mixing 18.1 grams of carbopol, 43.6 grams of glycerin and 54.59 grams of water, mixing and then adding a 3× amount of the Eosin Y chromophore followed by further mixing to form a uniform composition. Optionally, further components were mixed into the D1 gel, such as either PG or an amount of the divalent ion chelator EDTA. For comparative purposes, a gel mixture was also prepared, but having an amount of chromophore added (2× Eosin Y). To each prepared gel sample, an amount of sodium bicarbonate was added to provide for a final concentration of either 1% or 0.2% sodium bicarbonate in the gel mixture, and after mixing and incubation for approximately 1 minute, the given prepared gel sample was illuminated as described in Example 9 for a period of 10 minutes.

Figure 20A:
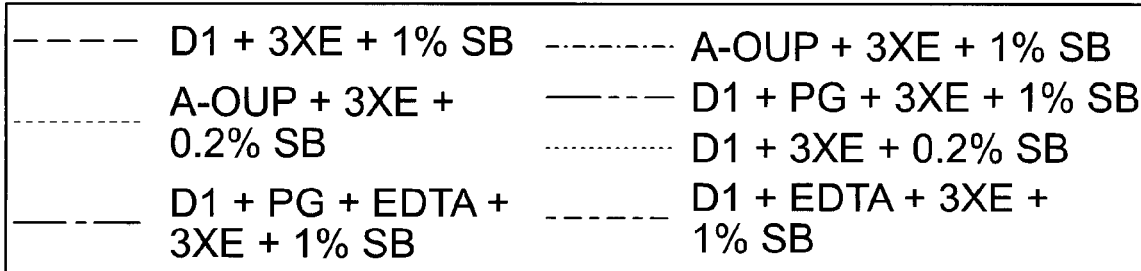
FIGS. 20A and 20B illustrate the impact of various components on the photobleaching of Eosin Y (327 µg/g (3XE)). The gel used is the D1 gel. Tested components include: urea peroxide (UP), sodium bicarbonate (SB), propylene glycol (PG), and EDTA. The D1 gel contains glycerin (Example 20).
Figure 20A:
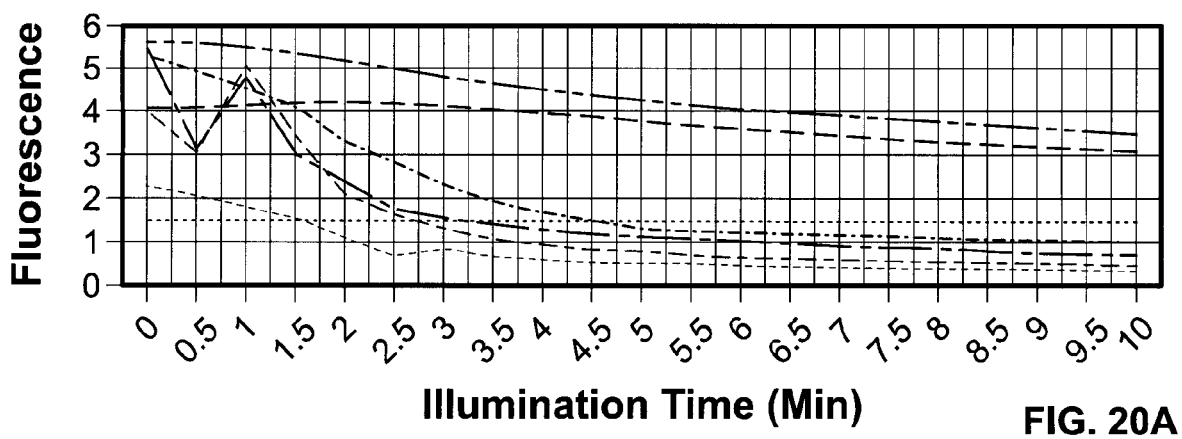
Figure 20B:
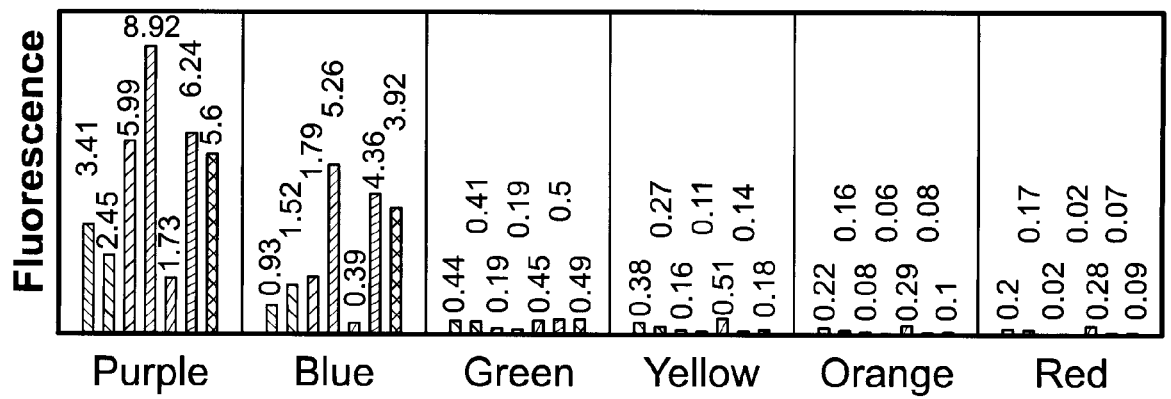

The results are presented in FIG. 20A and Table 31 with respect to the fluorescence output per gel over the illumination time period, while FIG. 20B and Table 32 provide the data with respect to the fluorescence color output across the visual spectrum range for each of the illuminated gel samples.

As can be seen from FIG. 20A and Table 31, the better performing gel compositions on a comparative basis were the D1 gels having the 1% sodium bicarbonate and, additionally, the PG added to the gel. Regarding the fluorescence color output, these two gels also show more green, yellow, orange and red fluorescence spectrum output. Regarding the gel A composition, which already contained EDTA, while its initial level of fluorescence could be elevated with an addition of the 1% sodium bicarbonate, its fluorescence output decreased rapidly to a level of those other gels to which EDTA was also added (see FIG. 20A). According to the result, an addition of glycerin and the PG resulted in an increase the fluorescence, while a presence of EDTA altered the performance of the gel composition by affecting the rate of photobleaching of the chromophore.

TABLE 31

Fluoresecence output of gels A and D1, with various additives

| Gel + additive | Time/Fluorescence output | | | | | | | | | | |
|---|---|---|---|---|---|---|---|---|---|---|---|
| | 0 | 0.5 | 1 | 1.5 | 2 | 2.5 | 3 | 3.5 | 4 | 4.5 | 5 |
| D1 + 3X YE + 1% SB | 4.07 | 4.07 | 4.15 | 4.20 | 4.20 | 4.18 | 4.13 | 4.05 | 3.97 | 3.89 | 3.77 |
| A 0% UP + 3X EY + 1% SB | 5.29 | 4.94 | 4.52 | 4.10 | 3.30 | 2.84 | 2.30 | 1.92 | 1.68 | 1.51 | 1.30 |
| D1 + PEG + 3X EY + 1% SB | 5.60 | 5.60 | 5.51 | 5.35 | 5.17 | 4.98 | 4.81 | 4.64 | 4.50 | 4.35 | 4.26 |
| D1 + EDTA + 3X EY + 1% SB | 4.00 | 3.03 | 5.08 | 3.42 | 2.11 | 1.64 | 1.32 | 1.07 | 0.95 | 0.83 | 0.80 |
| TG + PEG + EDTA + 3XE + 1% SB | 5.48 | 3.11 | 4.80 | 3.03 | 2.31 | 1.76 | 1.55 | 1.42 | 1.28 | 1.19 | 1.14 |

TABLE 31-continued

Fluoresecence output of gels A and D1, with various additives

| Gel + additive | | | | | | | | | | | |
|---|---|---|---|---|---|---|---|---|---|---|---|
| D1 + 3X EY + 0.2% SB | 1.48 | 1.51 | 1.50 | 1.50 | 1.50 | 1.49 | 1.49 | 1.47 | 1.48 | 1.48 | 1.47 |
| A 0% UP +3X EY + 0.2% SB | 2.28 | 2.07 | 1.81 | 1.56 | 1.10 | 0.69 | 0.87 | 0.67 | 0.62 | 0.53 | 0.51 |

| | Time/Fluorescence output | | | | | | | | | |
|---|---|---|---|---|---|---|---|---|---|---|
| Gel + additive | 5.5 | 6 | 6.5 | 7 | 7.5 | 8 | 8.5 | 9 | 9.5 | 10 |
| D1 + 3X YE + 1% SB | 3.69 | 3.62 | 3.51 | 3.46 | 3.37 | 3.30 | 3.25 | 3.17 | 3.12 | 3.08 |
| A 0% UP + 3X EY + 1% SB | 1.26 | 1.22 | 1.18 | 1.16 | 1.14 | 1.10 | 1.07 | 1.03 | 1.02 | 1.01 |
| D1 + PEG + 3X EY + 1% SB | 4.13 | 4.05 | 3.98 | 3.91 | 3.83 | 3.75 | 3.69 | 3.62 | 3.55 | 3.48 |
| D1 + EDTA + 3X EY + 1% SB | 0.71 | 0.66 | 0.63 | 0.60 | 0.57 | 0.54 | 0.53 | 0.52 | 0.48 | 0.47 |
| TG + PEG + EDTA + 3XE + 1% SB | 1.08 | 1.02 | 0.97 | 0.93 | 0.87 | 0.86 | 0.80 | 0.75 | 0.73 | 0.70 |
| D1 + 3X EY + 0.2% SB | 1.47 | 1.48 | 1.47 | 1.47 | 1.47 | 1.47 | 1.46 | 1.47 | 1.47 | 1.47 |
| A 0% UP +3X EY + 0.2% SB | 0.512 | 0.47 | 0.441 | 0.401 | 0.4 | 0.406 | 0.385 | 0.399 | 0.364 | 0.328 |

TABLE 32

Fluoresecence color output of gels A and D1, with various additives

| Gel + additive | pH | Gel texture (bubbles) | Fluorescence color output | | | | | |
|---|---|---|---|---|---|---|---|---|
| | | | Purple | Blue | Green | Yellow | Orange | Red |
| D1 + 3X YE + 1% SB | 5.65 | High | 3.41 | 0.93 | 0.44 | 0.38 | 0.22 | 0.2 |
| A 0% UP + 3X EY + 1% SB | 5.05 | Average | 2.45 | 1.52 | 0.41 | 0.27 | 0.16 | 0.17 |
| D1 + PG + 3X EY + 1% SB | 5.61 | High | 1.73 | 0.39 | 0.45 | 0.51 | 0.29 | 0.28 |
| D1 + EDTA + 3X EY + 1% SB | 5.78 | High | 6.24 | 4.36 | 0.5 | 0.14 | 0.08 | 0.07 |
| D1 + PG + EDTA + 3XE + 1% SB | 5.6 | High | 5.6 | 3.92 | 0.49 | 0.18 | 0.1 | 0.09 |
| D1 + 3X EY + 0.2% SB | 5.04 | Low | 5.99 | 1.79 | 0.19 | 0.16 | 0.08 | 0.02 |
| A 0% UP + 3X EY + 0.2% SB | 4.7 | Low | 8.92 | 5.26 | 0.19 | 0.11 | 0.06 | 0.02 |

Example 21

Altering pH with or without the Presence of Bicarbonate

An experiment was conducted to determine the fluorescence of the D1 gel under various pH conditions, with the gel either containing or lacking sodium bicarbonate.

To perform the experiment, three sample D1 gels were prepared with each having 3× Eosin Y and were measured for fluorescence (as per the procedure detailed in Example 9) under three conditions: two of the gels had their pH adjusted to pH 5, which is a standard pH setting for the D1 gel, and one of these two gels sodium bicarbonate in powder form was added, just prior to illumination of the gel, to provide a final concentration of 1% sodium bicarbonate in the gel sample. A third gel was also prepared that had its pH adjusted to pH 3, and this gel had no sodium bicarbonate added. The three test gels were thus those noted as: D1 gel at pH 5 with sodium bicarbonate; D1 gel at pH 5; and D1 gel at pH 3. Note that increasing the pH of the D1 gel to above a neutral level was not tested, as the chromophore becomes degraded at pH>7, and thus the gel will not fluoresce at all.

Each of the gels was illuminated for a period of 10 minutes at a distance of 5 cm between the lamp and the gel, and the fluorescence data were recorded using a spectrophotometer. The results from the experiment are presented in FIG. 21 and Table 32.

TABLE 33

Gel D1 fluorescence with scaling of pH

| | Fluorescence/Sample | | |
|---|---|---|---|
| Time (minutes) | Gel D1, pH 5 + 1% NaBicarb | Gel D1, pH 5 | Gel DI, pH 3 |
| 0 | 4.15 | 1.30 | 0.36 |
| 0.5 | 3.99 | 1.27 | 0.37 |
| 1 | 3.93 | 1.25 | 0.38 |
| 1.5 | 3.89 | 1.24 | 0.36 |
| 2 | 3.87 | 1.23 | 0.36 |
| 2.5 | 3.83 | 1.21 | 0.36 |
| 3 | 3.78 | 1.20 | 0.36 |
| 3.5 | 3.72 | 1.18 | 0.35 |
| 4 | 3.66 | 1.19 | 0.34 |
| 4.5 | 3.60 | 1.17 | 0.34 |
| 5 | 3.54 | 1.17 | 0.34 |
| 5.5 | 3.47 | 1.16 | 0.34 |
| 6 | 3.39 | 1.16 | 0.35 |
| 6.5 | 3.38 | 1.15 | 0.33 |
| 7 | 3.33 | 1.15 | 0.34 |
| 7.5 | 3.28 | 1.13 | 0.33 |
| 8 | 3.22 | 1.13 | 0.33 |
| 8.5 | 3.18 | 1.13 | 0.33 |
| 9 | 3.15 | 1.12 | 0.33 |
| 9.5 | 3.09 | 1.11 | 0.32 |
| 10 | 3.05 | 1.11 | 0.32 |
| AVG | 3.55 | 1.18 | 0.35 |

Figure 21:
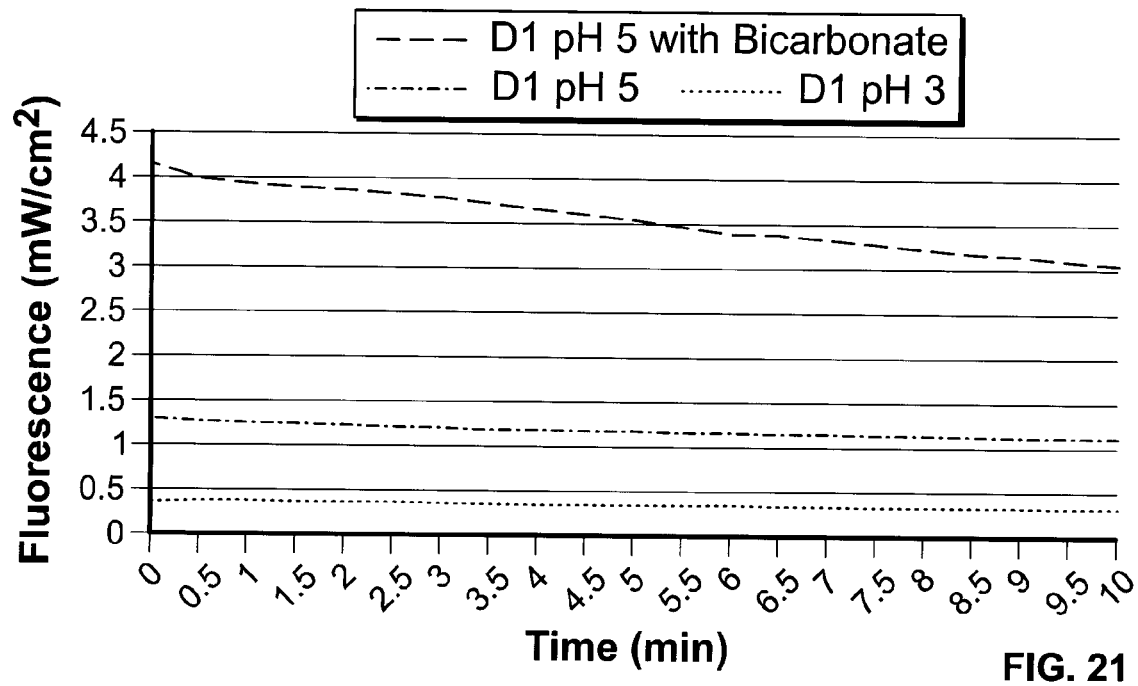
FIG. 21 illustrates the impact of changes in pH on the fluorescence of the D1 gel in the presence and absence of sodium bicarbonate (Example 21).

Referring to Table 32 and FIG. 21, it is clearly evident that the D1 gel with sodium bicarbonate had a substantially greater amount of fluorescence yield compared to an equivalent gel that lacked the added bicarbonate. Furthermore, lowering the pH of the D1 gel had a negative effect on the amount of fluorescence that the gel could produce, and was even far below the level of fluorescence that a gel A would typically produce under the same illumination conditions.

Example 22

Stability of Pre-Mixed Bicarbonate (Non-Powder)

As addition of bicarbonate to a gel composition of the present disclosure occurs by an addition of the salt in a powder form, an experiment was conducted to determine if having sodium bicarbonate stored in a separate gel could still have the same effect as when mixed with the D1 gel as sodium bicarbonate in powder form.

To perform the experiment, a gel B was basified to a very high pH (13). Then separately sodium carbonate and sodium bicarbonate were added to the gel B in excess (200 milligrams per 1 gram of gel) and mixed well so as to form a carbonate-gel B and a bicarbonate-gel B. A separate gel B was then made using an unbasified gel B (acidic) and adding glycerin (330 milligrams per 1 gram of gel) and Eosin Y (6x) to the separate gel, this prepared gel referred to as the glycerin gel for this experiment. The prepared gels were either tested on the day of preparation, or the following or kept for a one week period of time and then tested.

Figure 22:
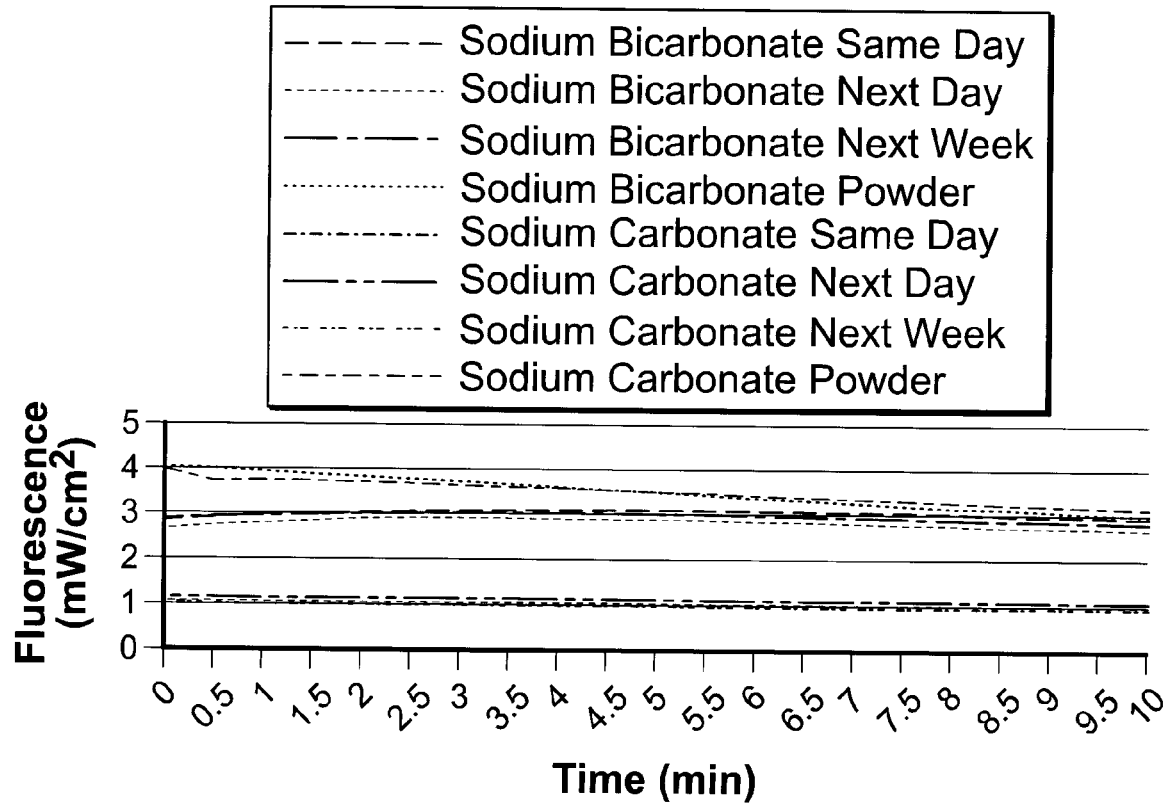
FIG. 22 illustrates the impact of adding sodium bicarbonate in a gel, solid sodium bicarbonate, sodium carbonate in a gel, or solid sodium carbonate on the fluorescence of the D1 gel. Sodium bicarbonate in a gel, solid sodium bicarbonate, sodium carbonate in a gel, or solid sodium carbonate was added at various times to the D1 gel and the fluorescence was analyzed to determine the stability of the gel (Example 22).

The spectrophotometer was prepared for taking fluorescence measurements as described in Example 9, and thereafter the glycerin gel was mixed with either the bicarbonate-gel B or the carbonate-gel B at a 10 to 1 ratio to provide a resulting gel mixture having a pH of approximately 8. After mixing for one minute, the fluorescence of the glycerin/carbonate-gel B mixture and the glycerin/bicarbonate-gel B mixtures was measured over the course of a 10 minute illumination period using the KLOX multi-LED blue light. The results from the experiment are presented in FIG. 22 and show the same day and next day results, along with the fluorescence measurements taken when the sodium bicarbonate is added in a powder form. The results indicate that at least for the gels stored overnight prior to mixing, an enhanced level of fluorescence comparable to that obtained when adding the sodium bicarbonate powder form could be obtained, thereby indicating that the highly basified gel B containing the sodium bicarbonate could be stable for a period of time.

INCORPORATION BY REFERENCE

All references cited in this specification, and their references, are incorporated by reference herein in their entirety where appropriate for teachings of additional or alternative details, features, and/or technical background.

EQUIVALENTS

While the subject matters of this disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

The invention claimed is:
1. A biophotonic composition comprising:
a first chromophore comprising a xanthene dye;
one or more gelling agents;
one or more polyols; and
one or more salts selected from one or more bicarbonate salts, one or more carbonate salts, or a combination of the foregoing salts, present in an amount of between about 0.4% and about 10% by weight of the total composition;
wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

2. The biophotonic composition of claim 1, wherein the first chromophore is present in an amount of from about 0.001% to about 40% by weight of the total composition.

3. The biophotonic composition of claim 1, wherein the gelling agent is a carbomer comprising a polymer of acrylic acid.

4. The biophotonic composition of claim 3, wherein the carbomer is crosslinked.

5. The biophotonic composition of claim 1, wherein the first chromophore is in solution in a medium of the composition.

6. The biophotonic composition of claim 5, wherein the medium is an aqueous substance or an alcohol.

7. The biophotonic composition of claim 1, wherein the first chromophore is selected from the group consisting of Eosin Y, Eosin B, Erythrosin B, Fluorescein, Rose Bengal, and Phloxin B.

8. The biophotonic composition of claim 7, wherein the first chromophore is Eosin Y.

9. The biophotonic composition of claim 1, wherein the composition further comprises a second chromophore.

10. The biophotonic composition of claim 9, wherein the first chromophore is Eosin Y, and the second chromophore is one or more selected from Fluorescein, Phloxine B and Erythrosine B.

11. The biophotonic composition of claim 9, wherein the first chromophore is Fluorescein, and the second chromophore is Eosin Y.

12. The biophotonic composition of claim 9, further comprising a third chromophore, wherein the third chromophore is a chlorophyll or saffron.

13. The biophotonic composition of claim 1, wherein the polyol is glycerine.

14. The biophotonic composition of claim 1, wherein the polyol is at least one glycol.

15. The biophotonic composition of claim 14, wherein the glycol is selected from ethylene glycol and propylene glycol.

16. The biophotonic composition of claim 1, wherein the salt is one or more bicarbonate salts selected from ammonium bicarbonate, caesium bicarbonate, potassium bicarbonate, sodium bicarbonate, choline bicarbonate, aminoguanidine bicarbonate, and tetraethylammonium bicarbonate.

17. The biophotonic composition of claim 1, wherein the first chromophore is present in an amount of from about 0.005% to about 2% by weight of the total composition, and optionally about 0.2% by weight of the total composition.

18. The biophotonic composition of claim 1, wherein the pH of the composition is within the range of from about 4.0 to about 7.0, from about 4.0 to about 7.0, from about 4.0 to about 6.5, or from about 4.0 to about 5.0.

19. A biophotonic composition comprising:
a first chromophore that emits fluorescence upon being photoactivated;
one or more gelling agents;
one or more polyols selected from diol, a triol, a saccharide, glycerine, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol; and
one or more salts selected from one or more bicarbonate salts, one or more carbonate salts, or a combination of the foregoing salts, present in an amount of between about 0.4% and about 10% by weight of the total composition;
wherein said composition does not include an oxidant selected from the group consisting of a peroxide, a peroxy acid, hydrogen peroxide, carbamide peroxide, an alkali metal peroxide, an alkali metal percarbonate, peroxyacetic acid, and an alkali metal perborate.

20. The biophotonic composition of claim 19, wherein the one or more gelling agent is selected from polyethylene glycol, poly(ethylene oxide)-poly(propylene oxide) copolymers, glycerol, propylene glycol, trimethylene glycol; polyoxyethylated sorbitol, polyoxyethylated glucose, polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), aminoethyl acrylate, mono-2-(acryloxy)-ethyl succinate, polymaleic acid, poly(acrylamides), poly(methacrylamide), poly(dimethylacrylamide), poly(N-isopropyl-acrylamide), poly(olefinic alcohol), poly(vinyl alcohol), poly(vinyl pyrrolidone), poly(N-vinyl caprolactam), poly(methyloxazoline), poly(ethyloxazoline), silicones, polyvinyl silicates, tetramethoxyorthosilicates, methyltrimethoxyorthosilicates, tetraalkoxyorthosilicates, trialkoxyorthosilicates, and polyvinylamines.

* * * * *